United States Patent
Shimizu

(10) Patent No.: US 10,752,572 B2
(45) Date of Patent: Aug. 25, 2020

(54) METHOD FOR PRODUCING ACETIC ACID

(71) Applicant: DAICEL CORPORATION, Osaka-shi, Osaka (JP)

(72) Inventor: Masahiko Shimizu, Himeji (JP)

(73) Assignee: DAICEL CORPORATION, Osaka-Shi, Osaka (JP)

( * ) Notice: Subject to any disclaimer, the term of this patent is extended or adjusted under 35 U.S.C. 154(b) by 0 days.

(21) Appl. No.: 16/334,673

(22) PCT Filed: May 29, 2018

(86) PCT No.: PCT/JP2018/020602
§ 371 (c)(1),
(2) Date: Mar. 19, 2019

(87) PCT Pub. No.: WO2019/229856
PCT Pub. Date: Dec. 5, 2019

(65) Prior Publication Data
US 2020/0123093 A1    Apr. 23, 2020

(51) Int. Cl.
*C07C 51/12* (2006.01)
*C07C 51/48* (2006.01)
*C07C 51/44* (2006.01)

(52) U.S. Cl.
CPC ............ *C07C 51/445* (2013.01); *C07C 51/12* (2013.01)

(58) Field of Classification Search
CPC ......... C07C 51/12; C07C 51/44; C07C 51/48; C07C 51/445
See application file for complete search history.

(56) References Cited

U.S. PATENT DOCUMENTS

| | | | |
|---|---|---|---|
| 4,204,915 A | 5/1980 | Kurata et al. | |
| 5,371,286 A | 12/1994 | Blay et al. | |
| 5,625,095 A | 4/1997 | Miura et al. | |
| 5,723,660 A | 3/1998 | Morimoto et al. | |
| 5,756,836 A | 5/1998 | Shimizu et al. | |
| 6,143,930 A | 11/2000 | Singh et al. | |
| 9,006,483 B2 | 4/2015 | Shimizu et al. | |
| 9,540,304 B2 | 1/2017 | Liu et al. | |
| 2007/0093676 A1 | 4/2007 | Kojima et al. | |
| 2015/0025270 A1 | 1/2015 | Shimizu et al. | |
| 2016/0137576 A1 | 5/2016 | Liu et al. | |
| 2017/0260120 A1 | 9/2017 | Shimizu et al. | |

FOREIGN PATENT DOCUMENTS

| | | |
|---|---|---|
| EP | 0645362 A1 | 3/1995 |
| EP | 3333147 A1 | 6/2018 |
| JP | 53-116314 A | 10/1978 |
| JP | 4-295445 A | 10/1992 |
| JP | 7-25813 A | 1/1995 |
| JP | 7-133249 A | 5/1995 |
| JP | 8-67650 A | 3/1996 |
| JP | 2001-508405 A | 6/2001 |
| JP | 2016-117709 A | 6/2016 |
| WO | WO 96/33965 A1 | 10/1996 |
| WO | WO 2006/070632 A1 | 7/2006 |
| WO | WO 2013/137236 A1 | 9/2013 |
| WO | WO 2017/149856 A1 | 9/2017 |
| WO | WO 2018/078924 A1 | 5/2018 |

OTHER PUBLICATIONS

Extended European Search Report dated Oct. 7, 2019, in European Patent Application No. 18855140.2.
U.S. Appl. No. 16/334,659, filed Mar. 19, 2019, Unassigned.
U.S. Appl. No. 16/334,654, filed Mar. 19, 2019, Unassigned.
U.S. Appl. No. 16/483,808, filed Aug. 6, 2019, Unassigned.
English translation of the Written Opinion of the International Searching Authority dated Oct. 22, 2019, in PCT/JP2018/027894 (Forms PCT/IB/310 and PCT/IB/237).
International Search Report dated Sep. 4, 2018, in PCT/JP2018/027894.
International Search Report and Written Opinion of the International Searching Authority for International Application No. PCT/JP2018/020602, dated Jul. 31, 2018.
Extended European Search Report for European Application No. 18857376.0, dated Nov. 27, 2019.
International Search Report dated Jul. 31, 2018, in PCT/JP2018/020605.
Extended European Search Report for European Application No. 18903038.0, dated May 28, 2020.

*Primary Examiner* — Sikarl A Witherspoon
(74) *Attorney, Agent, or Firm* — Birch, Stewart, Kolasch & Birch, LLP

(57) ABSTRACT

Provided is a method for industrially efficiently producing acetic acid that yields a good potassium permanganate test result, without enormous cost. A light ends column (first distillation column) is operated with a reflux ratio at a specific level or more, a distillation column (crotonaldehyde-removing column) is provided for treating an organic phase of an overhead condensate from the light ends column, and the crotonaldehyde-removing column is operated under such conditions as to meet at least one of conditions (i) to (iii) as follows: (i) a reflux ratio at the distillation column is 0.01 or more; (ii) at the distillation column, the ratio of a crotonaldehyde concentration in a distillate to a crotonaldehyde concentration in a charge liquid is less than 1; and (iii) at the distillation column, the ratio of a crotonaldehyde concentration in bottoms to a crotonaldehyde concentration in the charge liquid is greater than 1.

20 Claims, 5 Drawing Sheets

[FIG. 1]
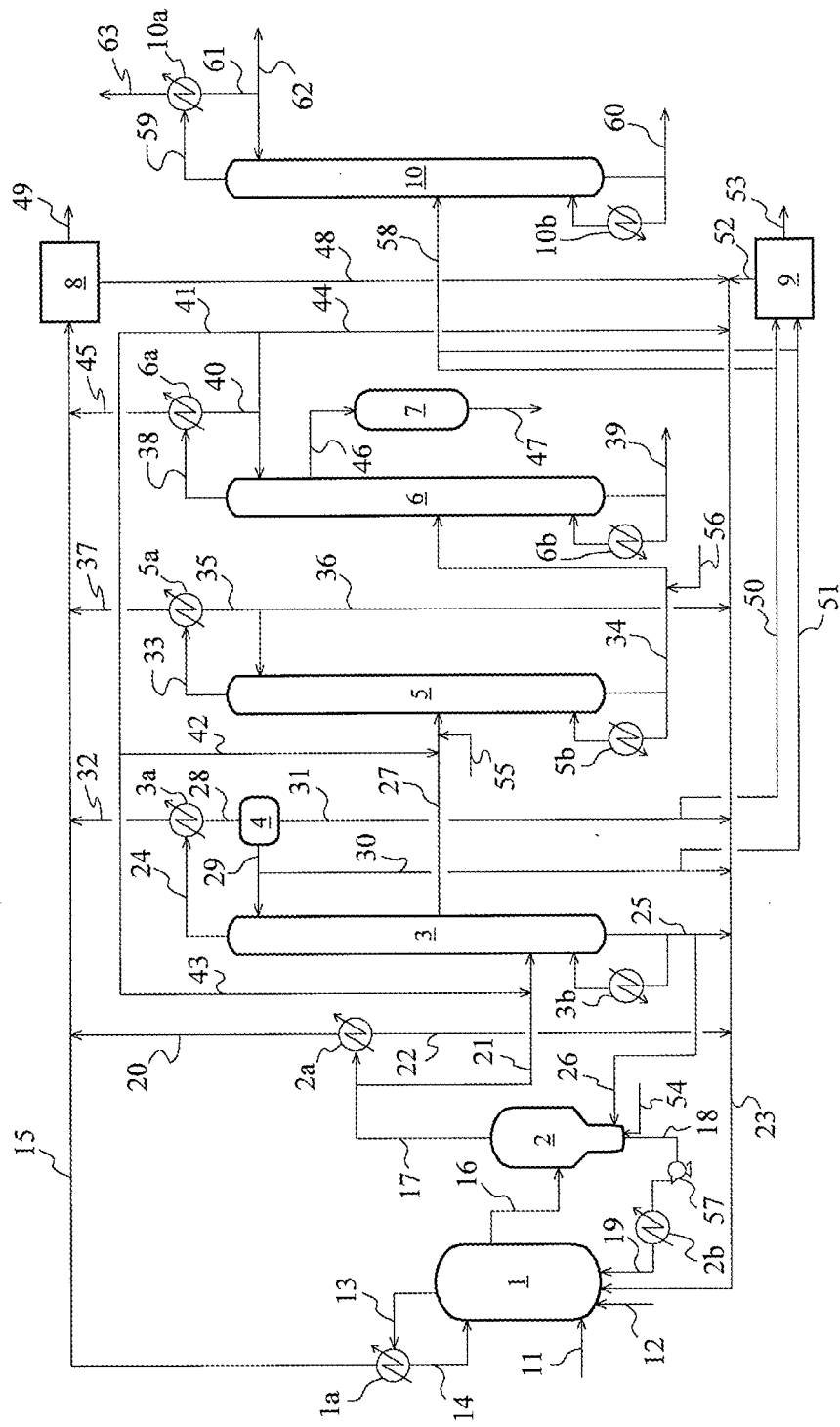

[FIG. 2]
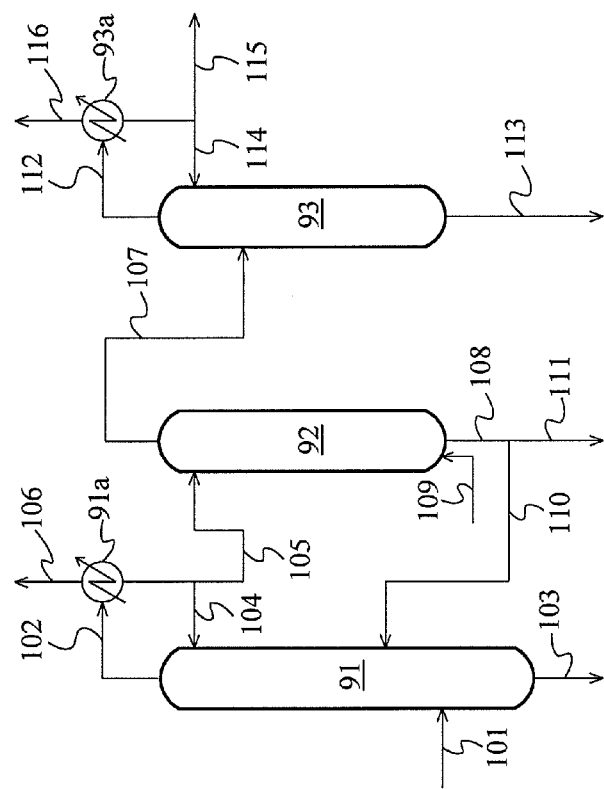

[FIG. 3]
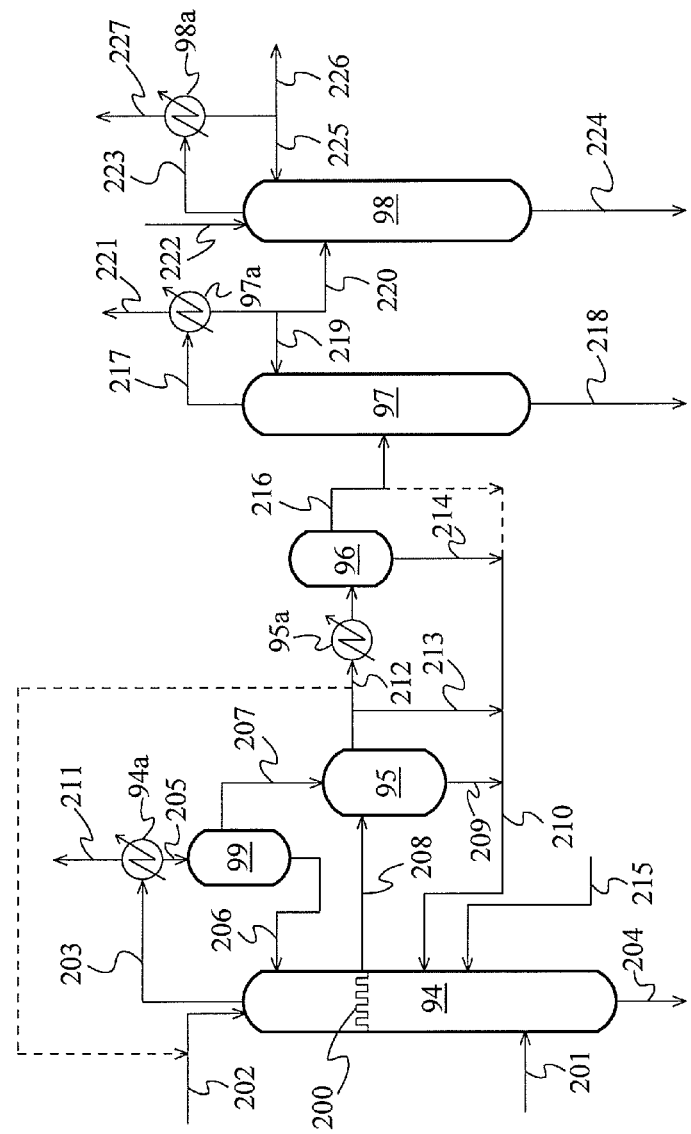

[FIG. 4]
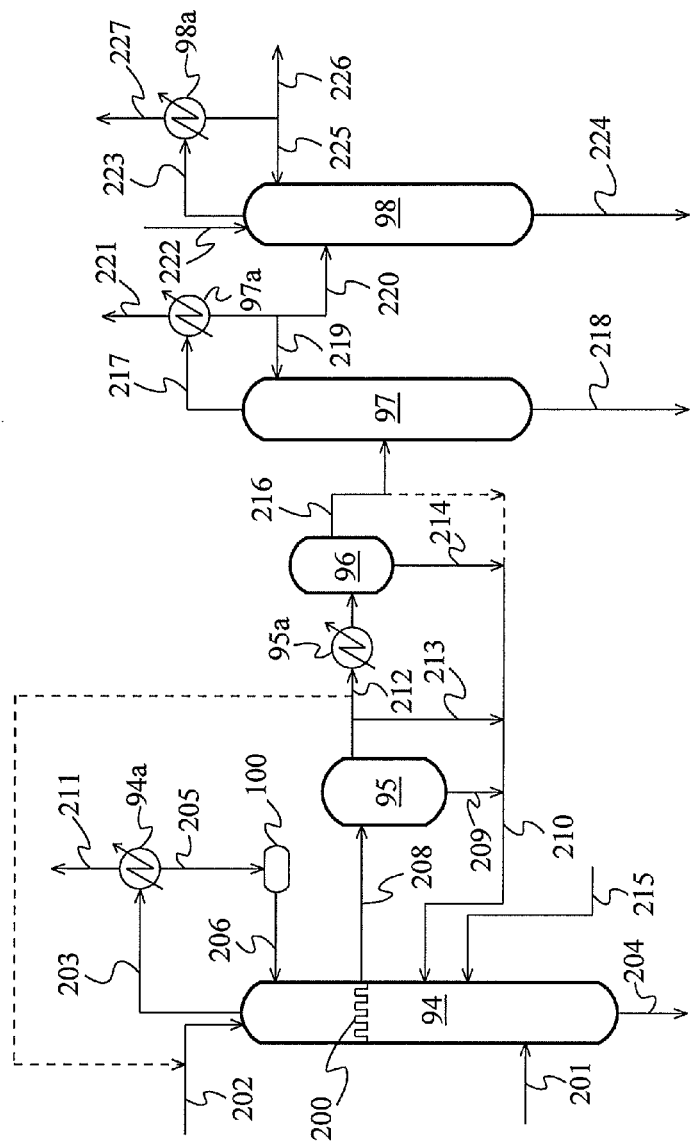

[FIG. 5]
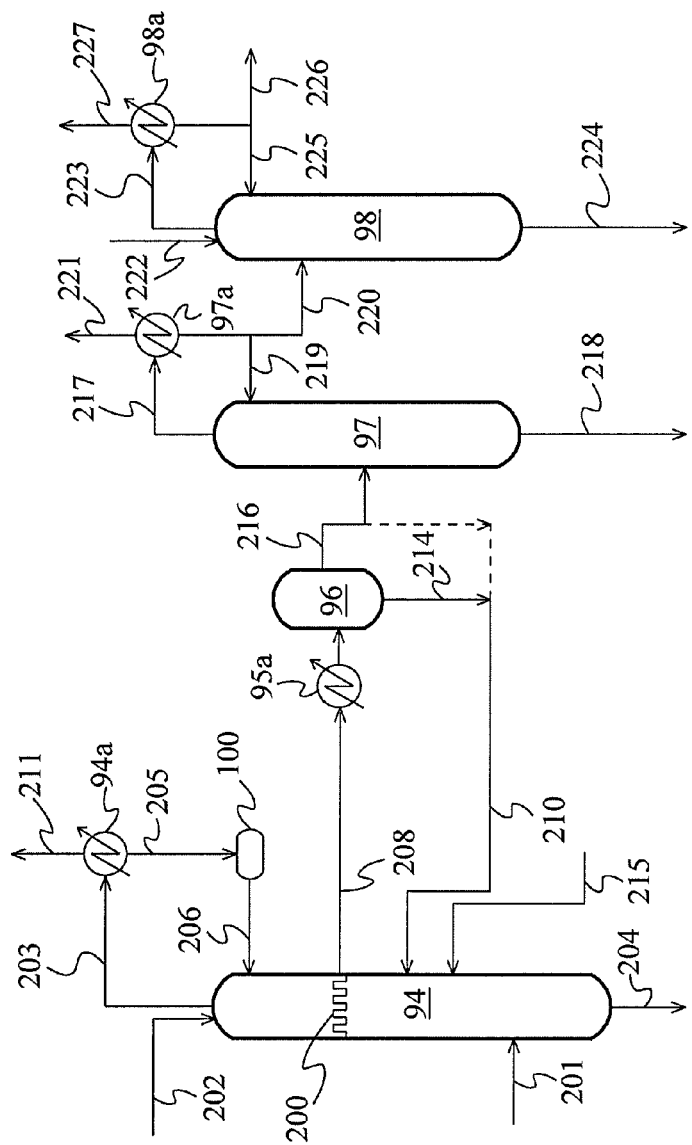

METHOD FOR PRODUCING ACETIC ACID

TECHNICAL FIELD

The present invention relates to methods for producing acetic acid.

BACKGROUND ART

A methanol carbonylation process (methanol-acetic acid process) is known as a process for industrially producing acetic acid. With this process, an acetic acid product is produced typically by allowing methanol to react with carbon monoxide in the presence of a catalyst in a reactor, to form acetic acid in a reaction mixture, evaporating the reaction mixture using an evaporator into a vapor phase, and purifying the vapor phase through a light ends column, and subsequently through a dehydration column. Alternatively, the product from the dehydration column is further fed to a subsequent heavy ends column and, in some cases, a subsequent product column to give an acetic acid product.

In the acetic acid production process as above, acetaldehyde, which results from reduction of methyl iodide, is converted into crotonaldehyde by aldol condensation, and causes the acetic acid product to yield a worse potassium permanganate test result (permanganate time). In addition, crotonaldehyde is converted into 2-ethylcrotonaldehyde by aldol condensation with acetaldehyde; and 2-ethylcrotonaldehyde also causes the acetic acid product to yield a worse potassium permanganate test result. However, as compared with 2-ethylcrotonaldehyde, crotonaldehyde more worsens the potassium permanganate test result per mass unit, and, when contained in the acetic acid product, more significantly worsens the quality of the product.

To decrease crotonaldehyde and/or 2-ethylcrotonaldehyde, roughly classified two techniques have been conventionally industrially employed (Patent Literature (PTL) 1 and PTL 2). One is (i) the technique of restraining the formation of crotonaldehyde in a reaction system by removing acetaldehyde, which is by-produced in the reaction system, from methyl iodide in a purification step, and decreasing acetaldehyde in the methyl iodide to be recycled to the reaction system. The other is (ii) the technique of directly decomposing crotonaldehyde oxidatively with ozone, where the crotonaldehyde is contained in a crude acetic acid which is obtained in the middle of a purification step. However, facilities for the acetaldehyde separation and removal, and facilities for the ozone treatment are both expensive. Conventional acetic acid production processes entirely depend on these techniques so as to give an acetic acid product that yields a better potassium permanganate test result, and this leads to increase in installation cost.

The methanol-acetic acid process is known to give alkanes as impurities. The alkanes are impurities which contain 3 or more carbon atoms, and which have higher boiling points as compared with methyl iodide and methyl acetate. The alkanes are mainly saturated or unsaturated hydrocarbons, but may contain an oxygen atom and/or an iodine atom in the molecule. Japanese Unexamined Patent Application Publication (JP-A) No. H04-295445 discloses a technique for the removal of the alkanes. In the technique, of overhead condensates from a light ends column, an organic phase is subjected to distillation in a distillation column (alkane-removing column), to give an overhead product including methyl iodide, methyl acetate, and carbonyl impurities, and bottoms including alkanes, water, and acetic acid; the overhead product is recycled to the reactor or fed to an acetaldehyde-removing column, the bottoms are combined with and extracted with water to give an aqueous phase including acetic acid, and an organic phase including alkanes; the aqueous phase is recycled to the reactor, and the organic phase including the alkanes is discarded as a waste. This literature, however, neither discloses nor indicates how to allow the acetic acid product to yield a better potassium permanganate test result.

CITATION LIST

Patent Literature

PTL 1: JP-A No. H07-25813
PTL 2: Japanese Unexamined Patent Application Publication (Translation of PCT Application) (JP-A) No. 2001-508405
PTL 3: JP-A No. H04-295445

SUMMARY OF INVENTION

Technical Problem

Accordingly, the present invention has an object to provide a method for industrially efficiently producing acetic acid that yields a good potassium permanganate test result, without costing much.

Solution to Problem

After intensive investigations to achieve the object, the inventor of the present invention found that bottoms (bottom liquid) from a dehydration column in a methanol carbonylation process can have a lower crotonaldehyde concentration and can yield a significantly better potassium permanganate test result, by operating a light ends column (first distillation column) with a reflux ratio at a specific level or more; providing a distillation column (crotonaldehyde-removing column) that treats an organic phase of an overhead condensate from the light ends column, and operating the crotonaldehyde-removing column under specified conditions; controlling the crotonaldehyde concentration in an acetic acid stream (first acetic acid stream) at a specific level or less, where the acetic acid stream results from removal of light ends in the light ends column, and/or operating a dehydration column (second distillation column) with a reflux ratio at a specific level or more; and decreasing at least one of the ratio of a crotonaldehyde concentration to a 2-ethylcrotonaldehyde concentration, and the ratio of a crotonaldehyde concentration to a butyl acetate concentration, in at least one of the first acetic acid stream, and an acetic acid-rich stream resulting from further purification of the first acetic acid stream.

More specifically, at an increased reflux ratio at the light ends column, crotonaldehyde is concentrated at the top of the distillation column (light ends column), because crotonaldehyde has a boiling point (104° C.) lower than the boiling point (117° C.) of acetic acid. The concentrated crotonaldehyde, when recycled to the reactor, reacts with acetaldehyde in the reactor to form 2-ethylcrotonaldehyde. The crotonaldehyde also reacts with hydrogen in the reactor to form butanol, and butanol in turn reacts with acetic acid to form butyl acetate. As compared with crotonaldehyde, 2-ethylcrotonaldehyde less affects the potassium permanganate test result; and butanol and butyl acetate approximately do not affect the potassium permanganate test result and are harmless. Accordingly, by enhancing or facilitating conversion from crotonaldehyde to 2-ethylcrotonaldehyde and/or conversion from crotonaldehyde through butanol to butyl acetate, the acetic acid-rich stream from the light ends column is allowed to have a lower crotonaldehyde concentration to thereby have a lower ratio of the crotonaldehyde concentration to the 2-ethylcrotonaldehyde concentration, and/or a lower ratio of the crotonaldehyde concentration to a butyl acetate concentration; and a stream rich in acetic acid (such as bottoms from the after-mentioned dehydration column) resulting from further purification of the acetic acid-rich stream is allowed to have a lower crotonaldehyde concentration to thereby have a lower ratio of the crotonaldehyde concentration to the 2-ethylcrotonaldehyde concentration, and/or a lower ratio of the crotonaldehyde concentration to the butyl acetate concentration. Accordingly, acetic acid tends to have still better quality. At such a higher reflux ratio of the light ends column, 2-ethylcrotonaldehyde and butyl acetate are present in further lower concentrations at the column top, because 2-ethylcrotonaldehyde and butyl acetate have boiling points respectively of 137° C. and 126° C. higher than the boiling point (117° C.) of acetic acid. The two components are recycled in bottoms from the light ends column to the reaction system and concentrated, or a part of them is fed from (as) a sidecut to a subsequent step, or is contained in the acetic acid product, where the sidecut is drawn at a level higher than the charge liquid feeding level.

The control of the reflux ratio at the dehydration column to a specific level or more allows crotonaldehyde flowing into the dehydration column to be concentrated at the column top, because crotonaldehyde has a lower boiling point as compared with acetic acid, and this can significantly lower the crotonaldehyde concentration in a second acetic acid stream obtained as a side stream or a bottoms stream. When the crotonaldehyde-concentrated overhead stream (second overhead stream) from the concentrated dehydration column top is recycled to the reactor, crotonaldehyde is converted to 2-ethylcrotonaldehyde, which less adversely affects the potassium permanganate test result, and to butyl acetate, which does not adversely affect the potassium permanganate test result. This allows the acetic acid (product) to have still better quality.

In addition, assume that the light ends column overhead condensate, in which crotonaldehyde is concentrated, is subjected to a distillation treatment, separately from an acetaldehyde-removing treatment. This enables efficient separation of useful methyl iodide and unnecessary crotonaldehyde from each other. Specifically, for example, when an organic phase of the light ends column overhead condensate is subjected to such a distillation treatment, methyl iodide can be obtained as an overhead product together with methyl acetate. This can be recycled to at least one of a decanter and the reactor, where the decanter is provided for storage of the light ends column overhead condensate. Herein, crotonaldehyde is obtained as bottoms with other high-boiling impurities (such as 2-ethylcrotonaldehyde, butyl acetate, and alkanes) and acetic acid. The bottoms are removed out of the system and are discarded. Water may be concentrated at the column top or may be drawn from the column bottom. A conventionally known alkane-removing column can be used as the crotonaldehyde-removing column. The alkane-removing column may be operated continuously, but may be operated batchwise when alkanes are formed at low rates. In such batchwise operation, the acetic acid product may yield a lower (worse) potassium permanganate test result. To eliminate or minimize this, the product quality should be maintained by at least one of an acetaldehyde-removing treatment, an ozone treatment, and change in operation conditions. In this connection, 2-ethylcrotonaldehyde is also present in a trace amount at the light ends column top, and this can also be discharged out of the system by the operation, and contributes to a better potassium permanganate test result, as with crotonaldehyde. However, the effects of this are limited, because 2-ethylcrotonaldehyde, which has a high boiling point, is hardly concentrated (enriched) at the top of the light ends column. Of the light ends column overhead condensate, mainly the organic phase is fed to the crotonaldehyde-removing column. In addition to, or instead of this, the aqueous phase of the light ends column overhead condensate may be fed to the crotonaldehyde-removing column. Thus, the acetic acid product can yield a better potassium permanganate test result by the easy and simple procedure as above. This can downsize or eliminate acetaldehyde-removing facilities and ozone treatment facilities, and can reduce steam cost and electric utility expense. The present invention has been made on the basis of these findings and further investigations.

Specifically, the present invention provides, in one aspect, a method for producing acetic acid as follows (hereinafter also referred to as a "first acetic acid production method"). This method includes a carbonylation step, a separation step, a recycling step, and a crotonaldehyde-removing step. In the carbonylation step, methanol is reacted (carbonylated) with carbon monoxide in a reactor in the presence of a catalytic system, acetic acid, methyl acetate, and water, to give acetic acid in a reaction mixture, where the catalytic system includes a metal catalyst and methyl iodide. In the separation step, the reaction mixture from the carbonylation step is separated, using at least one selected from evaporators and distillation columns, into a stream including the metal catalyst, an acetic acid stream rich in acetic acid, and a stream rich in light ends as compared with the acetic acid stream. In the recycling step, at least a part of the light ends-rich stream is recycled to the reactor. In the crotonaldehyde-removing step, crotonaldehyde is separated and removed from at least a part of a remainder of the light ends-rich stream by a treatment in a distillation column.

The separation step includes a first separation step of separating the reaction mixture, using a first distillation column, into a first acetic acid stream rich in acetic acid, and an overhead stream rich in light ends as compared with the first acetic acid stream, and condensing the overhead stream to give a condensate.

In the method, a reflux ratio at the first distillation column is controlled as follows. Provided that the condensate is liquid-liquid separated into an aqueous phase and an organic phase, the reflux ratio for the aqueous phase is 2 or more when the aqueous phase alone is refluxed to the first distillation column, the reflux ratio for the organic phase is 1 or more when the organic phase alone is refluxed to the first distillation column, and the total reflux ratio for the aqueous phase and the organic phase is 1.5 or more when both the aqueous phase and the organic phase are refluxed to the first distillation column. Alternatively, provided that the condensate is refluxed to the first distillation column without liquid-liquid separation, the reflux ratio for the condensate is 1.5 or more.

In the method, the distillation column is operated in the crotonaldehyde-removing step so as to meet at least one of conditions (i) to (iii) as follows:

(i) a reflux ratio at the distillation column is 0.01 or more;

(ii) at the distillation column, the ratio of a crotonaldehyde concentration (ppm by mass) in a distillate to a crotonaldehyde concentration (ppm by mass) in a charge liquid is less than 1; and (iii) at the distillation column, the ratio of a crotonaldehyde concentration (ppm by mass) in bottoms to a crotonaldehyde concentration (ppm by mass) in the charge liquid is greater than 1.

In the method, the crotonaldehyde concentration in the first acetic acid stream is controlled to 2.2 ppm by mass or less, and at least one ratio is lowered, to give an acetic acid product that yields a better potassium permanganate test result, where the at least one ratio is selected from the group consisting of: the ratio ($C_{CR}/C_{ECR}$) of a crotonaldehyde concentration $C_{CR}$ (ppm by mass) to a 2-ethylcrotonaldehyde concentration $C_{ECR}$ (ppm by mass) in the first acetic acid stream, the ratio ($C_{CR}/C_{BA}$) of a crotonaldehyde concentration $C_{CR}$ (ppm by mass) to a butyl acetate concentration $C_{BA}$ (ppm by mass) in the first acetic acid stream, the ratio ($C_{CR}/C_{ECR}$) of a crotonaldehyde concentration $C_{CR}$ (ppm by mass) to a 2-ethylcrotonaldehyde concentration $C_{ECR}$ (ppm by mass) in an acetic acid-rich stream resulting from further purification of the first acetic acid stream, and the ratio ($C_{CR}/C_{BA}$) of a crotonaldehyde concentration $C_{CR}$ (ppm by mass) to a butyl acetate concentration $C_{BA}$ (ppm by mass) in the acetic acid-rich stream resulting from further purification of the first acetic acid stream.

The present invention also provides, in another aspect, a method for producing acetic acid as follows (hereinafter also referred to as a "second acetic acid production method"). This method includes a carbonylating step, a separation step, a recycling step, and a crotonaldehyde-removing step. In the carbonylation step, methanol is reacted (carbonylated) with carbon monoxide in a reactor in the presence of a catalytic system, acetic acid, methyl acetate, and water, to give acetic acid in a reaction mixture, where the catalytic system includes a metal catalyst and methyl iodide. In the separation step, the reaction mixture from the carbonylation step is separated, using at least one selected from evaporators and distillation columns, into a stream including the metal catalyst, an acetic acid stream rich in acetic acid, and a stream rich in light ends as compared with the acetic acid stream. In the recycling step, at least a part of the light ends-rich stream is recycled to the reactor. In the crotonaldehyde-removing step, crotonaldehyde is separated and removed from at least a part of the remainder of the light ends-rich stream by a treatment in a distillation column.

The separation step includes a first separation step and a second separation step. The first separation step is the step of separating the reaction mixture, using a first distillation column, into a first acetic acid stream rich in acetic acid, and an overhead stream rich in light ends as compared with the first acetic acid stream, and condensing the overhead stream to give a condensate. The second separation step is the step of subjecting the first acetic acid stream to distillation in a second distillation column to further purify acetic acid.

In the method, a reflux ratio at the first distillation column is controlled as follows. Provided that the condensate is liquid-liquid separated into an aqueous phase and an organic phase, the reflux ratio for the aqueous phase is 2 or more when the aqueous phase alone is refluxed to the first distillation column, the reflux ratio for the organic phase is 1 or more when the organic phase alone is refluxed to the first distillation column, and the total reflux ratio for the aqueous phase and the organic phase is 1.5 or more when both the aqueous phase and the organic phase are refluxed to the first distillation column. Alternatively, provided that the condensate is refluxed to the first distillation column without liquid-liquid separation, the reflux ratio for the condensate is 1.5 or more.

In the method, the distillation column is operated in the crotonaldehyde-removing step so as to meet at least one of conditions (i) to (iii) as follows:

(i) a reflux ratio at the distillation column is 0.01 or more;

(ii) at the distillation column, the ratio of a crotonaldehyde concentration (ppm by mass) in a distillate to a crotonaldehyde concentration (ppm by mass) in a charge liquid is less than 1; and (iii) at the distillation column, the ratio of a crotonaldehyde concentration (ppm by mass) in bottoms to a crotonaldehyde concentration (ppm by mass) in the charge liquid is greater than 1.

In the method, the crotonaldehyde concentration in the first acetic acid stream is controlled to 2.2 ppm by mass or less, and/or a reflux ratio at the second distillation column is controlled to 0.1 or more, and at least one ratio is lowered, to give an acetic acid product that yields a better potassium permanganate test result, where the at least one ratio is selected from the group consisting of: the ratio ($C_{CR}/C_{ECR}$) of a crotonaldehyde concentration $C_{CR}$ (ppm by mass) to a 2-ethylcrotonaldehyde concentration $C_{ECR}$ (ppm by mass) in the first acetic acid stream; the ratio ($C_{CR}/C_{BA}$) of a crotonaldehyde concentration $C_{CR}$ (ppm by mass) to a butyl acetate concentration $C_{BA}$ (ppm by mass) in the first acetic acid stream; the ratio ($C_{CR}/C_{ECR}$) of a crotonaldehyde concentration $C_{CR}$ (ppm by mass) to a 2-ethylcrotonaldehyde concentration $C_{ECR}$ (ppm by mass) in an acetic acid-rich stream from the second separation step; and the ratio ($C_{CR}/C_{BA}$) of a crotonaldehyde concentration $C_{CR}$ (ppm by mass) to a butyl acetate concentration $C_{BA}$ (ppm by mass) in the acetic acid-rich stream from the second separation step.

The separation step in the first and second acetic acid production methods may include an evaporation step and a light ends-removing step. The evaporation step is the step of separating the reaction mixture resulting from the carbonylation step into a vapor stream and a residue stream (residual liquid stream), using an evaporator. The light ends-removing step serves as the first separation step and is the step of separating the vapor stream, using the first distillation column, into a first overhead stream rich in at least one light end selected from methyl iodide and acetaldehyde, and the first acetic acid stream rich in acetic acid, and condensing the first overhead stream.

The light ends-removing step in the first and second acetic acid production methods may include liquid-liquid separating a condensate derived from the first overhead stream into an aqueous phase and an organic phase.

The crotonaldehyde-removing step in the first and second acetic acid production methods may include removing crotonaldehyde from at least a part of at least one liquid by a treatment in a distillation column, where the at least one liquid is selected from the group consisting of the condensate resulting from condensation of the first overhead stream, the aqueous phase resulting from liquid-liquid separation of the condensate, and the organic phase resulting from liquid-liquid separation of the condensate.

The first and second acetic acid production methods may further include an acetaldehyde-removing step. The acetaldehyde-removing step is the step of removing acetaldehyde from at least a part of at least one liquid by distillation, where the at least one liquid is selected from the group consisting of the condensate resulting from condensation of the first overhead stream, the aqueous phase resulting from liquid-liquid separation of the condensate, and the organic phase resulting from liquid-liquid separation of the condensate. In this case, at least a part of a residue after separation and removal of acetaldehyde from the at least a part of at least one liquid may be recycled to the reactor, where the at least one liquid is selected from the group consisting of the condensate, the aqueous phase resulting from liquid-liquid separation of the condensate, and the organic phase resulting from liquid-liquid separation of the condensate.

The separation step in the first and second acetic acid production methods may include a dehydration step as a second separation step. The dehydration step is the step of separating the first acetic acid stream, using a second distillation column, into a second overhead stream rich in water, and a second acetic acid stream rich in acetic acid as compared with the first acetic acid stream.

The recycling step in the first and second acetic acid production methods may include recycling at least a part of at least one liquid to the reactor, where the at least one liquid is selected from the group consisting of the condensate resulting from condensation of the first overhead stream, the aqueous phase resulting from liquid-liquid separation of the condensate, the organic phase resulting from liquid-liquid separation of the condensate, and the second overhead stream.

The second distillation column may be operated at a reflux ratio of typically 0.1 or more.

The second acetic acid stream has a crotonaldehyde concentration of typically 2.0 ppm by mass or less.

The second acetic acid stream has a 2-ethylcrotonaldehyde concentration of typically 3.0 ppm by mass or less.

The second acetic acid stream has a ratio ($C_{CR}/C_{ECR}$) of the crotonaldehyde concentration $C_{CR}$ (ppm by mass) to the 2-ethylcrotonaldehyde concentration $C_{ECR}$ (ppm by mass) of typically 50 or less.

The second acetic acid stream has a butyl acetate concentration of typically 15 ppm by mass or less.

The second acetic acid stream has a ratio ($C_{CR}/C_{BA}$) of the crotonaldehyde concentration $C_{CR}$ (ppm by mass) to the butyl acetate concentration $C_{BA}$ (ppm by mass) of typically 2.0 or less.

The second acetic acid stream has a crotonaldehyde concentration of typically 0.98 ppm by mass or less, a 2-ethylcrotonaldehyde concentration of typically 1.0 ppm by mass or less, and a butyl acetate concentration of typically 15 ppm by mass or less.

The second acetic acid stream preferably gives a potassium permanganate test result of longer than 50 minutes.

The catalytic system in the first and second acetic acid production methods may further include an ionic iodide.

A hydrogen partial pressure in the reactor is typically 0.001 MPa (absolute pressure) or more.

A liquid reaction mixture in the reactor has an acetaldehyde concentration of typically 500 ppm by mass or less.

The first acetic acid stream has a 2-ethylcrotonaldehyde concentration of typically 3.0 ppm by mass or less.

The first acetic acid stream has a ratio ($C_{CR}/C_{ECR}$) of the crotonaldehyde concentration $C_{CR}$ (ppm by mass) to the 2-ethylcrotonaldehyde concentration $C_{ECR}$ (ppm by mass) of typically 50 or less.

The first acetic acid stream has a butyl acetate concentration of typically 15 ppm by mass or less.

The first acetic acid stream has a ratio ($C_{CR}/C_{BA}$) of the crotonaldehyde concentration $C_{CR}$ (ppm by mass) to the butyl acetate concentration $C_{BA}$ (ppm by mass) of typically 2.0 or less.

The first acetic acid stream has a crotonaldehyde concentration of typically 1.3 ppm by mass or less, a 2-ethylcrotonaldehyde concentration of typically 1.0 ppm by mass or less, and a butyl acetate concentration of typically 15 ppm by mass or less.

The vapor stream to be fed to the first distillation column has a crotonaldehyde concentration of typically 0 to 5.0 ppm by mass, a 2-ethylcrotonaldehyde concentration of typically 0 to 3.0 ppm by mass, and a butyl acetate concentration of typically 0.1 to 13.0 ppm by mass.

The charge liquid fed to the distillation column in the crotonaldehyde-removing step has a crotonaldehyde concentration of typically 0.01 to 50 ppm by mass.

In the crotonaldehyde-removing step, the distillation column is preferably operated so as to meet all the conditions (i) to (iii).

The distillation treatment in the crotonaldehyde-removing step may be performed batchwise.

The distillation column in the crotonaldehyde-removing step may be operated at a throughput of typically 0.0001 to 50 parts by mass per 100 parts by mass of the amount of the vapor stream fed to the first distillation column.

Advantageous Effects of Invention

The present invention enables industrially efficient production of high-quality acetic acid through a methanol carbonylation process, without providing large-scale acetaldehyde-removing facilities and ozone treatment facilities, where the acetic acid yields a good potassium permanganate test result (also called "permanganate time" (chameleon time)). This is because as follows. With the method, a light ends column is operated with a reflux ratio at a specific level or more, and a crotonaldehyde-removing step is provided, to efficiently remove crotonaldehyde. The crotonaldehyde concentration in an acetic acid stream (first acetic acid stream) from the light ends column is controlled at a specific level or less, and/or the reflux ratio at a dehydration column is controlled at a specific level or more. Also with the method, at least one ratio is lowered, where the at least one ratio is selected from the group consisting of the ratio of a crotonaldehyde concentration to a 2-ethylcrotonaldehyde concentration in the first acetic acid stream, the ratio of a crotonaldehyde concentration to a butyl acetate concentration in the first acetic acid stream, the ratio of a crotonaldehyde concentration to a 2-ethylcrotonaldehyde in an acetic acid-rich stream resulting from further purification of the first acetic acid stream, and the ratio of a crotonaldehyde concentration to a butyl acetate concentration in the acetic acid-rich stream resulting from further purification of the first acetic acid stream.

BRIEF DESCRIPTION OF DRAWINGS

FIG. 1 is a flow chart illustrating acetic acid production according to an embodiment of the present invention;

FIG. 2 is a schematic flow chart illustrating an acetaldehyde removing system according to an embodiment;

FIG. 3 is a schematic flow chart illustrating an acetaldehyde removing system according to another embodiment;

FIG. 4 is a schematic flow chart illustrating an acetaldehyde removing system according to yet another embodiment; and FIG. 5 is a schematic flow chart illustrating an acetaldehyde removing system according to still another embodiment.

DESCRIPTION OF EMBODIMENTS

The first acetic acid production method according to the present invention gives an acetic acid product that yields a better potassium permanganate test result, by configurations as follows. Specifically, the first acetic acid production method includes a carbonylation step, a separation step, a recycling step, and a crotonaldehyde-removing step. In the carbonylation step, methanol is carbonylated (reacted) with carbon monoxide in a reactor in the presence of a catalytic system, acetic acid, methyl acetate, and water, to give acetic acid in a reaction mixture, where the catalytic system includes a metal catalyst and methyl iodide. In the separation step, the reaction mixture from the carbonylation step is separated, using at least one selected from evaporators and distillation columns, to give a stream including the metal catalyst, an acetic acid stream rich in acetic acid, and a stream rich in light ends as compared with the acetic acid stream. In the recycling step, at least a part of the light ends-rich stream is recycled to the reactor. In the crotonaldehyde-removing step, at least a part of the remainder of the light ends-rich stream is treated in a distillation column to separate and remove crotonaldehyde therefrom. The separation step includes a first separation step. In the first separation step, the reaction mixture is separated, using a first distillation column, into a first acetic acid stream rich in acetic acid, and an overhead stream rich in light ends as compared with the first acetic acid stream, and the overhead stream is condensed to give a condensate. The reflux ratio at the first distillation column is controlled as follows. Provided that the condensate is liquid-liquid separated into an aqueous phase and an organic phase, the reflux ratio for the aqueous phase is 2 or more when the aqueous phase alone is refluxed to the first distillation column; the reflux ratio for the organic phase is 1 or more when the organic phase alone is refluxed to the first distillation column; and the total reflux ratio for the aqueous phase and the organic phase is 1.5 or more when both the aqueous phase and the organic phase are refluxed to the first distillation column. Alternatively, provided that the condensate is refluxed to the first distillation column without liquid-liquid separation, the reflux ratio for the condensate is 1.5 or more. In addition, the distillation column is operated in the crotonaldehyde-removing step so as to meet at least one of conditions (i) to (iii). A crotonaldehyde concentration in the first acetic acid stream is controlled to 2.2 ppm by mass or less, and at least one ratio is lowered, where the at least one ratio is selected from the group consisting of the ratio ($C_{CR}/C_{ECR}$) of a crotonaldehyde concentration $C_{CR}$ (ppm by mass) to a 2-ethylcrotonaldehyde concentration $C_{ECR}$ (ppm by mass) in the first acetic acid stream, the ratio ($C_{CR}/C_{BA}$) of a crotonaldehyde concentration $C_{CR}$ (ppm by mass) to a butyl acetate concentration $C_{BA}$ (ppm by mass) in the first acetic acid stream, the ratio ($C_{CR}/C_{ECR}$) of a crotonaldehyde concentration $C_{CR}$ (ppm by mass) to a 2-ethylcrotonaldehyde concentration $C_{ECR}$ (ppm by mass) in an acetic acid-rich stream resulting from further purification of the first acetic acid stream, and the ratio ($C_{CR}/C_{BA}$) of a crotonaldehyde concentration $C_{CR}$ (ppm by mass) to a butyl acetate concentration $C_{BA}$ (ppm by mass) in the acetic acid-rich stream resulting from further purification of the first acetic acid stream, where the conditions (i) to (iii) are as follows:

(i) a reflux ratio at the distillation column is 0.01 or more;

(ii) at the distillation column, the ratio of a crotonaldehyde concentration (ppm by mass) in a distillate to a crotonaldehyde concentration (ppm by mass) in a charge liquid is less than 1; and (iii) at the distillation column, the ratio of a crotonaldehyde concentration (ppm by mass) in bottoms to a crotonaldehyde concentration (ppm by mass) in the charge liquid is greater than 1.

The second acetic acid production method according to the present invention gives an acetic acid product that yields a better potassium permanganate test result, by configurations as follows. Specifically, the second acetic acid production method includes a carbonylation step, a separation step, a recycling step, and a crotonaldehyde-removing step. In the carbonylation step, methanol is carbonylated (reacted) with carbon monoxide in a reactor in the presence of a catalytic system, acetic acid, methyl acetate, and water, to give acetic acid in a reaction mixture, where the catalytic system includes a metal catalyst and methyl iodide. In the separation step, the reaction mixture from the carbonylation step is separated, using at least one selected from evaporators and distillation columns, to give a stream including the metal catalyst, an acetic acid stream rich in acetic acid, and a stream rich in light ends as compared with the acetic acid stream. In the recycling step, at least a part of the light ends-rich stream is recycled to the reactor. In the crotonaldehyde-removing step, at least a part of the remainder of the light ends-rich stream is treated in a distillation column to separate and remove crotonaldehyde. The separation step includes a first separation step and a second separation step. In the first separation step, the reaction mixture is separated using the first distillation column into a first acetic acid stream rich in acetic acid, and an overhead stream rich in light ends as compared with the first acetic acid stream, and the overhead stream is condensed to give a condensate. In the second separation step, the first acetic acid stream is subjected to distillation in a second distillation column to further purify acetic acid. The reflux ratio at the first distillation column is controlled as follows. Provided that the condensate is liquid-liquid separated into an aqueous phase and an organic phase, the reflux ratio for the aqueous phase is 2 or more when the aqueous phase alone is refluxed to the first distillation column; the reflux ratio for the organic phase is 1 or more when the organic phase alone is refluxed to the first distillation column; and the total reflux ratio for the aqueous phase and the organic phase is 1.5 or more when both the aqueous phase and the organic phase are refluxed to the first distillation column.

Alternatively, provided that the condensate is refluxed to the first distillation column without liquid-liquid separation, the reflux ratio for the condensate is 1.5 or more. In addition, the distillation column is operated in the crotonaldehyde-removing step so as to meet at least one of conditions (i) to (iii) mentioned later. A crotonaldehyde concentration in the first acetic acid stream is controlled to 2.2 ppm by mass or less, and/or a reflux ratio at the second distillation column is controlled to 0.1 or more, and at least one ratio is lowered, where the at least one ratio is selected from the group consisting of the ratio ($C_{CR}/C_{ECR}$) of a crotonaldehyde concentration $C_{CR}$ (ppm by mass) to a 2-ethylcrotonaldehyde concentration $C_{ECR}$ (ppm by mass) in the first acetic acid stream, the ratio ($C_{CR}/C_{BA}$) of a crotonaldehyde concentration $C_{CR}$ (ppm by mass) to a butyl acetate concentration $C_{BA}$ (ppm by mass) in the first acetic acid stream, the ratio ($C_{CR}/C_{ECR}$) of a crotonaldehyde concentration $C_{CR}$ (ppm by mass) to a 2-ethylcrotonaldehyde concentration $C_{ECR}$ (ppm by mass) in an acetic acid-rich stream from the second separation step, and the ratio ($C_{CR}/C_{BA}$) of a crotonaldehyde concentration $C_{CR}$ (ppm by mass) to a butyl acetate concentration $C_{BA}$ (ppm by mass) in the acetic acid-rich stream from the second separation step. The conditions (i) to (iii) are as follows:

(i) a reflux ratio at the distillation column is 0.01 or more;

(ii) at the distillation column, the ratio of a crotonaldehyde concentration (ppm by mass) in a distillate to a crotonaldehyde concentration (ppm by mass) in a charge liquid is less than 1; and (iii) at the distillation column, the ratio of a crotonaldehyde concentration (ppm by mass) in bottoms to a crotonaldehyde concentration (ppm by mass) in the charge liquid is greater than 1.

In the first and second acetic acid production methods according to the present invention (hereinafter these are also generically referred to as "acetic acid production methods according to the present invention"), the catalytic system may further include an ionic iodide. The ionic iodide functions as a promoter.

The separation step in the acetic acid production methods according to the present invention preferably includes, for example, an evaporation step, a light ends-removing step, and a dehydration step, where the light ends-removing step serves as the first separation step, and the dehydration step serves as the second separation step. In the evaporation step, the reaction mixture from the carbonylation step is separated into a vapor stream and a residue stream (residual liquid stream), using an evaporator. In the light ends-removing step, the vapor stream is separated by distillation into the first acetic acid stream rich in acetic acid, and a stream (such as an overhead stream, concretely exemplified by a first overhead stream) rich in light ends as compared with the first acetic acid stream. In the dehydration step, the first acetic acid stream is separated by distillation into a water-rich overhead stream (second overhead stream), and a second acetic acid stream rich in acetic acid as compared with the first acetic acid stream. The distillation column for use in the light ends-removing step is also referred to as a "first distillation column" (light ends column), and the distillation column for use in the dehydration step is also referred to as a "second distillation column" (dehydration column).

The separation step may include an evaporation-light ends-removing step, instead of the evaporation step and the light ends-removing step. The evaporation-light ends-removing step is the step of separating the reaction mixture resulting from the carbonylation step into a stream including the metal catalyst, a light ends-rich stream (such as an overhead stream), and the first acetic acid stream rich in acetic acid. The separation step may include a so-called light ends-water-removing step, instead of the light ends-removing step and the dehydration step. The light ends-water-removing step is a light ends-removing step that also functions as a dehydration step. Specifically, the light ends-water-removing step is the step of separating the vapor stream by distillation into a light ends-rich stream (such as an overhead stream), and an acetic acid stream that has been dehydrated to a water concentration equivalent to that in the second acetic acid stream. Accordingly, the evaporation-light ends-removing step may be a step that also functions as s dehydration step (evaporation-light ends-water-removing step). The acetic acid streams rich in acetic acid from the light ends-water-removing step and the evaporation-light ends-water-removing step each correspond to the second acetic acid stream. The distillation columns for use in the evaporation-light ends-removing step, the light ends-water-removing step, and the evaporation-light ends-water-removing step each correspond to the first distillation column.

The separation step may include an evaporation step and a light ends-removing step, where the light ends-removing step serves as the first separation step. In the evaporation step, the reaction mixture resulting from the carbonylation step is separated into a vapor stream and a residue stream, using an evaporator. In the light ends-removing step, the vapor stream is separated, using the first distillation column, into a first overhead stream rich in at least one light end selected from methyl iodide and acetaldehyde, and a first acetic acid stream rich in acetic acid, and the first overhead stream is condensed.

The separation step may include a dehydration step as the second separation step. In the dehydration step, the first acetic acid stream is further separated, using the second distillation column, into a second overhead stream rich in water, and a second acetic acid stream rich in acetic acid as compared with the first acetic acid stream.

The light ends-removing step may include liquid-liquid separation of a condensate derived from the first overhead stream, to give an aqueous phase and an organic phase.

In the recycling step, the light ends-rich stream is condensed to give a condensate, and at least a part of the condensate is recycled to the reactor. The recycling step may include recycling of at least a part of at least one liquid to the reactor, where the at least one liquid is selected from the group consisting of the condensate resulting from condensation of the first overhead stream, the aqueous phase resulting from liquid-liquid separation of the condensate, the organic phase resulting from liquid-liquid separation of the condensate, and the second overhead stream.

In the crotonaldehyde-removing step, crotonaldehyde is separated and removed from at least a part of the remainder of the light ends-rich stream by a treatment in a distillation column. The crotonaldehyde-removing step may include a step that may include separating and removal of crotonaldehyde from at least a part of at least one liquid by a treatment in a distillation column, where the at least one liquid is selected from the group consisting of the condensate resulting from condensation of the first overhead stream, the aqueous phase resulting from liquid-liquid separation of the condensate, and the organic phase resulting from liquid-liquid separation of the condensate.

The acetic acid production methods according to the present invention may further include an acetaldehyde-removing step. This step is the step of removing acetaldehyde from at least a part of at least one liquid by distillation, where the at least one liquid is selected from the group consisting of the condensate, the aqueous phase resulting from liquid-liquid separation of the condensate, and the organic phase resulting from liquid-liquid separation of the condensate. In this case, at least a part of a residue may be recycled to the reactor, where the residue is a residual liquid after separation and removal of acetaldehyde from at least a part of at least one liquid selected from the group consisting of the condensate, the aqueous phase, and the organic phase. The methods, when including the acetaldehyde-removing step, enable efficient separation and removal of acetaldehyde which is formed in the reaction system. The recycling of the residue after separation and removal of acetaldehyde to the reactor enables effective usage of methyl iodide and other useful components.

Control of the crotonaldehyde concentration in the first acetic acid stream from the separation step to a low level of 2.2 ppm by mass or less can lower the crotonaldehyde concentration in the second acetic acid stream, which results from separation and removal of water in the dehydration step, typically to 2.0 ppm by mass or less, and allows the second acetic acid stream to yield a better potassium permanganate test result. This can therefore downsize or eliminate acetaldehyde-removing facilities and ozone treatment facilities, which have been conventionally used for yielding better potassium permanganate test results. Such acetic acid yielding a good potassium permanganate test result can be obtained simply through the light ends column and the dehydration column. This can downsize or eliminate a downstream heavy ends column and a product column (finishing column). The first acetic acid stream has a crotonaldehyde concentration of preferably 2.0 ppm by mass or less, more preferably 1.8 ppm by mass or less, furthermore preferably 1.5 ppm by mass or less, particularly preferably 1.2 ppm by mass or less (for example, 1.0 ppm by mass or less, or 0.8 ppm by mass or less, and especially preferably 0.5 ppm by mass or less). Assume that the reflux ratio at the second distillation column (dehydration column) is controlled to 0.1 or more (for example, 0.3 or more, and preferably 0.32 or more). In this case, the crotonaldehyde concentration in the first acetic acid stream may be typically 5 ppm by mass or less (in particular, 2.5 ppm by mass or less), but preferably falls within the range.

In a preferred embodiment, the first acetic acid stream has a crotonaldehyde concentration of typically 1.3 ppm by mass or less, preferably 1.0 ppm by mass or less, more preferably 0.85 ppm by mass or less, and particularly preferably 0.5 ppm by mass or less (for example, 0.25 ppm by mass or less). Control of the crotonaldehyde concentration in the first acetic acid stream to 1.3 ppm by mass or less allows the second acetic acid stream to have a significantly lower crotonaldehyde concentration and to yield a significantly better potassium permanganate test result. The lower limit of the crotonaldehyde concentration in the first acetic acid stream may be 0 ppm by mass, or may typically be 0.01 ppm by mass (or 0.10 ppm by mass).

A non-limiting example of the way to lower the crotonaldehyde concentration in the first acetic acid stream is increase in hydrogen partial pressure in the reactor. The increase in hydrogen partial pressure in the reactor causes crotonaldehyde to be hydrogenated and converted to butanol, and thereby allows the liquid reaction mixture (a liquid phase of the reaction mixture; a reaction medium) to have a lower crotonaldehyde concentration. This lowers the crotonaldehyde concentration in the liquid fed to the first distillation column, and, consequently, lowers the crotonaldehyde concentration in the first acetic acid stream resulting from light ends removal in the first distillation column. The hydrogen partial pressure in the reactor is typically 0.001 MPa (absolute pressure) or more (for example, 0.005 MPa or more), preferably 0.01 MPa (absolute pressure) or more (for example, 0.015 MPa or more), more preferably 0.02 MPa (absolute pressure) or more, furthermore preferably 0.04 MPa (absolute pressure) or more, and particularly preferably 0.06 MPa (absolute pressure) or more (for example, 0.07 MPa (absolute pressure) or more). The upper limit of the hydrogen partial pressure in the reactor is typically 0.5 MPa (absolute pressure) (in particular, 0.2 MPa (absolute pressure)).

Another non-limiting example of the way to lower the crotonaldehyde concentration in the first acetic acid stream is increase in reflux ratio at the light ends column. With an increased reflux ratio at the light ends column, crotonaldehyde is more concentrated at the column top of the distillation column, because crotonaldehyde (boiling point: 104° C.) has a lower boiling point as compared with acetic acid (boiling point: 117° C.). This allows the first acetic acid stream, which is obtained as a side stream or a bottoms stream, to have a lower crotonaldehyde concentration, and results in production of an acetic acid product that yields a good potassium permanganate test result. Assume that the condensate (at least one of the aqueous phase and the organic phase) derived from the first overhead stream is recycled to the reactor, where crotonaldehyde is concentrated in the condensate by the increase in reflux ratio at the light ends column. The crotonaldehyde in the reactor reacts with acetaldehyde to form 2-ethylcrotonaldehyde. In addition, the crotonaldehyde in the reactor also reacts with hydrogen to form butanol, and the butanol in turn reacts with acetic acid to form butyl acetate. As compared with crotonaldehyde, 2-ethylcrotonaldehyde less affects the potassium permanganate test result, and butyl acetate does little or not affect the potassium permanganate test result. Accordingly, acetic acid tends to have still higher quality. At an increased reflux ratio at the light ends column, 2-ethylcrotonaldehyde and butyl acetate tend to be concentrated in sidecuts at levels lower than the feeding level of the charge liquid to the light ends column, and in bottoms, because 2-ethylcrotonaldehyde and butyl acetate have boiling points respectively of 137° C. and 126° C., which are higher than the boiling point (117° C.) of acetic acid.

The reflux ratio at the light ends column is controlled as follows. Assume that the aqueous phase alone of the condensate derived from the first overhead stream is refluxed to the light ends column. In this case, the reflux ratio for the aqueous phase is controlled to typically 2 or more, preferably 3 or more, more preferably 4 or more, furthermore preferably 8 or more, and particularly preferably 10 or more, where the reflux ratio for the aqueous phase is the ratio of the aqueous phase reflux amount to the aqueous phase distillate amount. Assume that the organic phase alone of the condensate derived from the first overhead stream is refluxed to the light ends column. In this case, the reflux ratio for the organic phase is controlled to typically 1 or more, preferably 1.5 or more, more preferably 2 or more, furthermore preferably 4 or more, and particularly preferably 5 or more, where the reflux ratio for the organic phase is the ratio of the organic phase reflux amount to the organic phase distillate amount. Assume that both the aqueous phase and the organic phase of the condensate derived from the first overhead stream are refluxed to the light ends column. In this case, the total reflux ratio for the aqueous phase and the organic phase is controlled to typically 1.5 or more, preferably 2.3 or more, more preferably 3 or more, furthermore preferably 6 or more, and particularly preferably 7.5 or more, where the total reflux ratio is the ratio of the totality of reflux amounts of the aqueous phase and the organic phase to the totality of the distillate amounts of the aqueous phase and the organic phase. When the aqueous phase is refluxed to the light ends column, the reflux ratio for the aqueous phase is preferably 2 or more, more preferably 3 or more, furthermore preferably 5 or more, particularly preferably 8 or more, and especially preferably 12 or more, where the reflux ratio herein is the ratio of the aqueous phase reflux amount to the aqueous phase distillate amount. Assume that the condensate is refluxed to the light ends column without liquid-liquid separation. In this case, the reflux ratio for the condensate is 1.5 or more, preferably 2.3 or more, more preferably 3.5 or more, furthermore preferably 6 or more, and particularly preferably 8.5 or more. A non-limiting example of the case where the condensate is refluxed without liquid-liquid separation is the case where the condensate is in a homogeneous state and is not separated into different liquids. When the reflux ratio at the dehydration column is controlled to 0.1 or more as described above, the reflux ratio at the light ends column may be typically 0.5 or more, regardless of which of the upper phase and the lower phase is refluxed. In any case, the upper limit of the reflux ratio at the light ends column may be typically 3000 (in particular, 1000), or may be 100 (in particular, 30).

As used herein, the term "reflux ratio" at a distillation column refers to "the ratio of the reflux amount to the distillate amount", where the term "reflux amount" refers to, of an overhead liquid from the distillation column, the amount of a liquid refluxed to the distillation column; and the term "distillate amount" refers to, of the overhead liquid from the distillation column, the amount of a liquid that is not refluxed to the distillation column, but is discharged from the distillation column.

Still another non-limiting example of the way to lower the crotonaldehyde concentration in the first acetic acid stream is decrease in concentration of acetaldehyde present in the liquid reaction mixture (reaction medium) in the reactor. The decrease in acetaldehyde concentration in the liquid reaction mixture in the reactor restrains the formation of crotonaldehyde by aldol condensation of acetaldehyde. This allows the liquid to be fed to the first distillation column to have a lower crotonaldehyde concentration, and, consequently, allows the first acetic acid stream to also have a lower crotonaldehyde concentration, where the first acetic acid stream results from light ends removal in the first distillation column. The liquid reaction mixture in the reactor has an acetaldehyde concentration of typically 500 ppm by mass or less, preferably 450 ppm by mass or less, more preferably 400 ppm by mass or less, furthermore preferably 350 ppm by mass or less, and particularly preferably 300 ppm by mass or less (for example, 250 ppm by mass or less). The acetaldehyde concentration in the liquid reaction mixture in the reactor can be lowered typically by increasing the carbon monoxide (CO) partial pressure in the reactor, and/or by increasing the methyl acetate concentration in the liquid reaction mixture in the reactor. The acetaldehyde concentration in the liquid reaction mixture in the reactor can be lowered typically by increasing the feeding amount to the acetaldehyde-removing step and decreasing the recycling amount to the reactor, of the condensate (the aqueous phase and/or the organic phase) derived from the first overhead stream from the first distillation column.

The acetic acid production methods may include a dehydration step as a second separation step. In the dehydration step, the first acetic acid stream is separated, through a second distillation column, into a second overhead stream rich in water, and a second acetic acid stream rich in acetic acid as compared with the first acetic acid stream. The dehydration of the first acetic acid stream in the second distillation column can give the second acetic acid stream having a lower water content, where the second acetic acid stream is obtained as bottoms or a sidecut liquid respectively from the column bottom or an intermediate portion in the column. The second acetic acid stream can serve as an acetic acid product as intact or after further purification as needed.

The reflux ratio at the second distillation column (dehydration column) is typically 0.1 or more, preferably 0.3 or more, more preferably 0.32 or more, furthermore preferably 1.0 or more, particularly preferably 5.0 or more, and especially preferably 10 or more (for example, 12 or more). The upper limit of the reflux ratio at the second distillation column may be typically about 3000 (or about 1000), or about 200 (or about 100). The increase in reflux ratio at the second distillation column up to 0.1 or more allows the second acetic acid stream to have a higher purity and to yield a better potassium permanganate test result.

The control of the reflux ratio at the dehydration column to 0.1 or more allows crotonaldehyde flowing into the dehydration column to be concentrated at the column top, and allows the second acetic acid stream to have a significantly lowered crotonaldehyde concentration, where the second acetic acid stream is obtained as a side stream or a bottoms stream. This is because crotonaldehyde has a lower boiling point as compared with acetic acid as described above. In addition, the recycling of the second overhead stream, in which crotonaldehyde is concentrated, from the dehydration column top to the reactor contributes to still higher quality of acetic acid, because crotonaldehyde in the reactor is converted to less harmful 2-ethylcrotonaldehyde, and to harmless butyl acetate, as described above.

In a preferred embodiment, the reflux ratio at the dehydration column is typically 0.1 or more, preferably 0.3 or more (for example, 0.32 or more), more preferably 0.4 or more, furthermore preferably 1 or more, and particularly preferably 2 or more. When the crotonaldehyde concentration in the first acetic acid stream is controlled to 2.2 ppm by mass or less, the reflux ratio at the dehydration column may be typically 0.1 or more (in particular, 0.3 or more, and for example, 0.32 or more). The upper limit of the reflux ratio at the dehydration column is typically 3000 (in particular, 1000), and may be about 100 or about 10. The increase in reflux ratio at the dehydration column up to 0.1 or more (preferably 0.3 or more, and for example 0.32 or more) allows the second acetic acid stream to have a higher purity and to yield a better potassium permanganate test result.

The methods according to the present invention increase the reflux ratio at the first distillation column to thereby allow crotonaldehyde to be concentrated at the column top, and include the crotonaldehyde-removing step, in which at least a part of the light ends column overhead condensate containing concentrated crotonaldehyde (hereinafter also simply referred to as a "condensate") is treated in a distillation column to separate and remove crotonaldehyde therefrom. In the crotonaldehyde-removing step, the condensate may be liquid-liquid separated into an aqueous phase and an organic phase, and at least a part of at least one of the aqueous phase and the organic phase may be recycled to the reactor. The concentration (enrichment) of crotonaldehyde at the column top allows the first acetic acid stream to have a lower crotonaldehyde concentration, and this results in production of an acetic acid product that yields a good potassium permanganate test result. The crotonaldehyde recycled to the reactor undergoes reactions: crotonaldehyde+acetaldehyde→2-ethylcrotonaldehyde; crotonaldehyde+hydrogen→butyl alcohol; butyl alcohol+acetic acid-→butyl acetate, and is converted to 2-ethylcrotonaldehyde, which less affects the potassium permanganate test result, and to butyl acetate, which does little or not affect the potassium permanganate test result. This can give an acetic acid product that has better quality. In the present invention, at least a part of at least one liquid is treated in the crotonaldehyde-removing column, where the at least one liquid is selected from the group consisting of the condensate containing concentrated crotonaldehyde, the aqueous phase resulting from liquid-liquid separation of the condensate, and the organic phase resulting from liquid-liquid separation of the condensate. Thus, when crotonaldehyde, which has a high boiling point of 104° C., is drawn from the column bottom, together with acetic acid and alkanes as high-boiling compounds, and discharged out of the system, the acetic acid product can yield a still better potassium permanganate test result. The overhead condensate from the crotonaldehyde-removing column includes useful components (such as methyl iodide and methyl acetate) and can be recycled to a decanter in which the light ends column overhead condensate is stored, and/or to the reactor.

The reflux ratio at the first distillation column is controlled as follows. Provided that the condensate is liquid-liquid separated into an aqueous phase and an organic phase. When the aqueous phase is refluxed to the first distillation column, the reflux ratio for the aqueous phase is 2 or more, preferably 3 or more, more preferably 5 or more, furthermore preferably 8 or more, and particularly preferably 12 or more, where the reflux ratio for the aqueous phase is the ratio of the aqueous phase reflux amount to the aqueous phase distillate amount. When the organic phase alone is refluxed to the first distillation column, the reflux ratio for the organic phase is 1 or more, preferably 1.5 or more, more preferably 2 or more, furthermore preferably 4 or more, and particularly preferably 5 or more, where the reflux ratio for the organic phase is the ratio of the organic phase reflux amount to the organic phase distillate amount. When both the aqueous phase and organic phase are refluxed to the first distillation column, the total reflux ratio for the aqueous phase and the organic phase is 1.5 or more, preferably 2.3 or more, more preferably 3.5 or more, furthermore preferably 6 or more, and particularly preferably 8.5 or more, where the total reflux ratio is the ratio of the totality of reflux amounts of the aqueous phase and the organic phase to the totality of distillate amounts of the aqueous phase and the organic phase. When the aqueous phase is refluxed to the first distillation column, the reflux ratio for the aqueous phase is preferably 2 or more, more preferably 3 or more, furthermore preferably 5 or more, particularly preferably 8 or more, and especially preferably 12 or more, where the reflux ratio for the aqueous phase is the ratio of the aqueous phase reflux amount to the aqueous phase distillate amount. When the condensate is refluxed to the first distillation column without liquid-liquid separation, the reflux ratio for the condensate is 1.5 or more, preferably 2.3 or more, more preferably 3.5 or more, furthermore preferably 6 or more, and particularly preferably 8.5 or more. A non-limiting example of the case where the condensate is refluxed without liquid-liquid separation is the case where the condensate is in a homogeneous state and is not separated into different liquids. The upper limit of the reflux ratio at the first distillation column, in any case, may be typically 3000 (in particular, 1000), or may be 100 (in particular, 30).

In the condition (i), the reflux ratio at the crotonaldehyde-removing column is preferably 0.05 or more, more preferably 0.5 or more, furthermore preferably 5 or more, and particularly preferably 20 or more (for example, 30 or more). The upper limit of the reflux ratio at the crotonaldehyde-removing column is typically 1000. In the condition (ii), at the crotonaldehyde-removing column (distillation column), the ratio of a crotonaldehyde concentration (ppm by mass) in the distillate to a crotonaldehyde concentration (ppm by mass) in the charge liquid is preferably 0.95 or less, more preferably 0.80 or less, furthermore preferably 0.70 or less, and particularly preferably 0.60 or less (for example, 0.50 or less, especially preferably 0.30 or less, and particularly 0.20 or less). In the condition (iii), at the crotonaldehyde-removing column, the ratio of a crotonaldehyde concentration (ppm by mass) in the bottoms to a crotonaldehyde concentration (ppm by mass) in the charge liquid is preferably 1.2 or more, more preferably 1.5 or more, furthermore preferably 2.0 or more, particularly preferably 3.0 or more (for example, 4.0 or more, especially preferably 5.0 or more), and still especially preferably 10 or more (for example, 20 or more). The operation of the crotonaldehyde-removing column so as to meet at least one of the conditions (i) to (iii) allows crotonaldehyde to be concentrated at the column bottom, and to be discharged out of the system as bottoms together with alkanes and other high-boiling impurities and acetic acid.

According to the present invention, the crotonaldehyde concentration in the first acetic acid stream is lowered not by decreasing 2-ethylcrotonaldehyde, butanol, and butyl acetate, but by facilitating or enhancing the conversion of crotonaldehyde to 2-ethylcrotonaldehyde and conversion of crotonaldehyde through butanol to butyl acetate, typically by the procedure as above. Thus, the first acetic acid stream is allowed to have a lower ratio ($C_{CR}/C_{ECR}$) of a crotonaldehyde concentration $C_{CR}$ (ppm by mass) to a 2-ethylcrotonaldehyde concentration $C_{ECR}$ (ppm by mass), and/or a lower ratio ($C_{CR}/C_{BA}$) of a crotonaldehyde concentration $C_{CR}$ (ppm by mass) to a butyl acetate concentration $C_{BA}$ (ppm by mass). This can give an acetic acid product that yields a better potassium permanganate test result.

The first acetic acid stream in the present invention has a 2-ethylcrotonaldehyde concentration of typically 3.0 ppm by mass or less, preferably 2.0 ppm by mass or less, more preferably 1.0 ppm by mass or less, and furthermore preferably 0.8 ppm by mass or less (for example, 0.5 ppm by mass or less).

In a preferred embodiment, the first acetic acid stream has a 2-ethylcrotonaldehyde concentration of typically 1.0 ppm by mass or less, and preferably 0.50 ppm by mass or less. The control of the 2-ethylcrotonaldehyde concentration in the first acetic acid stream to 1.0 ppm by mass or less allows the second acetic acid stream to yield a still better potassium permanganate test result. The lower limit of the 2-ethylcrotonaldehyde concentration in the first acetic acid stream may be typically 0 ppm by mass, or 0.01 ppm by mass (or 0.10 ppm by mass).

The first acetic acid stream has a ratio ($C_{CR}/C_{ECR}$) of the crotonaldehyde concentration $C_{CR}$ (ppm by mass) to the 2-ethylcrotonaldehyde concentration $C_{ECR}$ (ppm by mass) of typically 50 or less, preferably 35 or less, more preferably 25 or less, furthermore preferably 20 or less, and particularly preferably 15 or less. The lower limit of the ratio may be typically 0.01, 0.05, 0.1, 0.3, or 0.5.

The first acetic acid stream has a butyl acetate concentration of typically 15 ppm by mass or less, preferably 12 ppm by mass or less, more preferably 10 ppm by mass or less, and furthermore preferably 8 ppm by mass or less.

In a preferred embodiment, the first acetic acid stream has a butyl acetate concentration of typically 15 ppm by mass or less, preferably 10 ppm by mass or less, more preferably 8 ppm by mass or less, and particularly preferably 5 ppm by mass or less (for example, 3 ppm by mass or less). The control of the butyl acetate concentration in the first acetic acid stream to 15 ppm by mass or less allows the second acetic acid stream to have a higher purity. The lower limit of the butyl acetate concentration in the first acetic acid stream may be typically 0 ppm by mass, or 0.1 ppm by mass (for example, 0.3 ppm by mass, or 1.0 ppm by mass).

The first acetic acid stream has a ratio ($C_{CR}/C_{BA}$) of the crotonaldehyde concentration $C_{CR}$ (ppm by mass) to the butyl acetate concentration $C_{BA}$ (ppm by mass) of typically 2.0 or less, preferably 1.5 or less, more preferably 1.0 or less, and furthermore preferably 0.6 or less. The lower limit of the ratio may be typically 0.001, 0.01, 0.02, 0.05, or 0.1.

The present invention can also give an acetic acid product that yields a better potassium permanganate test result, by lowering at least one ratio in the second acetic acid stream or another acetic acid-rich stream resulting from further purification of the first acetic acid stream, where the at least one ratio is selected from the ratio ($C_{CR}/C_{ECR}$) of a crotonaldehyde concentration $C_{CR}$ (ppm by mass) to a 2-ethylcrotonaldehyde concentration $C_{ECR}$ (ppm by mass), and the ratio ($C_{CR}/C_{BA}$) of a crotonaldehyde concentration $C_{CR}$ (ppm by mass) to a butyl acetate concentration $C_{BA}$ (ppm by mass). The ratios in the acetic acid-rich stream can be lowered typically by lowering the ratio ($C_{CR}/C_{ECR}$) of the crotonaldehyde concentration $C_{CR}$ (ppm by mass) to the 2-ethylcrotonaldehyde concentration $C_{ECR}$ (ppm by mass) in the first acetic acid stream; by lowering the ratio ($C_{CR}/C_{BA}$) of the crotonaldehyde concentration $C_{CR}$ (ppm by mass) to the butyl acetate concentration $C_{BA}$ (ppm by mass) in the first acetic acid stream; and/or by increasing the reflux ratio at a distillation column in the dehydration step or another step of further purifying the first acetic acid stream.

In the present invention, an acetic acid-rich stream (such as the second acetic acid stream) resulting from further purification of the first acetic acid stream has a crotonaldehyde concentration of typically 2.0 ppm by mass or less, preferably 1.8 ppm by mass or less, more preferably 1.5 ppm by mass or less, furthermore preferably 1.2 ppm by mass or less, and particularly preferably 0.7 ppm by mass or less (for example, 0.5 ppm by mass or less).

In a preferred embodiment, the acetic acid-rich stream (such as the second acetic acid stream) resulting from further purification of the first acetic acid stream has a crotonaldehyde concentration of typically 0.98 ppm by mass or less, preferably 0.80 ppm by mass or less, more preferably 0.50 ppm by mass or less, and furthermore preferably 0.30 ppm by mass or less. The control of the crotonaldehyde concentration to 0.98 ppm by mass or less can significantly lower the crotonaldehyde concentration in the acetic acid-rich stream (such as the second acetic acid stream) resulting from further purification of the first acetic acid stream, and allows the acetic acid-rich stream resulting from further purification of the first acetic acid stream to yield a significantly better potassium permanganate test result. The lower limit of the crotonaldehyde concentration may be 0 ppm by mass, or may be typically 0.01 ppm by mass (or 0.10 ppm by mass).

The acetic acid-rich stream (such as the second acetic acid stream) resulting from further purification of the first acetic acid stream has a 2-ethylcrotonaldehyde concentration of typically 3.0 ppm by mass or less, preferably 2.0 ppm by mass or less, more preferably 1.0 ppm by mass or less, and furthermore preferably 0.8 ppm by mass or less (for example, 0.5 ppm by mass or less).

In a preferred embodiment, the acetic acid-rich stream (such as the second acetic acid stream) resulting from further purification of the first acetic acid stream has a 2-ethylcrotonaldehyde concentration of typically 1.00 ppm by mass or less, preferably 0.50 ppm by mass or less, more preferably 0.30 ppm by mass or less, and furthermore preferably 0.20 ppm by mass or less. The control of the 2-ethylcrotonaldehyde concentration to 1.0 ppm by mass or less allows the acetic acid-rich stream resulting from further purification of the first acetic acid stream to yield a still better potassium permanganate test result. The lower limit of the 2-ethylcrotonaldehyde concentration may be typically 0 ppm by mass, or 0.01 ppm by mass (for example, 0.10 ppm by mass).

The acetic acid-rich stream (such as the second acetic acid stream) resulting from further purification of the first acetic acid stream has a ratio ($C_{CR}/C_{ECR}$) of the crotonaldehyde concentration $C_{CR}$ (ppm by mass) to the 2-ethylcrotonaldehyde concentration $C_{ECR}$ (ppm by mass) of typically 50 or less, preferably 35 or less, more preferably 25 or less, furthermore preferably 20 or less, and particularly preferably 15 or less. The lower limit of the ratio may be typically 0.01, 0.05, 0.1, 0.3, or 0.5.

The acetic acid-rich stream (such as the second acetic acid stream) resulting from further purification of the first acetic acid stream has a butyl acetate concentration of typically 15 ppm by mass or less, preferably 12 ppm by mass or less, more preferably 10 ppm by mass or less, and furthermore preferably 8 ppm by mass or less.

In a preferred embodiment, the acetic acid-rich stream (such as the second acetic acid stream) resulting from further purification of the first acetic acid stream has a butyl acetate concentration of typically 15 ppm by mass or less, preferably 10 ppm by mass or less, more preferably 8 ppm by mass or less, and particularly preferably 5 ppm by mass or less (for example, 3 ppm by mass or less). The control of the butyl acetate concentration to 15 ppm by mass or less allows the acetic acid-rich stream resulting from further purification of the first acetic acid stream to have a higher purity. The lower limit of the butyl acetate concentration may be typically 0 ppm by mass, or 0.1 ppm by mass (for example, 0.3 ppm by mass or 1.0 ppm by mass).

The acetic acid-rich stream (such as the second acetic acid stream) resulting from further purification of the first acetic acid stream has a ratio ($C_{CR}/C_{BA}$) of the crotonaldehyde concentration $C_{CR}$ (ppm by mass) to the butyl acetate concentration $C_{BA}$ (ppm by mass) of typically 2.0 or less, preferably 1.5 or less, more preferably 1.0 or less, and furthermore preferably 0.6 or less. The lower limit of the ratio may be typically 0.001, 0.01, 0.02, 0.05, or 0.1.

The acetic acid-rich stream (such as the second acetic acid stream) resulting from further purification of the first acetic acid stream yields a potassium permanganate test result of preferably longer than 50 minutes, more preferably 60 minutes or longer, furthermore preferably 100 minutes or longer, particularly preferably 120 minutes or longer (for example, 180 minutes or longer, especially preferably 240 minutes or longer, and particularly 360 minutes or longer). The potassium permanganate test result is specified also in Japanese Industrial Standards (JIS) as one of indices for quality control of acetic acid products. As described above, the potassium permanganate test result can be said as a preferred index that is industrially widely used for quality control of acetic acid products and can be said as a preferred index that enables easy examination of the purity of acetic acid products. As used herein, the "potassium permanganate test result" refers to a value measured in accordance with the procedure of visual colorimetry prescribed in JIS K 1351: 1993.

The vapor stream to be fed to the first distillation column has a crotonaldehyde concentration of typically 0 to 5.0 ppm by mass (for example, 0.01 to 4.0 ppm by mass), preferably 0.1 to 3.0 ppm by mass, and furthermore preferably 0.2 to 2.0 ppm by mass. The vapor stream has a 2-ethylcrotonaldehyde concentration of typically 0 to 3.0 ppm by mass (for example, 0.01 to 2.5 ppm by mass), preferably 0.02 to 2.0 ppm by mass, and furthermore preferably 0.03 to 0.8 ppm by mass. The vapor stream has a butyl acetate concentration of typically 0.1 to 13.0 ppm by mass, preferably 0.2 to 12.0 ppm by mass, and furthermore preferably 0.3 to 9.0 ppm by mass.

The charge liquid fed to the distillation column in the crotonaldehyde-removing step has a crotonaldehyde concentration of generally 0.01 to 50 ppm by mass (for example, 0.1 to 50 ppm by mass), preferably 0.3 to 30 ppm by mass, more preferably 0.5 to 10 ppm by mass, and furthermore preferably 0.8 to 7.0 ppm by mass (for example, 1.0 to 5.0 ppm by mass).

In the crotonaldehyde-removing step, the distillation column is preferably operated so as to meet all the conditions (i) to (iii). The operation of the crotonaldehyde-removing column (distillation column) so as to meet all the conditions (i) to (iii) enables removal of crotonaldehyde with significantly higher efficiency and gives an acetic acid product that yields a significantly better potassium permanganate test result.

The distillation treatment in the crotonaldehyde-removing step may be performed batchwise. Energy cost can be saved by performing such a batchwise distillation treatment at the time point(s) when crotonaldehyde accumulates to some extent in at least a part of the remainder of at least one liquid selected from the group consisting of the condensate, the aqueous phase, and the organic phase.

The distillation column in the crotonaldehyde-removing step is operated at a throughput of typically 0.0001 to 50 parts by mass, preferably 0.001 to 30 parts by mass (for example, 0.01 to 10 parts by mass, and, in particular, 0.1 to 5 parts by mass), per 100 parts by mass of the amount of the vapor stream fed to the first distillation column.

Hereinafter one embodiment of the present invention will be illustrated. FIG. 1 is an acetic acid production flow chart (methanol carbonylation process) according to an embodiment of the present invention. Acetic acid production equipment according to this acetic acid production flow includes a reactor 1, an evaporator 2, a distillation column 3, a decanter 4, a distillation column 5, a distillation column 6, an ion exchange resin column 7, a scrubber system 8, an acetaldehyde removing system 9, a distillation column 10, condensers 1a, 2a, 3a, 5a, 6a, and 10a, a heat exchanger 2b, reboilers 3b, 5b, 6b, and 10b, lines 11 to 56, and 58 to 63, and a pump 57. The equipment is configured so as to be capable of continuously producing acetic acid. An acetic acid production method according to the embodiment performs a reaction step, an evaporation step (flash step), a first distillation step, a second distillation step, a third distillation step, a crotonaldehyde-removing step, and an adsorptive removing step respectively in the reactor 1, the evaporator 2, the distillation column 3, the distillation column 5, the distillation column 6, the distillation column 10, and the ion exchange resin column 7. The first distillation step and the second distillation step correspond respectively to the first separation step and the second separation step. The first distillation step, the second distillation step, and the third distillation step are also referred respectively to a light ends-removing step, a dehydration step, and a heavy ends-removing step. In the present invention, steps to be performed are not limited to these steps; and one or more of the facilities such as the distillation column 5, the distillation column 6, the ion exchange resin column 7, and the acetaldehyde removing system 9 (such as an acetaldehyde-removing column) are not always provided. The equipment may further include a product column downstream from the ion exchange resin column 7, as described later.

The reactor 1 is a unit with which the reaction step is performed. The reaction step is the step of continuously forming acetic acid by a reaction represented by Chemical Formula (1) below (methanol-carbonylation reaction). During steady operation of the acetic acid production equipment, a reaction mixture, which is typically stirred with a stirrer, is present in the reactor 1. The reaction mixture includes methanol and carbon monoxide as starting materials, a metal catalyst, a promoter, water, production target acetic acid, and various by-products. The reaction mixture is in an equilibrium state between a liquid phase and a gas phase.

Chemical Formula (1) is expressed as follows:

$$CH_3OH + CO \rightarrow CH_3COOH \qquad (1)$$

The starting materials in the reaction mixture are liquid methanol and gaseous carbon monoxide. Methanol is fed from a methanol storage unit (not shown) through the line 11 to the reactor 1 continuously at a predetermined flow rate.

Carbon monoxide is fed from a carbon monoxide storage unit (not shown) through the line 12 to the reactor 1 continuously at a predetermined flow rate. The carbon monoxide does not always have to be pure carbon monoxide and may include one or more other gases such as nitrogen, hydrogen, carbon dioxide, and oxygen in a small amount (typically, 5 mass percent or less, and preferably 1 mass percent or less).

The metal catalyst in the reaction mixture is employed so as to accelerate the methanol-carbonylation reaction, and may be selected typically from rhodium catalysts and iridium catalysts. A non-limiting example of the rhodium catalysts for use herein is a rhodium complex represented by the chemical formula: $[Rh(CO)_2I_2]^-$. A non-limiting example of the iridium catalysts for use herein is an iridium complex represented by the chemical formula: $[Ir(CO)_2I_2]^-$. The metal catalyst is preferably selected from metal complex catalysts. The catalyst is present in the reaction mixture in a concentration (in terms of metal) of typically 100 to 10000 ppm by mass, preferably 200 to 5000 ppm by mass, and furthermore preferably 400 to 3000 ppm by mass, of the totality of the liquid phase in the reaction mixture.

The promoter is an iodide to assist the action of the catalyst and may be selected typically from methyl iodide and ionic iodides. Methyl iodide is capable of offering the action of promoting the catalysis of the catalyst. Methyl iodide may be present in the reaction mixture in a concentration of typically 1 to 20 mass percent, relative to the totality of the liquid phase in the reaction mixture. The ionic iodides are iodides that form an iodine ion in the liquid reaction mixture (of which ionic metal iodides are typified) and are capable of offering the action of stabilizing the catalyst and/or the action of restraining side reactions. Non-limiting examples of the ionic iodides include alkali metal iodides such as lithium iodide, sodium iodide, and potassium iodide. The ionic iodide(s) may be preset in the reaction mixture in a concentration of typically 1 to 25 mass percent, and preferably 5 to 20 mass percent, relative to the totality of the liquid phase in the reaction mixture. When an iridium catalyst, for example, is used, a ruthenium compound and/or an osmium compound may be used as the promoter. These compounds may be used in a total amount of typically 0.1 to 30 moles (in terms of metal), and preferably 0.5 to 15 moles (in terms of metal), per mole (in terms of metal) of iridium.

Water in the reaction mixture is a component necessary for the formation of acetic acid, due to the reaction mechanism of the methanol-carbonylation reaction, and is a component necessary for dissolving water-soluble components in the reaction system. The water in the reaction mixture may be present in a concentration of typically 0.1 to 15 mass percent, preferably 0.8 to 10 mass percent, more preferably 1 to 6 mass percent, and furthermore preferably 1.5 to 4 mass percent, of the totality of the liquid phase in the reaction mixture. The water concentration is preferably 15 mass percent or less, so as to minimize energy necessary for the removal of water in an acetic acid purification process and for performing the acetic acid production more efficiently. To control the water concentration, water may be fed to the reactor 1 continuously at a predetermined flow rate.

The acetic acid in the reaction mixture includes acetic acid that has been charged into the reactor 1 before operation of the acetic acid production equipment; and acetic acid that is formed as a main product of the methanol-carbonylation reaction. The acetic acid as above is capable of functioning as a solvent in the reaction system. The acetic acid may be present in the reaction mixture in a concentration of typically 50 to 90 mass percent, and preferably 60 to 80 mass percent, of the totality of the liquid phase in the reaction mixture.

A non-limiting example of main by-products contained in the reaction mixture is methyl acetate. Methyl acetate can be formed from the reaction between acetic acid and methanol. Methyl acetate in the reaction mixture may be present in a concentration of typically 0.1 to 30 mass percent, and preferably 1 to 10 mass percent, of the totality of the liquid phase in the reaction mixture. A non-limiting example of the by-products contained in the reaction mixture is hydrogen iodide. When the catalyst with or without the promoter as above is used, hydrogen iodide is unavoidably formed due to the reaction mechanism of the methanol-carbonylation reaction. Hydrogen iodide in the reaction mixture may be present in a concentration of typically 0.01 to 2 mass percent relative to the totality of the liquid phase in the reaction mixture.

Non-limiting examples of the by-products also include hydrogen, methane, carbon dioxide, acetaldehyde, crotonaldehyde, 2-ethylcrotonaldehyde, butyl acetate, dimethyl ether, alkanes, formic acid, and propionic acid, as well as alkyl iodides such as ethyl iodide, propyl iodide, butyl iodide, hexyl iodide, and decyl iodide.

The liquid reaction mixture has an acetaldehyde concentration of typically 500 ppm by mass or less, preferably 450 ppm by mass or less, more preferably 400 ppm by mass or less, furthermore preferably 350 ppm by mass or less, and particularly preferably 300 ppm by mass or less (for example, 250 ppm by mass or less). The lower limit of the acetaldehyde concentration in the liquid reaction mixture is typically 1 ppm by mass (or 10 ppm by mass).

The liquid reaction mixture has a crotonaldehyde concentration of typically 5 ppm by mass or less, preferably 3 ppm by mass or less, and furthermore preferably 2 ppm by mass or less. The lower limit of the crotonaldehyde concentration in the liquid reaction mixture is 0 ppm by mass, but may be typically 0.1 ppm by mass (or 0.2 ppm by mass). The liquid reaction mixture has a 2-ethylcrotonaldehyde concentration of typically 5 ppm by mass or less, preferably 3 ppm by mass or less, and furthermore preferably 2 ppm by mass or less. The lower limit of the 2-ethylcrotonaldehyde concentration in the liquid reaction mixture is 0 ppm by mass, but may be typically 0.1 ppm by mass or 0.2 ppm by mass.

According to the present invention, to achieve the object to give an acetic acid product that yields a better potassium permanganate test result, the reflux ratio at the light ends column is controlled at a specific level or more; and the crotonaldehyde concentration in the first acetic acid stream, which is drawn from the light ends column, is controlled at a specific level or less, and/or the reflux ratio at the dehydration column is controlled at a specific level or more, as described above. In addition, for example, the hydrogen partial pressure in the reactor is increased, and/or the reflux ratio at the light ends column is increased, so as to lower the crotonaldehyde concentration and to lower the ratio of the crotonaldehyde concentration to the 2-ethylcrotonaldehyde concentration and/or the ratio of the crotonaldehyde concentration to the butyl acetate concentration each in the first acetic acid stream. The increase in reflux ratio at the light ends column and/or at the dehydration column allows crotonaldehyde to be concentrated at the column top of the corresponding distillation column. When recycled to the reactor, crotonaldehyde, which is concentrated, is hydrogenated into butyl alcohol, and butyl alcohol in turn reacts with acetic acid to form butyl acetate, and thus becomes harmless to the potassium permanganate test. In addition, the increase in hydrogen partial pressure in the reactor facilitates or enhances the hydrogenation and conversion of crotonaldehyde in the reactor through butyl alcohol to butyl acetate, which is harmless, as described above. Accordingly, in the present invention, the butyl acetate concentration in the liquid reaction mixture tends to be increased. However, increase in butyl acetate concentration may cause the acetic acid product to have a lower purity. To eliminate or minimize this, the butyl acetate concentration in the liquid reaction mixture is preferably controlled to typically 0.1 to 15 ppm by mass (particularly preferably 1 to 12 ppm by mass, and especially preferably 2 to 9 ppm by mass).

The reaction mixture may further include corrodible metals (also called corrosible metals) such as iron, nickel, chromium, manganese, and molybdenum, where the corrodible metals are metals resulting from corrosion of the equipment; and other metals such as cobalt, zinc, and copper. Hereinafter, the corrodible metals and other metals are also generically referred to as "corrodible metals and other metals".

In the reactor 1, which houses the reaction mixture as above, the reaction conditions may be set as follows: the reaction temperature is typically 150° C. to 250° C., the reaction pressure as a total pressure is typically 2.0 to 3.5 MPa (absolute pressure), and the carbon monoxide partial pressure is typically 0.4 to 1.8 MPa (absolute pressure), preferably 0.6 to 1.6 MPa (absolute pressure), and furthermore preferably 0.9 to 1.4 MPa (absolute pressure).

Vapors in the gas phase in the reactor 1 during operation of the equipment typically include carbon monoxide, hydrogen, methane, carbon dioxide, nitrogen, oxygen, methyl iodide, hydrogen iodide, water, methyl acetate, acetic acid, dimethyl ether, methanol, acetaldehyde, formic acid, and propionic acid. Hydrogen is contained in carbon monoxide used as the starting material, and forms as a result of a shift reaction ($CO+H_2O \rightarrow H_2+CO_2$) which occurs in the reactor 1. The hydrogen partial pressure in the reactor 1 is typically 0.001 MPa (absolute pressure) or more (for example, 0.005 MPa or more), preferably 0.01 MPa (absolute pressure) or more (for example, 0.015 MPa or more), more preferably 0.02 MPa (absolute pressure) or more, furthermore preferably 0.04 MPa (absolute pressure) or more, and particularly preferably 0.06 MPa (absolute pressure) or more (for example, 0.07 MPa (absolute pressure) or more). The upper limit of the hydrogen partial pressure in the reactor is typically 0.5 MPa (absolute pressure) (in particular, 0.2 MPa (absolute pressure)). An excessively increased hydrogen partial pressure in the reactor may cause increase in amount of acetaldehyde formation, and increase in amount of crotonaldehyde by aldol condensation; and, conversely, an excessively low hydrogen partial pressure may impede the reaction of crotonaldehyde into butanol, but, in this case, the reaction rate significantly varies with a small variation in hydrogen, and this unstabilizes the operation. The vapors in the gas phase in the reactor 1 can be drawn from the reactor 1 through the line 13. The inside pressure of the reactor 1 may be controlled by regulating the amount of the vapors to be drawn out, and is typically maintained at a constant level. The vapors drawn from the reactor 1 are introduced into the condenser 1a.

The condenser 1a cools and partially condenses the vapors from the reactor 1 to separate the vapors into a condensate and a gas. The condensate includes, for example, methyl iodide, hydrogen iodide, water, methyl acetate, acetic acid, dimethyl ether, methanol, acetaldehyde, formic acid, and propionic acid. The condensate is introduced and recycled from the condenser 1a through the line 14 to the reactor 1. The gas includes, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid. The gas is fed from the condenser 1a through the line 15 to the scrubber system 8. In the scrubber system 8, useful components (such as methyl iodide, water, methyl acetate, and acetic acid) are separated and recovered from the gas from the condenser 1a. In the embodiment, the separation and recovery employs a wet process using an absorbing liquid (absorbent) for collecting useful components from the gas. The absorbing liquid is preferably selected from absorbing solvents containing at least one of acetic acid and methanol. The absorbing liquid may contain methyl acetate. For example, a condensate derived from vapors from the after-mentioned distillation column 6 is usable as the absorbing liquid. The separation and recovery may employ a pressure swing adsorption process. The separated, recovered useful components (such as methyl iodide) are introduced and recycled from the scrubber system 8 through the recycle lines 48 and 23 to the reactor 1. A residual gas after the collection of useful components is discarded through the line 49. The gas discharged from the line 49 is usable as a carbon monoxide (CO) source to be introduced into the bottom of the after-mentioned evaporator 2, and/or into the residue recycling lines 18 and 19. The treatment in the scrubber system 8, subsequent recycling to the reactor 1, and discarding are also applicable to after-mentioned gas fed from other condensers to the scrubber system 8. The production methods according to the present invention preferably include a scrubbing step of subjecting an offgas from the process to an absorbing treatment with an absorbing solvent containing acetic acid, to separate the offgas into a carbon monoxide-rich stream and an acetic acid-rich stream.

Acetic acid is continuously formed in the reactor 1 during operation of the equipment, as described above. The reaction mixture containing the acetic acid is continuously drawn from the reactor 1 at a predetermined flow rate, and introduced through the line 16 into the subsequent (downstream) evaporator 2.

The evaporator 2 is a unit with which the evaporation step (flash step) is performed. The evaporation step is the step of partially evaporating the reaction mixture to separate the mixture into a vapor stream (volatile phase) and a residue stream (low volatile phase), where the reaction mixture is continuously introduced through the line 16 (reaction mixture feed line) into the evaporator 2. The evaporation may be performed by decompressing the reaction mixture with or without heating. In the evaporation step, the vapor stream temperature is typically 100° C. to 260° C., and preferably 120° C. to 200° C.; the residue stream temperature is typically 80° C. to 200° C., and preferably 100° C. to 180° C.; and the evaporator internal pressure is typically 50 to 1000 kPa (absolute pressure). The ratio (mass ratio) of the vapor stream to the residue stream, which are separated from each other in the evaporation step, is typically from 10:90 to 50:50.

The vapors formed in the step typically include methyl iodide, hydrogen iodide, water, methyl acetate, acetic acid, dimethyl ether, methanol, acetaldehyde, crotonaldehyde, 2-ethylcrotonaldehyde, butyl acetate, formic acid, and propionic acid, as well as alkyl iodides such as ethyl iodide, propyl iodide, butyl iodide, hexyl iodide, and decyl iodide. The vapors are continuously drawn from the evaporator 2 to the line 17 (vapor stream discharge line). A part of the vapor stream drawn from the evaporator 2 is continuously introduced into the condenser 2a, and another part of the vapor stream is continuously introduced through the line 21 into the subsequent (downstream) distillation column 3. The vapor stream has an acetic acid concentration of typically 50 to 85 mass percent (preferably 55 to 75 mass percent), a methyl iodide concentration of typically 2 to 50 mass percent (preferably 5 to 30 mass percent), a water concentration of typically 0.2 to 20 mass percent (preferably 1 to 15 mass percent), and a methyl acetate concentration of typically 0.2 to 50 mass percent (preferably 2 to 30 mass percent). The vapor stream has a crotonaldehyde concentration of typically 0 to 5.0 ppm by mass (for example, 0.01 to 4.0 ppm by mass), preferably 0.1 to 3.0 ppm by mass, and furthermore preferably 0.2 to 2.0 ppm by mass. The vapor stream has a 2-ethylcrotonaldehyde concentration of typically 0 to 3.0 ppm by mass (for example, 0.01 to 2.5 ppm by mass), preferably 0.02 to 2.0 ppm by mass, and more preferably 0.03 to 0.8 ppm by mass. The vapor stream has a butyl acetate concentration of typically 0.1 to 13 ppm by mass, preferably 0.2 to 12 ppm by mass, and furthermore preferably 0.3 to 9 ppm by mass.

The residue stream formed in the step includes the catalyst and the promoter (such as methyl iodide or lithium iodide) which have been contained in the reaction mixture; water, methyl acetate, acetic acid, crotonaldehyde, 2-ethylcrotonaldehyde, butyl acetate, formic acid, propionic acid, and other substances that remain without volatilization in the step. The residue stream is continuously introduced from the evaporator 2 through the line 18 into the heat exchanger 2b by the working of the pump 57. The heat exchanger 2b cools the residue stream from the evaporator 2. The cooled residue stream is continuously introduced and recycled from the heat exchanger 2b through the line 19 to the reactor 1. The line 18 and the line 19 are collectively referred to as "residue recycling lines". The residue stream has an acetic acid concentration of typically 55 to 90 mass percent, and preferably 60 to 85 mass percent.

The condenser 2a cools and partially condenses the vapor stream from the evaporator 2 to separate the vapor stream into a condensate and a gas. The condensate typically includes methyl iodide, hydrogen iodide, water, methyl acetate, acetic acid, dimethyl ether, methanol, acetaldehyde, crotonaldehyde, 2-ethylcrotonaldehyde, butyl acetate, formic acid, and propionic acid. The condensate is introduced and recycled from the condenser 2a through the lines 22 and 23 to the reactor 1. The gas typically includes carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid. The gas is fed from the condenser 2a through the lines 20 and 15 to the scrubber system 8. The acetic acid formation reaction in the reaction step is an exothermic reaction. In the evaporation step (flash step), a part of heat accumulated in the reaction mixture is transferred to vapors derived from the reaction mixture. The condensate resulting from cooling of the vapors in the condenser 2a is recycled to the reactor 1. Specifically, this acetic acid production equipment is capable of efficiently removing heat resulting from the methanol-carbonylation reaction, by the working of the condenser 2a.

The distillation column 3 is a unit with which the first distillation step is performed. The distillation column 3 in the embodiment is characterized as a so-called light ends column. The first distillation step is the step of subjecting the vapor stream to a distillation treatment to separate and remove light ends therefrom, where the vapor stream is continuously introduced into the distillation column 3. More specifically, the first distillation step is the step of separating the vapor stream, by distillation, into an overhead stream rich in at least one light end selected from methyl iodide and acetaldehyde, and an acetic acid stream rich in acetic acid. The distillation column 3 may be selected typically from rectification columns such as plate columns and packed columns. A plate column, when employed as the distillation column 3, may typically have 5 to 50 theoretical plates.

In the interior of the distillation column 3, the column top pressure is set typically at 80 to 160 kPa (gauge pressure), and the column bottom pressure is set at a pressure which is higher than the column top pressure and is typically from 85 to 180 kPa (gauge pressure). In the interior of the distillation column 3, the column top temperature is typically set at a temperature which is lower than the boiling point of acetic acid at the set column top pressure and is typically from 90° C. to 130° C. The column bottom temperature is typically set at a temperature which is equal to or higher than the boiling point of acetic acid at the set column bottom pressure and is typically from 120° C. to 165° C. (preferably from 125° C. to 160° C.)

Into the distillation column 3, the vapor stream from the evaporator 2 is continuously introduced through the line 21. At the distillation column 3, vapors as an overhead stream are continuously drawn from the column top portion to the line 24; and bottoms are continuously drawn from the column bottom portion to the line 25. There is disposed the reboiler 3b. An acetic acid stream (first acetic acid stream; liquid) as a side stream is continuously drawn through the line 27 at a height level between the column top portion and the column bottom portion in the distillation column 3.

The vapors drawn from the column top portion of the distillation column 3 include low-boiling components (light ends) in larger amounts as compared with the bottoms and the side stream from the distillation column 3, where the light ends herein are components having lower boiling points as compared with acetic acid. The vapors typically include methyl iodide, hydrogen iodide, water, methyl acetate, dimethyl ether, methanol, acetaldehyde, crotonaldehyde, and formic acid. The vapors also include acetic acid. The vapors as above are continuously introduced through the line 24 into the condenser 3a.

The condenser 3a cools and partially condenses the vapors from the distillation column 3 to separate the vapors into a condensate and a gas. The condensate typically includes methyl iodide, hydrogen iodide, water, methyl acetate, acetic acid, dimethyl ether, methanol, acetaldehyde, crotonaldehyde, and formic acid, and are continuously introduced from the condenser 3a through the line 28 into a decanter 4. The condensate introduced into the decanter 4 is liquid-liquid separated into an aqueous phase (upper phase) and an organic phase (methyl iodide phase; lower phase). The aqueous phase includes water, and other components such as methyl iodide, hydrogen iodide, methyl acetate, acetic acid, dimethyl ether, methanol, acetaldehyde, crotonaldehyde, and formic acid. The organic phase includes methyl iodide, and other components such as hydrogen iodide, water, methyl acetate, acetic acid, dimethyl ether, methanol, acetaldehyde, crotonaldehyde, and formic acid.

In the embodiment, a part of the aqueous phase is refluxed (returned) through the line 29 to the distillation column 3, and another part of the aqueous phase is introduced and recycled through the lines 29, 30, and 23 to the reactor 1. A part of the organic phase is introduced and recycled through the lines 31 and 23 to the reactor 1. Another part of the organic phase and/or another part of the aqueous phase is introduced through the lines 31 and 50 and/or through the lines 30 and 51 into the acetaldehyde removing system 9. In addition to, or instead of the refluxing of the aqueous phase, a part of the organic phase may be refluxed to the distillation column 3.

The reflux ratio at the distillation column 3 will be described below. When the aqueous phase alone of the condensate derived from the overhead stream (first overhead stream) is refluxed to the distillation column 3, the reflux ratio for the aqueous phase is desirably controlled to typically 2 or more, preferably 3 or more, more preferably 4 or more, furthermore preferably 8 or more, and particularly preferably 10 or more, where the reflux ratio for the aqueous phase is the ratio of the aqueous phase reflux amount to the aqueous phase distillate amount. When the organic phase alone of the condensate derived from the overhead stream is refluxed to the distillation column 3, the reflux ratio for the organic phase is desirably controlled to typically 1 or more, preferably 1.5 or more, more preferably 2 or more, furthermore preferably 4 or more, and particularly preferably 5 or more, where the reflux ratio for the organic phase is the ratio of the organic phase reflux amount to the organic phase distillate amount. When both the aqueous phase and the organic phase of the condensate derived from the overhead stream is refluxed to the distillation column 3, the total reflux ratio for the aqueous phase and the organic phase is desirably controlled to typically 1.5 or more, preferably 2.3 or more, more preferably 3 or more, furthermore preferably 6 or more, and particularly preferably 7.5 or more, where the total reflux ratio is the ratio of the totality of reflux amounts of the aqueous phase and the organic phase to the totality of distillate amounts of the aqueous phase and the organic phase. When the aqueous phase is refluxed to the distillation column 3, the reflux ratio for the aqueous phase is preferably 2 or more, more preferably 3 or more, furthermore preferably 5 or more, particularly preferably 8 or more, and especially preferably 12 or more, where the reflux ratio for the aqueous phase is the ratio of the aqueous phase reflux amount to the aqueous phase distillate amount. When the condensate is refluxed without liquid-liquid separation, the reflux ratio for the condensate is 1.5 or more, preferably 2.3 or more, more preferably 3.5 or more, furthermore preferably 6 or more, and particularly preferably 8.5 or more. A non-limiting example of the case where the condensate is refluxed without liquid-liquid separation is the case where the condensate is in a homogeneous state and is not separated into different liquids. The reflux ratio at the distillation column 3 may be typically 0.5 or more, regardless of which of the upper phase and the lower phase is refluxed, when the reflux ratio at the after-mentioned distillation column 5 is controlled to 0.1 or more (for example, 0.3 or more, and preferably 0.32 or more). The upper limit of the reflux ratio at the distillation column 3, in any case, may be typically 3000 (in particular, 1000), or may be 100 (in particular, 30). At an increased reflux ratio at the distillation column 3, crotonaldehyde is more concentrated at the column top of the distillation column 3, because crotonaldehyde (boiling point: 104° C.) has a lower boiling point as compared with acetic acid (boiling point: 117° C.). This allows the first acetic acid stream, which is obtained typically as a side stream, to have a lower crotonaldehyde concentration. Assume that the condensate component(s) (at least one of the aqueous phase and the organic phase) derived from the first overhead stream is recycled to the reactor 1, where crotonaldehyde is concentrated in the condensate component(s) by the increase in reflux ratio at the distillation column 3. In this case, the crotonaldehyde in the reactor 1 reacts with acetaldehyde to form 2-ethylcrotonaldehyde. In addition, the crotonaldehyde in the reactor 1 also reacts with hydrogen to form butanol, and the butanol reacts with acetic acid to be converted into butyl acetate. As compared with crotonaldehyde, 2-ethylcrotonaldehyde less affects the potassium permanganate test result, and butyl acetate does little or not affect the potassium permanganate test result. Thus, acetic acid tends to have still higher quality. At such an increased reflux ratio at the distillation column 3, 2-ethylcrotonaldehyde and butyl acetate tend to be concentrated in sidecuts at levels lower than the feeding level of the charge liquid fed to the distillation column 3, and/or in bottoms, because 2-ethylcrotonaldehyde and butyl acetate have boiling points respectively of 137° C. and 126° C., higher than the boiling point (117° C.) of acetic acid, and are present at the column top in lower (decreased) concentrations.

In the embodiment, a part of the organic phase is introduced through the lines 31, 50, and 58 into the distillation column 10 (crotonaldehyde-removing column) to separate and remove crotonaldehyde by distillation. This distillation may be performed continuously (as a continuous operation) or batchwise (as a batch treatment). When crotonaldehyde is formed in a very small amount in the reaction system, the separation and removal of crotonaldehyde is preferably performed batchwise at the time when crotonaldehyde accumulates to some extent in the aqueous phase and/or the organic phase. This is preferred typically for energy cost saving. When the continuous operation is performed, compatibility between quality control and steam saving can be obtained by changing or regulating the throughput (charge amount). The throughput at the distillation column 10 (crotonaldehyde-removing column) may be typically 0.0001 to 50 parts by mass (for example, 0.001 to 30 parts by mass), or may be 0.01 to 10 parts by mass (for example, 0.1 to 5 parts by mass), per 100 parts by mass of the charge amount at the distillation column 3 (first distillation column; light ends column). The distillation column 10 may be selected typically from rectification columns such as plate columns and packed columns. The distillation column 10 has typically 1 to 100 theoretical plates, preferably 2 to 50 theoretical plates, more preferably 4 to 30 theoretical plates, and furthermore preferably 5 to 20 theoretical plates (for example, 6 to 15 theoretical plates). When the distillation is performed continuously (in a continuous system), the feed liquid is preferably fed to the distillation column 10 preferably at an intermediate level in a height direction of the distillation column (at a level between the first lower plate from the column top and the first upper plate from the column bottom), but may be fed at a level lower than the top by 20% to 80% (2/10 to 8/10). The feeding of the charge liquid at an excessively low level may increase the loss of methyl iodide, and the feeding at an excessively high level may lower the crotonaldehyde removing amount (and alkanes removing amount). The feed liquid (charge liquid) to the distillation column 10 has a crotonaldehyde concentration of generally 0.01 to 50 ppm by mass (for example, 0.1 to 50 ppm by mass), preferably 0.3 to 30 ppm by mass, more preferably 0.5 to 10 ppm by mass, and furthermore preferably 0.8 to 7.0 ppm by mass (for example, 1.0 to 5.0 ppm by mass). Overhead vapors from the distillation column 10 are introduced through the line 59 into the condenser 10*a* and condensed therein to give a condensate. A part of the condensate is refluxed through the line 61 to the distillation column 10, and the remainder of the condensate is drawn as a distillate through the line 62. The distillate mainly includes methyl iodide and methyl acetate and also includes other components such as dimethyl ether and low-boiling alkanes. The distillate can be recycled typically to the decanter 4 and/or to the reactor 1. Of the overhead vapors, a gas, which is not condensed in the condenser 10*a*, is fed through the line 63 typically to the scrubber system 8. Bottoms are drawn from the column bottom of the distillation column 10 through the line 60. The bottoms mainly include high-boiling impurities such as crotonaldehyde, 2-ethylcrotonaldehyde, butyl acetate, and alkanes; and acetic acid. The bottoms are generally discarded. Water contained in a trace amount in the organic phase may be concentrated at the column top, or be drawn from the column bottom. In addition to, or instead of the introduction of the organic phase into the distillation column 10, the aqueous phase may be introduced through the lines 30, 51, and 58 into the distillation column 10. In this case, at the distillation column 10, a distillate including water is obtained from the column top, and bottoms including crotonaldehyde and other high-boiling impurities, and acetic acid are obtained from the column bottom. Thus, the treatment of at least one of the aqueous phase and the organic phase through the distillation column 10 enables efficient removal of crotonaldehyde, and can give an acetic acid product that yields a better potassium permanganate test result. This can downsize or eliminate large-scale facilities such as ozone treatment facilities, and can reduce steam cost and electric utility expense. The reflux ratio at the distillation column 10 is typically 0.01 or more, preferably 0.05 or more, more preferably 0.5 or more, furthermore preferably 5 or more, and particularly preferably 20 or more (for example, 30 or more), where the reflux ratio herein is the ratio of the reflux amount to the distillate amount. The upper limit of the reflux ratio at the distillation column 10 is typically 1000 (or 100). At an excessively high reflux ratio at the distillation column 10, crotonaldehyde, which is intended to be concentrated at the column bottom, is conversely concentrated at the column top; and acetic acid, which has a higher boiling point as compared with crotonaldehyde, is present in a higher concentration. To eliminate or minimize this, the reflux ratio at the distillation column 10 is preferably 100 or less. At the distillation column 10, crotonaldehyde is drawn from the column bottom, and the ratio of the crotonaldehyde concentration (ppm by mass) in the distillate to the crotonaldehyde concentration (ppm by mass) in the charge liquid is typically less than 1, preferably 0.95 or less, more preferably 0.80 or less, furthermore preferably 0.70 or less, and particularly preferably 0.60 or less (for example, 0.50 or less, especially preferably 0.30 or less, and particularly 0.20 or less). At the distillation column 10, the ratio of the crotonaldehyde concentration (ppm by mass) in the bottoms to the crotonaldehyde concentration (ppm by mass) in the charge liquid is typically greater than 1, preferably 1.2 or more, more preferably 1.5 or more, furthermore preferably 2.0 or more, particularly preferably 3.0 or more (for example, 4.0 or more, and especially preferably 5.0 or more), and still especially preferably 10 or more (for example, 20 or more).

In the acetaldehyde-removing step using the acetaldehyde removing system 9, acetaldehyde contained in at least a part of at least one liquid is separated and removed by a known technique such as distillation, extraction, or a combination of them, where the at least one liquid is selected from the group consisting of the condensate, the organic phase, and the aqueous phase. The separated acetaldehyde is discharged from the equipment through the line 53. Useful components (such as methyl iodide) contained in the condensate, the organic phase, and the aqueous phase are recycled to the reactor 1 through the lines 52 and 23.

FIG. 2 is a schematic flow chart illustrating an acetaldehyde removing system according to an embodiment. For example, assume that the organic phase is treated in the acetaldehyde-removing step according to the flow. In this case, the treatment is performed as follows. The organic phase is fed through a line 101 to a distillation column (first acetaldehyde-removing column) 91, and is separated by distillation into an acetaldehyde-rich overhead stream (line 102), and a methyl iodide-residue stream (bottoms stream) (line 103). The overhead stream is condensed in a condenser 91a to give a condensate. Of the condensate, a part (line 104) is refluxed to the distillation column 91, and the remainder (line 105) is fed to an extraction column 92. The condensate fed to the extraction column 92 is extracted with water introduced from a line 109. An extract resulting from the extraction is fed through a line 107 to a distillation column (second acetaldehyde-removing column) 93, and is separated by distillation into an acetaldehyde-rich overhead stream (line 112) and a water-rich residue stream (bottoms stream) (line 113). The acetaldehyde-rich overhead stream is condensed in a condenser 93a to give a condensate. Of the condensate, a part (line 114) is refluxed to the column top portion of the distillation column 93, and the remainder (line 115) is discharged out of the system. The methyl iodide-rich residue stream as bottoms from the first acetaldehyde-removing column 91, a methyl iodide-rich raffinate (line 108) from the extraction column 92, and the water-rich residue stream from the second acetaldehyde-removing column 93 are recycled respectively through lines 103, 111, and 113 to the reactor 1, and/or to an appropriate site in the process. For example, the methyl iodide-rich raffinate from the extraction column 92 can be recycled through a line 110 to the distillation column 91. The liquid in the line 113 is generally discharged as an effluent to the outside. Gases (lines 106 and 116), which have not been condensed in the condensers 91a and 93a, are subjected to an absorption treatment in the scrubber system 8, or discarded.

Assume that the aqueous phase is treated in the acetaldehyde-removing step according to the flow illustrated in FIG. 2. In this case, the aqueous phase is treated typically by a procedure as follows. The aqueous phase is fed through the line 101 to the distillation column (first acetaldehyde-removing column) 91 and is separated by distillation into an acetaldehyde-rich overhead stream (line 102), and a water-rich residue stream (line 103). The overhead stream is condensed in the condenser 91a to give a condensate. Of the condensate, a part (line 104) is refluxed to the column top portion of the distillation column 91, and the remainder (line 105) is fed to the extraction column 92. The condensate fed to the extraction column 92 is extracted with water introduced from the line 109. An extract resulting from the extraction is fed through the line 107 to the distillation column (second acetaldehyde-removing column) 93, and is separated by distillation into an acetaldehyde-rich overhead stream (line 112) and a water-rich residue stream (line 113). The acetaldehyde-rich overhead stream is condensed in the condenser 93a to give a condensate. Of the condensate, a part (line 114) is refluxed to the column top portion of the distillation column 93, and the remainder (line 115) is discharged out of the system. The water-rich residue stream as bottoms from the first acetaldehyde-removing column 91, a methyl iodide-rich raffinate (line 108) from the extraction column 92, and the water-rich residue stream as bottoms from the second acetaldehyde-removing column 93 are recycled respectively through the lines 103, 111, and 113 to the reactor 1, and/or to an appropriate site in the process. For example, the methyl iodide-rich raffinate from the extraction column 92 can be recycled through the line 110 to the distillation column 91. The liquid in the line 113 is generally discharged out as an effluent. Gases (lines 106 and 116), which have not been condensed in the condensers 91a and 93a, are subjected to an absorption treatment in the scrubber system 8, or discarded.

Instead of, or in addition to the technique, acetaldehyde derived from the process stream(s) including water, acetic acid (AC), methyl iodide (MeI), and acetaldehyde (AD) can also be separated and removed by extractive distillation. For example, acetaldehyde can be discharged out of the system by the following procedure. The process stream is liquid-liquid separated to an organic phase and an aqueous phase, and at least one of the organic phase and the aqueous phase is fed as a charge liquid to a distillation column (extractive distillation column). With this, an extractant (generally, water) is introduced into a concentrated zone in the distillation column, where the concentrated zone is a zone in which methyl iodide and acetaldehyde are concentrated, and is exemplified typically by space ranging from the column top to the charge liquid feeding level. A liquid (extract) falling down from the concentrated zone is drawn as a side stream (sidecut stream), the side stream is liquid-liquid separated into an aqueous phase and an organic phase, and the aqueous phase is subjected to distillation. Thus, acetaldehyde is discharged out of the system. When a relatively large amount of water is present in the distillation column, a liquid falling down from the concentrated zone may be drawn as a side stream without introduction of the extractant to the distillation column. For example, it is acceptable that this distillation column is provided with a unit (such as a chimney tray) capable of receiving the liquid (extract) falling down from the concentrated zone, and the liquid (extract) received by the unit is drawn as a side stream. The extractant is preferably introduced at a level higher than the charge liquid feeding level and is more preferably introduced to a position adjacent to the column top. The side stream is preferably drawn at a level lower than the extractant introducing level and higher than the charge liquid feeding level in a height direction of the distillation column. This technique enables high-concentration extraction of acetaldehyde from the concentrate of methyl iodide and acetaldehyde, with the extractant (generally, water). In addition, the technique enables efficient extraction of acetaldehyde with a small amount of the extractant, because of using, as an extraction zone, space between the extractant introducing level and the sidecut level. The technique can therefore significantly reduce the number of plates in the distillation column and can reduce the required steam amount, as compared typically with a technique of drawing an extract resulting from extractive distillation from a column bottom portion of a distillation column (extractive distillation column). Further, the technique enables removal of acetaldehyde under such conditions as to restrain or minimize the loss of methyl iodide out of the system, because the technique, as using a small amount of the extractant, can reduce the ratio (MeI/AD ratio) of methyl iodide to acetaldehyde in the aqueous extract as compared with the technique illustrated in FIG. 2, which employs aldehyde-removing distillation and aqueous extraction in combination. The acetaldehyde concentration in the side stream is significantly higher than the acetaldehyde concentrations in the charge liquid and in the bottoms (bottom liquid). The ratio of acetaldehyde to methyl iodide in the side stream is higher than the ratios of acetaldehyde to methyl iodide in the charge liquid and in the bottoms. An organic phase (methyl iodide phase) resulting from liquid-liquid separation of the side stream may be recycled to this distillation column. In this case, the organic phase resulting from liquid-liquid separation of the side stream is preferably recycled at a level lower than the side stream drawing level and higher than the charge liquid feeding level in a height direction of the distillation column. In addition, a miscible solvent may be introduced into the distillation column (extractive distillation column), where the miscible solvent is miscible with components (such as methyl acetate) constituting the organic phase resulting from liquid-liquid separation of the process stream. Non-limiting examples of the miscible solvent include acetic acid and ethyl acetate. The miscible solvent is preferably introduced at a level lower than the side stream drawing level and higher than the charge liquid feeding level, in the height direction of the distillation column. When the organic phase resulting from liquid-liquid separation of the side stream is recycled to this distillation column, the miscible solvent is preferably introduced at a level lower the organic phase recycling level. Recycling of the organic phase resulting from liquid-liquid separation of the side stream to the distillation column and/or the introduction of the miscible solvent to the distillation column can lower the methyl acetate concentration in the extract drawn as the side stream, can lower the methyl acetate concentration in an aqueous phase resulting from liquid-liquid separation of the extract, and, consequently, can restrain or minimize the contamination of the aqueous phase with methyl iodide.

The distillation column (extractive distillation column) has typically 1 to 100 theoretical plates, preferably 2 to 50 theoretical plates, furthermore preferably 3 to 30 theoretical plates, and particularly preferably 5 to 20 theoretical plates. Thus, the distillation column according to the technique enables efficient separation and removal of acetaldehyde with a smaller number of plates (theoretical plates), as compared with the number of plates (80 to 100 theoretical plates) in distillation columns and extractive distillation columns for use in conventional acetaldehyde removal. The mass ratio of the flow rate of the extractant to the flow rate of the charge liquid may be selected within the range of from 0.0001:100 to 100:100, but is generally from 0.0001:100 to 20:100, preferably from 0.001:100 to 10:100, more preferably from 0.01:100 to 8:100, and furthermore preferably from 0.1:100 to 5:100, where the charge liquid is at least one of the organic phase and the aqueous phase resulting from liquid-liquid separation of the process stream. At the distillation column (extractive distillation column), the column top temperature is typically 15° C. to 120° C., preferably 20° C. to 90° C., more preferably 20° C. to 80° C., and furthermore preferably 25° C. to 70° C.; and the column top pressure is typically about 0.1 to about 0.5 MPa (absolute pressure). Other conditions for the distillation column (extractive distillation column) may be as with conditions for distillation columns and extractive distillation columns for use in conventional acetaldehyde removal.

FIG. 3 is a schematic flow chart illustrating an acetaldehyde removing system using the extractive distillation, according to an embodiment. In this embodiment, at least one of the organic phase and the aqueous phase resulting from liquid-liquid separation of the process stream is fed as a charge liquid through a feed line 201 to an intermediate plate (at a level between the column top and the column bottom) of a distillation column 94, and water is introduced through a line 202 into a portion adjacent to the column top. Thus, extractive distillation is performed in the distillation column 94 (extractive distillation column). The distillation column 94 is provided with a chimney tray 200 at a level higher than the charge liquid feeding level, where the chimney tray 200 is capable of receiving a liquid (extract) falling down from a concentrated zone in the column, where methyl iodide and acetaldehyde are concentrated in the concentrated zone. In this extractive distillation, the liquid on the chimney tray 200 is drawn, preferably in the whole quantity, through a line 208, introduced into a decanter 95, and liquid-liquid separated in the decanter 95 to give an aqueous phase and an organic phase. The aqueous phase (including acetaldehyde) is fed from the decanter 95 through a line 212 and introduced into and cooled in a cooler 95a. Thus, methyl iodide dissolved in the aqueous phase is two-phase separated, and is liquid-liquid separated in a decanter 96 to give an aqueous phase and an organic phase. The aqueous phase is fed from the decanter 96 through a line 216 to a distillation column 97 (acetaldehyde-removing column) for distillation. Vapors from the column top are fed through a line 217 and introduced into and condensed in a condenser 97a to give a condensate (mainly including acetaldehyde and methyl iodide). A part of the condensate is refluxed to the column top of the distillation column 97, and the remainder is discarded, or fed through a line 220 to a distillation column 98 (extractive distillation column). Water is introduced through a line 222 into the distillation column 98 at a portion adjacent to the column top to perform extractive distillation. Vapors from the column top are brought through a line 223 into a condenser 98a and is condensed therein to give a condensate (mainly including methyl iodide). A part of the condensate is refluxed to the column top portion. The remainder of the condensate is recycled through a line 226 to the reaction system, or may be removed (discharged) out of the system. The organic phase (methyl iodide phase) in the decanter 95 is recycled, preferably in the whole quantity, through lines 209 and 210 to the distillation column 94 at a level lower than the level of the chimney tray 200. A part of the aqueous phase from the decanter 95, and the organic phase from the decanter 96 are recycled respectively through lines 213 and 210 and through lines 214 and 210 to the distillation column 94, but this recycling is not necessarily performed. A part of the aqueous phase from the decanter 95 may be used as the extractant (water) in the distillation column 94. A part of the aqueous phase from the decanter 96 may be recycled through the line 210 to the distillation column 94. In some cases (for example, in the case where the charge liquid includes methyl acetate), the distillation efficiency can be improved by charging a miscible solvent through a line 215 to the distillation column 94, where the miscible solvent is miscible with a component (such as methyl acetate) constituting the organic phase resulting from liquid-liquid separation of the process stream, and where the miscible solvent herein is exemplified by acetic acid and ethyl acetate. The miscible solvent is fed to the distillation column 94 at a level higher than the charge liquid feeding level (line 201 coupling level) and lower than the recycle line 210 coupling level. Bottoms from the distillation column 94 are recycled to the reaction system. Vapors from the column top of the distillation column 94 are fed through a line 203 and brought into and condensed in a condenser 94*a* to give a condensate, and the condensate is liquid-liquid separated in a decanter 99 into an aqueous phase and an organic phase. The organic phase is refluxed through a line 206 to the column top portion of the distillation column 94, and the aqueous phase is brought through a line 207 to the decanter 95. Bottoms (containing water as a principal component) from the distillation column 97 and bottoms (water containing a small amount of acetaldehyde) from the distillation column 98 (extractive distillation column) are transferred respectively through lines 218 and 224 and removed from the system, or recycled to the reaction system. Gases (lines 211, 221, and 227) which have not been condensed in the condensers 94*a*, 97*a*, and 98*a* are subjected to an absorption treatment in the scrubber system 8, or discarded.

FIG. 4 is a schematic flow chart illustrating acetaldehyde removing system using the extractive distillation, according to another embodiment. In this embodiment, the condensate derived from the vapors from the column top of the distillation column 94 is brought into a hold tank 100, and the whole quantity of the vapors is refluxed through a line 206 to a column top portion of the distillation column 94. The other configurations are as in the embodiment illustrated in FIG. 3.

FIG. 5 is a schematic flow chart illustrating an acetaldehyde removing system using the extractive distillation, according to yet another embodiment. In this embodiment, the whole quantity of a liquid on the chimney tray 200 is drawn, introduced through a line 208 directly to the cooler 95*a* without passing through the decanter 95, and cooled in the cooler 95*a* and fed to the decanter 96. The other configurations than this are as in the embodiment illustrated in FIG. 4.

Referring back to FIG. 1, the gas formed by the working of the condenser 3*a* typically includes carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid. The gas is fed from the condenser 3*a* through the lines 32 and 15 to the scrubber system 8. Of the gas that reaches the scrubber system 8, components such as methyl iodide, hydrogen iodide, water, methyl acetate, acetic acid, dimethyl ether, methanol, acetaldehyde, and formic acid are absorbed by the absorbing liquid in the scrubber system 8. Hydrogen iodide reacts with methanol or methyl acetate in the absorbing liquid to form methyl iodide. A liquid containing useful components such as the methyl iodide is recycled from the scrubber system 8 through the recycle lines 48 and 23 into the reactor 1.

The bottoms drawn from the column bottom portion of the distillation column 3 include heavy ends in larger amounts as compared with the overhead stream and the side stream from the distillation column 3, where the heavy ends are components having higher boiling points as compared with acetic acid. For example, the bottoms include propionic acid, as well as the catalyst and/or the promoter as being entrained. The bottoms also include, for example, acetic acid, methyl iodide, methyl acetate, crotonaldehyde, 2-ethylcrotonaldehyde, butyl acetate, and water. In the embodiment, a part of the bottoms as above is continuously introduced and recycled through the lines 25 and 26 to the evaporator 2; and another part of the bottoms is continuously introduced and recycled through the lines 25 and 23 to the reactor 1.

The first acetic acid stream continuously drawn as a side stream from the distillation column 3 is enriched with acetic acid as compared with the vapor stream continuously introduced to the distillation column 3. Specifically, the first acetic acid stream has an acetic acid concentration higher than the acetic acid concentration in the vapor stream. The first acetic acid stream has an acetic acid concentration of typically 90 to 99.9 mass percent, and preferably 93 to 99 mass percent. The first acetic acid stream includes, in addition to acetic acid, other components such as methyl iodide, hydrogen iodide, water, methyl acetate, dimethyl ether, methanol, acetaldehyde, crotonaldehyde, 2-ethylcrotonaldehyde, butyl acetate, formic acid, and propionic acid, as well as alkyl iodides such as ethyl iodide, propyl iodide, butyl iodide, hexyl iodide, and decyl iodide. The first acetic acid stream has a methyl iodide concentration of typically 0.1 to 8 mass percent, and preferably 0.2 to 5 mass percent; a water concentration of typically 0.1 to 8 mass percent, and preferably 0.2 to 5 mass percent; and a methyl acetate concentration of typically 0.1 to 8 mass percent, and preferably 0.2 to 5 mass percent.

According to the present invention, the crotonaldehyde concentration in the first acetic acid stream is controlled to 2.2 ppm by mass or less. This allows the second acetic acid stream to have a lower crotonaldehyde concentration and to yield a better potassium permanganate test result, where the second acetic acid stream results from separation and removal of water by the dehydration step. This can downsize or eliminate acetaldehyde-removing facilities and ozone treatment facilities which are conventionally used for better potassium permanganate test results. In addition, acetic acid yielding a good potassium permanganate test result can be obtained only through the light ends column and the dehydration column, and this can downsize or eliminate downstream facilities such as a heavy ends column and a product column (finishing column). The first acetic acid stream has a crotonaldehyde concentration of preferably 2.0 ppm by mass or less, more preferably 1.8 ppm by mass or less, furthermore preferably 1.5 ppm by mass or less, and particularly preferably 1.2 ppm by mass or less (for example, 1.0 ppm by mass or less, or 0.8 ppm by mass or less, and especially preferably 0.5 ppm by mass or less). Assume that the reflux ratio at the distillation column 5 is controlled to 0.1 or more (for example, 0.3 or more, and preferably 0.32 or more). In this case, the crotonaldehyde concentration in the first acetic acid stream is not limited within the range, and may be typically 5 ppm by mass or less (in particular, 2.5 ppm by mass or less), but preferably falls within the range.

The first acetic acid stream has a 2-ethylcrotonaldehyde concentration of typically 3.0 ppm by mass or less, preferably 2.0 ppm by mass or less, more preferably 1.0 ppm by mass or less, and furthermore preferably 0.8 ppm by mass or less (for example, 0.5 ppm by mass or less).

In the present invention, it is preferred to lower the ratio ($C_{CR}/C_{ECR}$) of the crotonaldehyde concentration $C_{CR}$ (ppm by mass) to the 2-ethylcrotonaldehyde concentration $C_{ECR}$ (ppm by mass) in the first acetic acid stream. The lowering of this ratio ($C_{CR}/C_{ECR}$) allows the acetic acid product to yield a better potassium permanganate test result, because crotonaldehyde more adversely affects the potassium permanganate test result as compared with 2-ethylcrotonaldehyde.

The first acetic acid stream has a ratio ($C_{CR}/C_{ECR}$) of the crotonaldehyde concentration $C_{CR}$ (ppm by mass) to the 2-ethylcrotonaldehyde concentration $C_{ECR}$ (ppm by mass) of typically 50 or less, preferably 35 or less, more preferably 25 or less, furthermore preferably 20 or less, and particularly preferably 15 or less. The lower limit of the ratio may be typically 0.01, 0.05, 0.1, 0.3, or 0.5.

The first acetic acid stream has a butyl acetate concentration of typically 15 ppm by mass or less, preferably 12 ppm by mass or less, more preferably 10 ppm by mass or less, and furthermore preferably 8 ppm by mass or less. The lower limit of the butyl acetate concentration in the first acetic acid stream is typically 0 ppm by mass (or 0.1 ppm by mass).

In the present invention, it is preferred to lower the ratio ($C_{CR}/C_{BA}$) of the crotonaldehyde concentration $C_{CR}$ (ppm by mass) to the butyl acetate concentration $C_{BA}$ (ppm by mass) in the first acetic acid stream. The lowering of the ratio ($C_{CR}/C_{BA}$) allows the acetic acid product to yield a better potassium permanganate test result, because butyl acetate is harmless to the potassium permanganate test.

The first acetic acid stream has a ratio ($C_{CR}/C_{BA}$) of the crotonaldehyde concentration $C_{CR}$ (ppm by mass) to the butyl acetate concentration $C_{BA}$ (ppm by mass) of typically 2.0 or less, preferably 1.5 or less, more preferably 1.0 or less, and furthermore preferably 0.6 or less. The lower limit of the ratio may be typically 0.001, 0.01, 0.02, 0.05, or 0.1.

In addition, in the present invention, the reflux ratio at the first distillation column is controlled at a specific level or more, and this allows crotonaldehyde to be concentrated in a column top portion of the distillation column; and allows the first acetic acid stream to have a lower crotonaldehyde concentration, where the first acetic acid stream is drawn as a side stream from the first distillation column. The first acetic acid stream has a crotonaldehyde concentration of typically 1.3 ppm by mass or less, preferably 1.0 ppm by mass or less, more preferably 0.85 ppm by mass or less, and particularly preferably 0.5 ppm by mass or less (for example, 0.25 ppm by mass or less). The control of the crotonaldehyde concentration in the first acetic acid stream to 1.3 ppm by mass or less allows the after-mentioned second acetic acid stream to have a significantly lower crotonaldehyde concentration and to yield a significantly better potassium permanganate test result. The lower limit of the crotonaldehyde concentration in the first acetic acid stream may be 0 ppm by mass, or may be typically 0.01 ppm by mass (or 0.10 ppm by mass). The first acetic acid stream has a 2-ethylcrotonaldehyde concentration of typically 1.0 ppm by mass or less, and preferably 0.50 ppm by mass or less. The control of the 2-ethylcrotonaldehyde concentration in the first acetic acid stream to 1.0 ppm by mass or less allows the second acetic acid stream to yield a still better potassium permanganate test result. The lower limit of the 2-ethylcrotonaldehyde concentration in the first acetic acid stream may be typically 0 ppm by mass, or 0.01 ppm by mass (or 0.10 ppm by mass). The first acetic acid stream has a butyl acetate concentration of typically 15 ppm by mass or less, preferably 10 ppm by mass or less, more preferably 8 ppm by mass or less, and particularly preferably 5 ppm by mass or less (for example, 3 ppm by mass or less). The control of the butyl acetate concentration in the first acetic acid stream to 15 ppm by mass or less allows the second acetic acid stream to have a higher purity. The lower limit of the butyl acetate concentration in the first acetic acid stream may be typically 0 ppm by mass, or 0.1 ppm by mass (for example, 0.3 ppm by mass or 1.0 ppm by mass).

The line 27 may be coupled to the distillation column 3 at a level higher than the coupling level of the line 21 in a height direction of the distillation column 3, as illustrated in the figure, but may also be coupled at a level lower than, or equal to, the coupling level of the line 21 to the distillation column 3. The first acetic acid stream from the distillation column 3 is introduced through the line 27 to the subsequent (downstream) distillation column 5 continuously at a predetermined flow rate. The line 27 and the distillation column 5 (at least portions that are to be in contact with a liquid and/or a gas) may be made of stainless steel, but are preferably made of a material selected from highly corrosion-resistant metals such as nickel-base alloys and zirconium, so as to restrain corrosion of the interior of the piping by hydrogen iodide and/or acetic acid.

The bottoms drawn from the column bottom portion of the distillation column 3, or the first acetic acid stream drawn as a side stream from the distillation column 3 may also serve as an acetic acid product without further treatment, as long as its quality is acceptable.

Potassium hydroxide may be fed or added through the line 55 (potassium hydroxide introducing line) to the first acetic acid stream passing through the line 27. The potassium hydroxide may be fed or added typically as a solution such as an aqueous solution. The feeding or addition of potassium hydroxide to the first acetic acid stream can decrease hydrogen iodide in the first acetic acid stream. Specifically, hydrogen iodide reacts with potassium hydroxide to give potassium iodide and water. This can decrease corrosion of distillation columns and other equipment caused by hydrogen iodide. In this process, potassium hydroxide can be fed or added to an appropriate site where hydrogen iodide is present. The potassium hydroxide added in the process also reacts with acetic acid to give potassium acetate.

The distillation column 5 is a unit with which the second distillation step is performed and is characterized in the embodiment as a so-called dehydration column. The second distillation step is the step of subjecting the first acetic acid stream to a distillation treatment to further purify acetic acid, where the first acetic acid stream is continuously introduced into the distillation column 5. The distillation column 5 (at least portions that are to be in contact with a liquid and/or a gas) is preferably made of a material selected from nickel-base alloys and zirconium. The use of the material as above can restrain or minimize corrosion of the interior of the distillation column caused by hydrogen iodide and/or acetic acid and can restrain dissolution of corrodible metal ions.

The charge liquid fed to the distillation column 5 includes at least a part of the first acetic acid stream (line 27) and may further include another stream than the first acetic acid stream, where non-limiting examples of the other stream include streams recycled from downstream steps, such as a stream from the line 42.

The distillation column 5 may be selected typically from rectification columns such as plate columns and packed columns. A plate column, when employed as the distillation column 5, may typically have 5 to 50 theoretical plates. According to the present invention, the reflux ratio at the distillation column 5 is controlled to 0.1 or more (for example, 0.3 or more, and preferably 0.32 or more). The control of the reflux ratio at the distillation column 5 to 0.1 or more (for example, 0.3 or more, and preferably 0.32 or more) allows crotonaldehyde flowing into the dehydration column to be concentrated at the column top, because of lower boiling point of crotonaldehyde as compared with acetic acid, and allows the second acetic acid stream to have a significantly lower crotonaldehyde concentration, where the second acetic acid stream is obtained as a side stream or a bottoms stream. In addition, assume that an overhead stream (second overhead stream) from the column top of the distillation column 5, where crotonaldehyde is concentrated, is recycled to the reactor 1. This allows acetic acid to have still higher quality, because crotonaldehyde is converted into 2-ethylcrotonaldehyde, which is less harmful to the potassium permanganate test result; and converted into butyl acetate, which is approximately harmless to the potassium permanganate test result, as described above.

The reflux ratio at the distillation column 5 is preferably 0.1 or more (for example, 0.3 or more, and preferably 0.32 or more), more preferably 0.35 or more, furthermore preferably 0.4 or more, particularly preferably 1 or more, and especially preferably 2 or more. When the crotonaldehyde concentration in the first acetic acid stream is controlled to 2.2 ppm by mass or less, the reflux ratio at the distillation column 5 may be typically 0.1 or more (preferably 0.2 or more, in particular, 0.3 or more, for example, 0.32 or more). The upper limit of the reflux ratio at the distillation column 5 is typically 3000 (in particular, 1000) and may be about 100 or about 10.

In a preferred embodiment, the reflux ratio at the distillation column 5 is typically 0.1 or more, preferably 0.3 or more (for example, 0.32 or more), more preferably 1.0 or more, furthermore preferably 5.0 or more, and particularly preferably 10 or more (for example, 12 or more). The upper limit of the reflux ratio at the distillation column 5 may be typically about 3000 (or about 1000), or about 200 (or about 100). Assume that the reflux ratio at the distillation column 5 is controlled to 0.1 or more (for example, 0.3 or more, and preferably 0.32 or more). This allows crotonaldehyde flowing into the distillation column 5 to be concentrated at the column top, because of lower boiling point of crotonaldehyde as compared with acetic acid, and allows the second acetic acid stream to have a significantly lowered crotonaldehyde concentration, where the second acetic acid stream is obtained as a side stream or a bottoms stream. In addition, assume that the overhead stream (second overhead stream) from the column top of the distillation column 5, where crotonaldehyde is concentrated, is recycled to the reactor 1. This allows acetic acid to have still higher quality, because crotonaldehyde is converted into 2-ethylcrotonaldehyde, which is less harmful to the potassium permanganate test result; and converted into butyl acetate, which is approximately harmless to the potassium permanganate test result, as described above.

In the distillation column 5 during the second distillation step, the column top pressure is typically 0.01 to 0.50 MPa (gauge pressure), preferably 0.10 to 0.28 MPa (gauge pressure), more preferably 0.15 to 0.23 MPa (gauge pressure), and furthermore preferably 0.17 to 0.21 MPa (gauge pressure); and the column bottom pressure is higher as compared with the column top pressure and is typically 0.13 to 0.31 MPa (gauge pressure), preferably 0.18 to 0.26 MPa (gauge pressure), and more preferably 0.20 to 0.24 MPa (gauge pressure). In the distillation column 5 during the second distillation step, the column top temperature is preferably lower than 175° C. (and more preferably lower than 165° C.), and the column bottom temperature is preferably lower than 185° C. (and more preferably lower than 175° C.) The control of the column top temperature and the column bottom temperature in the distillation column 5 within the ranges can more restrain or minimize corrosion of the inside of the distillation column by hydrogen iodide and/or acetic acid and can more restrain the dissolution of corrodible metal ions. The column top temperature is more preferably lower than 163° C., furthermore preferably lower than 161° C., particularly preferably lower than 160° C., and especially preferably lower than 155° C. The lower limit of the column top temperature is typically 110° C. The column bottom temperature is more preferably lower than 173° C., furthermore preferably lower than 171° C., and particularly preferably lower than 166° C. The lower limit of the column bottom temperature is typically 120° C.

At the distillation column 5, vapors are continuously drawn as an overhead stream (second overhead stream) from a column top portion to the line 33; and bottoms are continuously drawn from a column bottom portion to the line 34. There is disposed the reboiler 5b. A side stream (liquid or gas) may be continuously drawn from a portion of the distillation column 5 to the line 34, where the portion is at a height level between the column top portion and the column bottom portion.

The vapors drawn from the column top portion of the distillation column 5 include larger amounts of light ends as compared with the bottoms from the distillation column 5, where the light ends herein are low-boiling components having lower boiling points as compared with acetic acid. The vapors typically include methyl iodide, hydrogen iodide, water, methyl acetate, acetic acid, dimethyl ether, methanol, acetaldehyde, crotonaldehyde, and formic acid. The vapors as above are continuously introduced through the line 33 to the condenser 5a.

The condenser 5a cools and partially condenses the vapors from the distillation column 5 to separates the vapors into a condensate and a gas. The condensate typically includes water and acetic acid. A part of the condensate is continuously refluxed from the condenser 5a through the line 35 to the distillation column 5. Another part of the condensate is introduced and recycled from the condenser 5a through the lines 35, 36, and 23 to the reactor 1. The gas obtained by the working of the condenser 5a typically includes carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid, and is fed from the condenser 5a through the lines 37 and 15 to the scrubber system 8. Hydrogen iodide in the gas that reaches the scrubber system 8 is absorbed by the absorbing liquid in the scrubber system 8, and hydrogen iodide in the absorbing liquid reacts with methanol or methyl acetate to give methyl iodide. A liquid containing the methyl iodide and other useful components is recycled from the scrubber system 8 through the recycle lines 48 and 23 to the reactor 1.

The bottoms drawn from the column bottom portion of the distillation column 5, or the side stream (second acetic acid stream) drawn from a portion at an intermediate level of the column is enriched with acetic acid as compared with the first acetic acid stream which is continuously introduced to the distillation column 5. Specifically, the second acetic acid stream has an acetic acid concentration higher than the acetic acid concentration in the first acetic acid stream. The acetic acid concentration in the second acetic acid stream is typically 99.1 to 99.99 mass percent, as long as being higher than the acetic acid concentration of the first acetic acid stream. In the embodiment, the side stream, when drawn from the distillation column 5, is drawn at a level lower than the level at which the first acetic acid stream is introduced into the distillation column 5, where the levels are levels with respect to a height direction of the distillation column 5.

In the present invention, the second acetic acid stream yields a high potassium permanganate test result and can serve as intact as an acetic acid product. However, the second acetic acid stream may include trace amounts of impurities (such as crotonaldehyde, 2-ethylcrotonaldehyde, butyl acetate, propionic acid, potassium acetate (when potassium hydroxide is fed typically to the line 27), hydrogen iodide, and the catalyst and/or the promoter as being entrained. Accordingly, the bottoms or side stream may be continuously introduced through the line 34 into the distillation column 6 and be subjected to distillation.

The second acetic acid stream has a crotonaldehyde concentration of typically 2.0 ppm by mass or less, preferably 1.8 ppm by mass or less, more preferably 1.5 ppm by mass or less, furthermore preferably 1.2 ppm by mass or less, and particularly preferably 0.7 ppm by mass or less (for example, 0.5 ppm by mass or less). The second acetic acid stream has a 2-ethylcrotonaldehyde concentration of typically 3.0 ppm by mass or less, preferably 2.0 ppm by mass or less, more preferably 1.0 ppm by mass or less, and furthermore preferably 0.8 ppm by mass or less (for example, 0.5 ppm by mass or less).

In the present invention, it is preferred to lower the ratio ($C_{CR}/C_{ECR}$) of the crotonaldehyde concentration $C_{CR}$ (ppm by mass) to the 2-ethylcrotonaldehyde concentration $C_{ECR}$ (ppm by mass) in the second acetic acid stream. The lowering of the ratio ($C_{CR}/C_{ECR}$) allows the acetic acid product to yield a better potassium permanganate test result, because crotonaldehyde more adversely affects the potassium permanganate test result as compared with 2-ethylcrotonaldehyde.

The second acetic acid stream has a ratio ($C_{CR}/C_{ECR}$) of the crotonaldehyde concentration $C_{CR}$ (ppm by mass) to the 2-ethylcrotonaldehyde concentration $C_{ECR}$ (ppm by mass) of typically 50 or less, preferably 35 or less, more preferably 25 or less, furthermore preferably 20 or less, and particularly preferably 15 or less. The lower limit of the ratio may be typically 0.01, 0.05, 0.1, 0.3, or 0.5.

The second acetic acid stream has a butyl acetate concentration of typically 15 ppm by mass or less, preferably 12 ppm by mass or less, more preferably 10 ppm by mass or less, and furthermore preferably 8 ppm by mass or less. The lower limit of the butyl acetate concentration in the second acetic acid stream is typically 0 ppm by mass (or 0.1 ppm by mass).

In the present invention, it is preferred to lower the ratio ($C_{CR}/C_{BA}$) of the crotonaldehyde concentration $C_{CR}$ (ppm by mass) to the butyl acetate concentration $C_{BA}$ (ppm by mass) in the second acetic acid stream. The lowering of the ratio ($C_{CR}/C_{BA}$) allows the acetic acid product to yield a better potassium permanganate test result, because butyl acetate is approximately harmless to the potassium permanganate test.

The second acetic acid stream has a ratio ($C_{CR}/C_{BA}$) of the crotonaldehyde concentration $C_{CR}$ (ppm by mass) to the butyl acetate concentration $C_{BA}$ (ppm by mass) of typically 2.0 or less, preferably 1.5 or less, more preferably 1.0 or less, and furthermore preferably 0.6 or less. With a decreasing ratio ($C_{CR}/C_{BA}$), the acetic acid product yields a better potassium permanganate test result, because butyl acetate is approximately harmless to the potassium permanganate test. The lower limit of the ratio may be typically 0.001, 0.01, 0.02, 0.05, or 0.1.

In a preferred embodiment, the second acetic acid stream has a crotonaldehyde concentration of typically 0.98 ppm by mass or less, preferably 0.80 ppm by mass or less, more preferably 0.50 ppm by mass or less, furthermore preferably 0.30 ppm by mass or less, and particularly preferably 0.17 ppm by mass or less. The control of the crotonaldehyde concentration in the second acetic acid stream to 0.98 ppm by mass or less allows the second acetic acid stream to have a significantly lowered crotonaldehyde concentration and to yield a significantly better potassium permanganate test result. The lower limit of the crotonaldehyde concentration in the second acetic acid stream may be 0 ppm by mass, but may also be typically 0.01 ppm by mass (or 0.10 ppm by mass). In a preferred embodiment, the second acetic acid stream has a 2-ethylcrotonaldehyde concentration of typically 1.0 ppm by mass or less, preferably 0.50 ppm by mass or less, more preferably 0.30 ppm by mass or less, and furthermore preferably 0.20 ppm by mass or less. The control of the 2-ethylcrotonaldehyde concentration in the second acetic acid stream to 1.0 ppm by mass or less allows the second acetic acid stream to yield a still better potassium permanganate test result. The lower limit of the 2-ethylcrotonaldehyde concentration in the second acetic acid stream may be typically 0 ppm by mass, or 0.01 ppm by mass (for example, 0.10 ppm by mass).

In a preferred embodiment, the second acetic acid stream has a butyl acetate concentration of typically 15 ppm by mass or less, preferably 10 ppm by mass or less, more preferably 8 ppm by mass or less, and particularly preferably 5 ppm by mass or less (for example, 3 ppm by mass or less). The control of the butyl acetate concentration in the second acetic acid stream to 15 ppm by mass or less allows the second acetic acid stream to have higher purity. The lower limit of the butyl acetate concentration in the second acetic acid stream may be typically 0 ppm by mass, or 0.1 ppm by mass (for example, 0.3 ppm by mass or 1.0 ppm by mass).

The second acetic acid stream preferably yields a potassium permanganate test result of longer than 50 minutes, more preferably 60 minutes or longer, furthermore preferably 100 minutes or longer, particularly preferably 120 minutes or longer (for example, 180 minutes or longer, especially preferably 240 minutes or longer, and particularly preferably 360 minutes or longer).

Potassium hydroxide may be fed or added through the line 56 (potassium hydroxide introducing line) to the second acetic acid stream passing through the line 34. The potassium hydroxide may be fed or added as a solution such as an aqueous solution. The feeding or addition of potassium hydroxide to the second acetic acid stream can decrease hydrogen iodide in the second acetic acid stream. Specifically, hydrogen iodide reacts with potassium hydroxide to form potassium iodide and water. This can decrease the corrosion of distillation columns and other equipment caused by hydrogen iodide.

The distillation column 6 is a unit with which the third distillation step is performed, and is characterized in the embodiment as a so-called heavy ends column. The third distillation step is the step of subjecting the second acetic acid stream to a purification treatment to further purify acetic acid, where the second acetic acid stream is continuously introduced into the distillation column 6. This step is not indispensable in the embodiment. The distillation column 6 may be selected typically from rectification columns such as plate columns and packed columns. A plate column, when employed as the distillation column 6, typically has 5 to 50 theoretical plates and is operated at a reflux ratio of typically 0.2 to 3000, according to the number of theoretical plates. In the distillation column 6 during the third distillation step, the column top pressure is set typically at −100 to 150 kPa (gauge pressure), and the column bottom pressure is set at a pressure which is higher than the column top pressure and is typically −90 to 180 kPa (gauge pressure). In the distillation column 6 during the third distillation step, the column top temperature is set typically at a temperature which is higher than the boiling point of water and lower than the boiling point of acetic acid at the set column top pressure and which falls in the range from 50° C. to 150° C.; and the column bottom temperature is set typically at a temperature which is higher than the boiling point of acetic acid at the set column bottom pressure and falls in the range from 70° C. to 160° C.

At the distillation column 6, vapors as an overhead stream are continuously drawn from a column top portion to the line 38; and bottoms are continuously drawn from a column bottom portion to the line 39. There is disposed the reboiler 6b. A side stream (liquid or gas) is continuously drawn, to the line 46, from a portion at a height level between the column top portion and the column bottom portion in the distillation column 6. The line 46 may be coupled to the distillation column 6 at a level higher than the coupling level of the line 34 to the distillation column 6, as illustrated in the figure, but may be lower than, or equal to, the coupling level of the line 34 to the distillation column 6, where the levels are levels with respect to a height direction of the distillation column 6.

The vapors drawn from the column top portion of the distillation column 6 include larger amounts of light ends (components having lower boiling points as compared with acetic acid) as compared with the bottoms from the distillation column 6. The vapors include acetic acid, and other components such as methyl iodide, hydrogen iodide, water, methyl acetate, dimethyl ether, methanol, and formic acid. The vapors as above are continuously introduced through the line 38 into the condenser 6a.

The condenser 6a cools and partially condensates the vapors from the distillation column 6 and separate the vapors into a condensate and a gas. The condensate includes acetic acid, and other components such as methyl iodide, hydrogen iodide, water, methyl acetate, dimethyl ether, methanol, and formic acid. At least a part of the condensate is continuously refluxed from the condenser 6a through the line 40 to the distillation column 6. A part (distillate) of the condensate can be recycled from the condenser 6a through the lines 40, 41, and 42 to the first acetic acid stream in the line 27, which is before being introduced into the distillation column 5. In addition to, or instead of this, a part (distillate) of the condensate can be recycled from the condenser 6a through the lines 40, 41, and 43 to the vapor stream in the line 21, which is before being introduced into the distillation column 3. A part (distillate) of the condensate may be recycled from the condenser 6a through the lines 40, 44, and 23 to the reactor 1. A part of the distillate from the condenser 6a can be fed to the scrubber system 8 and be used as the absorbing liquid in the system, as described above. A gas after absorption of useful components in the scrubber system 8 is discharged out from the equipment. A liquid containing the useful components is introduced or recycled from the scrubber system 8 through the recycle lines 48 and 23 into the reactor 1. In addition, a part of the distillate from the condenser 6a may be brought through lines (out of the figure) to various pumps (not shown) being operated in the equipment and be used as a sealing liquid for the pumps. Further in addition, a part of the distillate from the condenser 6a may be drawn out of the system through a draw line attached to the line 40 steadily, or non-steadily at the time of need. When a part (distillate) of the condensate is removed from the distillation treatment system in the distillation column 6, the amount of the distillate (distillate amount) is typically 0.01 to 30 mass percent, preferably 0.1 to 10 mass percent, more preferably 0.3 to 5 mass percent, and furthermore preferably 0.5 to 3 mass percent, of the condensate obtained by the working of the condenser 6a. In contrast, the gas formed in the condenser 6a typically includes carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid. The gas is fed from the condenser 6a through the lines 45 and 15 to the scrubber system 8.

The bottoms drawn from the column bottom portion of the distillation column 6 through the line 39 include larger amounts of heavy ends (components having higher boiling points as compared with acetic acid) as compared with the overhead stream from the distillation column 6. The bottoms typically include propionic acid, and acetates such as potassium acetate (when potassium hydroxide or another alkali is fed typically to the line 34). The bottoms drawn from the column bottom portion of the distillation column 6 through the line 39 also include corrodible metals and other metals such as metals liberated from an inner wall of a constitutional member of the acetic acid production equipment; and compounds between iodine derived from corrosive iodine and the corrodible metals and other metals. The bottoms as above in the embodiment are discharged out from the acetic acid production equipment.

The side stream continuously drawn from the distillation column 6 to the line 46 is continuously introduced, as a third acetic acid stream, into the subsequent ion exchange resin column 7. The third acetic acid stream is enriched with acetic acid as compared with the second acetic acid stream which is continuously introduced into the distillation column 6. Specifically, the third acetic acid stream has an acetic acid concentration higher than the acetic acid concentration in the second acetic acid stream. The acetic acid concentration in the third acetic acid stream is typically 99.8 to 99.999 mass percent, as long as being higher than the acetic acid concentration in the second acetic acid stream. In the embodiment, the side stream is drawn from the distillation column 6 at a level higher than the level at which the second acetic acid stream is introduced into the distillation column 6, where the levels are levels with respect to a height direction of the distillation column 6. In another embodiment, the side stream is drawn from the distillation column 6 at a level equal to or lower than the level at which the second acetic acid stream is introduced into the distillation column 6, where the levels are levels with respect to a height direction of the distillation column 6. A simple distillator (evaporator) is usable instead of the distillation column 6. In particular, the present invention can give acetic acid yielding a very high potassium permanganate test result by the distillation treatment in the distillation column 5 and can thereby omit the distillation column 6.

The ion exchange resin column 7 is a purification unit with which the adsorptive removing step is performed. The adsorptive removing step is the step of adsorptively removing mainly alkyl iodides contained in trace amounts in the third acetic acid stream to further purify acetic acid, where the third acetic acid stream is continuously introduced into the ion exchange resin column 7. Non-limiting examples of the alkyl iodides include ethyl iodide, propyl iodide, butyl iodide, hexyl iodide, and decyl iodide. It is also acceptable that the distillation column 6 is omitted, and the second acetic acid stream from the distillation column 5 is fed to the ion exchange resin column 7. The adsorptive removing step using the ion exchange resin column 7 does not always have to be provided.

The ion exchange resin column 7 is packed with an ion exchange resin which is capable of adsorbing alkyl iodides and which forms an ion exchange resin bed. Non-limiting examples of the ion exchange resin as above include cation-exchange resins with part of leaving protons in an exchange group being substituted or replaced with a metal such as silver or copper, where the exchange group is exemplified typically by sulfonic group, carboxy group, and phosphonate group. In the adsorptive removing step, the third acetic acid stream (liquid) passes through the inside of the ion exchange resin column 7 packed typically with the ion exchange resin as above, and, during the passing process, alkyl iodides and other impurities in the third acetic acid stream are adsorbed by the ion exchange resin and removed from the third acetic acid stream. At the ion exchange resin column 7 during the adsorptive removing step, the inside temperature is typically 18° C. to 100° C., and the flow rate of the acetic acid stream is typically 3 to 15 m$^3$/h·m$^3$ (resin volume), where the flow rate is the acetic acid throughput (m$^3$/h) per cubic meter of the resin volume.

A fourth acetic acid stream is continuously brought from a lower end portion of the ion exchange resin column 7 to the line 47. The fourth acetic acid stream has a higher acetic acid concentration than the acetic acid concentration in the third acetic acid stream. Specifically, the fourth acetic acid stream is enriched with acetic acid as compared with the third acetic acid stream which is continuously introduced into the ion exchange resin column 7. The acetic acid concentration in the fourth acetic acid stream is typically 99.9 to 99.999 mass percent, or more, as long as being higher than the acetic acid concentration in the third acetic acid stream. In the production method, the fourth acetic acid stream can be stored in a product tank (out of the figure).

The acetic acid production equipment may further include a so-called product column or finishing column, which is a distillation column, as a purification unit for further purifying the fourth acetic acid stream from the ion exchange resin column 7. The product column as above, when provided, may be selected typically from rectification columns such as plate columns and packed columns. A plate column, when employed as the product column, typically has 5 to 50 theoretical plates and is operated at a reflux ratio of typically 0.5 to 3000, according to the number of theoretical plates. In the product column during the purification step, the column top pressure is set typically at −195 to 150 kPa (gauge pressure), and the column bottom pressure is set at a pressure which is higher than the column top pressure and is typically −190 to 180 kPa (gauge pressure). In the product column, the column top temperature is typically set at a temperature which is higher than the boiling point of water and lower than the boiling point of acetic acid at the set column top pressure, and falls in the range from 50° C. to 150° C.; and the column bottom temperature is typically set at a temperature which is higher than the boiling point of acetic acid at the set column bottom pressure and falls in the range from 70° C. to 160° C. Instead of the product column or finishing column, a simple distillator (evaporator) may be used.

When the product column is provided, all or a part of the fourth acetic acid stream (liquid) from the ion exchange resin column 7 is continuously introduced into the product column. At the product column as above, vapors as an overhead stream are continuously drawn from a column top portion, where the overhead stream includes trace amounts of light ends such as methyl iodide, water, methyl acetate, dimethyl ether, crotonaldehyde, acetaldehyde, and formic acid. The vapors are separated using a predetermined condenser into a condensate and a gas. Of the condensate, a part is continuously refluxed to the product column; and another part may be recycled to the reactor 1, or be discharged to the outside of the system, or both. The gas is fed to the scrubber system 8. At the product column, bottoms including trace amounts of heavy ends are continuously drawn from a column bottom portion, and the bottoms are typically recycled to the second acetic acid stream in the line 34, before being introduced into the distillation column 6. At the product column, a side stream (liquid) as a fifth acetic acid stream is continuously drawn from a portion at a height level between the column top portion and the column bottom portion. The side stream is drawn from the product column typically at a level lower than the level at which the fourth acetic acid stream is introduced into the product column, where the levels are levels with respect to a height direction of the product column. The fifth acetic acid stream is enriched with acetic acid as compared with the fourth acetic acid stream which is continuously introduced into the product column. Specifically, the fifth acetic acid stream has an acetic acid concentration higher than the acetic acid concentration in the fourth acetic acid stream. The acetic acid concentration in the fifth acetic acid stream is typically 99.9 to 99.999 mass percent, or more, as long as being higher than the acetic acid concentration in the fourth acetic acid stream. The fifth acetic acid stream is stored typically in a product tank. Instead of, or in addition to, being arranged downstream from the distillation column 6, the ion exchange resin column 7 may be arranged downstream from the product column for the treatment of the acetic acid stream from the product column.

EXAMPLES

The present invention will be illustrated in further detail with reference to several examples below. The examples are each on the basis of an exemplary test operation, and conditions, such as chemical compositions and operation conditions, for carrying out the examples are indicated with very specific numerical values. However, these numerical values are never construed to limit the scope of the present invention. The chemical composition in the system is affected by and responds to (reacts with) components such as hydrogen and oxygen and may be varied slightly. Accordingly, numerical values for the examples in the tables indicate numerical values at some time point during the operation. All parts, percentages, parts per million (ppm), and parts per billion (ppb) are by mass. Water concentrations (water content) were measured by the Karl Fischer method (moisture measurement method), metal ion concentrations were measured by ICP analyses (or atomic absorption spectrometry), and concentrations of other components were measured by gas chromatography. Potassium permanganate test results were determined according to the procedure for visual colorimetry prescribed in JIS K 1351:1993.

Comparative Example 1

An experiment as follows was performed in a methanol-carbonylation acetic acid pilot plant (see FIG. 1).

A liquid reaction mixture (400 parts) obtained from a reactor was charged into an evaporator and evaporated by 25%. The reactor was operated at a total pressure of 2.8 MPa (absolute pressure), a carbon monoxide partial pressure of 1.4 MPa (absolute pressure), a hydrogen partial pressure of 0.04 MPa (absolute pressure), and a reaction temperature of 187° C. The liquid reaction mixture had a chemical composition including 7.9% of methyl iodide (MeI), 2.1% of methyl acetate (MA), 2.5% of water (H$_2$O), 910 ppm (in terms of Rh) of a rhodium complex, 14.1% of lithium iodide (LiI), 110 ppm of propionic acid, 30 ppm of formic acid, 402 ppm of acetaldehyde (AD), 1.7 ppm of crotonaldehyde (CR), 1.2 ppm of 2-ethylcrotonaldehyde (2ECR), and 8.3 ppm of butyl acetate (BA), with the remainder being acetic acid (but including trace amounts of impurities). Vapors from the evaporator had a chemical composition including 28.1% of methyl iodide, 4.9% of methyl acetate, 1.9% of water, 73 ppm of propionic acid, 85 ppm of formic acid, 1500 ppm of acetaldehyde, 2.0 ppm of crotonaldehyde, 0.02 ppm of 2-ethylcrotonaldehyde, and 5.4 ppm of butyl acetate, with the remainder being acetic acid (but including trace amounts of impurities). The vapors (100 parts) were charged into a light ends column, where the light ends column had 20 actual plates and was operated at a column top pressure of 250 kPa (absolute pressure) and a column top temperature of 140° C., and where the vapors were charged at the 2nd plate from the bottom. Overhead vapors from the light ends column were condensed to give a condensate, and the condensate was separated into an aqueous phase and an organic phase. A part (11 parts) of the organic phase was fed to an acetaldehyde-removing column, where acetaldehyde was removed from the system, and the organic phase after the removal of acetaldehyde was recycled to the reaction system. The acetaldehyde-removing column had 80 actual plates and was operated at a column top pressure of 280 kPa (absolute pressure) and a column top temperature of 52° C., and the part of the organic phase was charged at the 11th plate from the bottom. The remainder (41 parts) of the organic phase was recycled directly to the reaction system. Of the aqueous phase, a part was refluxed (recycled) to the light ends column, and the remainder was recycled, as a distillate, in an amount of 1.5 parts to the reaction system. This process was performed at a reflux ratio of 2, where the reflux ratio is defined as the ratio of the aqueous phase reflux amount to the distillate amount. From bottoms from the light ends column, 3 parts were drawn and recycled to the reaction system. From an intermediate portion (4th plate from the bottom) of the light ends column, a sidecut (SC) stream (65 parts) was drawn, and charged into a dehydration column, where the dehydration column had 50 actual plates and was operated at a column top pressure of 295 kPa (absolute pressure) and a column top temperature of 150° C., and the sidecut stream was charged at the 34th plate from the bottom. The sidecut had a ratio $C_{CR}/C_{ECR}$ of 70.0 and a ratio $C_{CR}/C_{BA}$ of 0.28. Of an overhead condensate from the dehydration column, a part was refluxed (recycled) to the dehydration column, and the remainder was recycled, as a distillate, in an amount of 19 parts to the reaction system. This process was performed with a reflux ratio at the dehydration column of 0.3, where the reflux ratio is the ratio of the reflux amount to the distillate amount. As a result, 46 parts of an acetic acid product were obtained from bottoms from the dehydration column. The acetic acid product had a crotonaldehyde concentration of 1.90 ppm, a 2-ethylcrotonaldehyde concentration of 0.04 ppm, and a butyl acetate concentration of 7.9 ppm. The acetic acid product obtained from the column bottom of the dehydration column had a ratio $C_{CR}/C_{ECR}$ of 45.2 and a ratio $C_{CR}/C_{BA}$ of 0.24. As a result of measurement, the acetic acid product was found to have a permanganate time of 20 minutes. The results are given in Table 1.

Comparative Example 2

An experiment was performed by a procedure similar to that in Comparative Example 1, except for feeding the organic phase of the light ends column overhead condensate to the acetaldehyde-removing column in an amount of 21 parts. These changes changed the chemical compositions of process liquids. As a result, the sidecut from the light ends column had a crotonaldehyde concentration of 1.1 ppm, a ratio $C_{CR}/C_{ECR}$ of 5.5, and a ratio $C_{CR}/C_{BA}$ of 1.83. An acetic acid product obtained from the column bottom of the dehydration column had a crotonaldehyde concentration of 0.99 ppm, a 2-ethylcrotonaldehyde concentration of 0.29 ppm, a butyl acetate concentration of 0.76 ppm, a ratio $C_{CR}/C_{ECR}$ of 3.4, and a ratio $C_{CR}/C_{BA}$ of 1.30. As a result of measurement, the acetic acid product was found to have a permanganate time of 50 minutes. The results are given in Table 1.

Example 1

An experiment was performed by a procedure similar to that in Comparative Example 1, except for changing conditions as follows. The reflux ratio at the light ends column was set at 15, and the reflux ratio at the dehydration column was set at 10. Of 41 parts of the organic phase, all of which were directly recycled to the reactor in Comparative Example 1, 20 parts were charged into a crotonaldehyde-removing column (whereas 21 parts were directly recycled to the reactor). The organic phase had a chemical composition including 0.3% of alkanes, 1300 ppm of acetaldehyde, 12.5% of methyl acetate, 0.7% of water, 1.9% of acetic acid, 1.5 ppm of crotonaldehyde, 0.1 ppm of 2-ethylcrotonaldehyde, and 0.3 ppm of butyl acetate, with the remainder being methyl iodide (but including trace amounts of impurities). The crotonaldehyde-removing column was a packed column having 10 theoretical plates and was operated at a column top pressure of 280 kPa (absolute pressure) and a column top temperature of 52° C., where the 20 parts of the organic phase were charged at 5th theoretical plate from the bottom. At the crotonaldehyde-removing column, 19.48 parts were distilled as a distillate at a reflux ratio of 0.1, and the distillate was circulated to a decanter; and 0.52 part of bottoms was drawn from the column bottom, where the distillate had a chemical composition including 1305 ppm of acetaldehyde, 12.5% of methyl acetate, 0.7% of water, 0.1% of acetic acid, 1.4 ppm of crotonaldehyde, 0.05 ppm of 2-ethylcrotonaldehyde, and 0.2 ppm of butyl acetate, with the remainder being methyl iodide (but including trace amounts of impurities), and the bottoms had a chemical composition including 2.1% of methyl acetate, 1.5% of water, 5.5% of methyl iodide, 5.2 ppm of crotonaldehyde, 2.0 ppm of 2-ethylcrotonaldehyde, 3.9 ppm of butyl acetate, and 1.2% of alkanes, with the remainder being acetic acid (but including trace amounts of impurities). These changes changed the chemical compositions of process liquids. As a result, a sidecut from the light ends column had a crotonaldehyde concentration of 1.9 ppm. Thus, the sidecut had a lower ratio $C_{CR}/C_{ECR}$ of 38 and a lower ratio $C_{CR}/C_{BA}$ of 0.23, as compared with Comparative Example 1. An acetic acid product obtained from the column bottom of the dehydration column had a crotonaldehyde concentration of 0.75 ppm, a 2-ethylcrotonaldehyde concentration of 0.07 ppm, and a butyl acetate concentration of 10.0 ppm. Thus, the acetic acid product had a lower ratio $C_{CR}/C_{ECR}$ of 10.7 and a lower ratio $C_{CR}/C_{BA}$ of 0.08, as compared with Comparative Example 1. The acetic acid product was found to have a permanganate time of 80 minutes, as a result of measurement. The results are given in Table 1.

Example 2

An experiment was performed by a procedure similar to that in Example 1, except for setting the reflux ratio at the light ends column to 20, and the reflux ratio at the dehydration column to 15. These changes changed the chemical compositions of process liquids. As a result, a sidecut from the light ends column had a crotonaldehyde concentration of 1.8 ppm and; had a lower ratio $C_{CR}/C_{ECR}$ of 22.5 and a lower ratio $C_{CR}/C_{BA}$ of 0.24 as compared with Comparative Example 1. An acetic acid product obtained from the column bottom of the dehydration column had a crotonaldehyde concentration of 0.67 ppm, a 2-ethylcrotonaldehyde concentration of 0.12 ppm, and a butyl acetate concentration of 10.7 ppm. The acetic acid product had a lower ratio $C_{CR}/C_{ECR}$ of 5.6 and a lower ratio $C_{CR}/C_{BA}$ of 0.06, as compared with Comparative Example 1. As a result of measurement, the acetic acid product was found to have a permanganate time of 100 minutes. The results are given in Table 1.

Example 3

An experiment was performed by a procedure similar to that in Example 1, except for setting the reflux ratio at the light ends column to 25 and the reflux ratio at the dehydration column to 20. These changes changed the chemical compositions of process liquids. As a result, a sidecut from the light ends column had a crotonaldehyde concentration of 1.7 ppm, and had a lower ratio $C_{CR}/C_{ECR}$ of 8.5 and a lower ratio $C_{CR}/C_{BA}$ of 0.17 as compared with Comparative Example 1. An acetic acid product obtained from the column bottom of the dehydration column had a crotonaldehyde concentration of 0.62 ppm, a 2-ethylcrotonaldehyde concentration of 0.28 ppm, and a butyl acetate concentration of 11.5 ppm. The acetic acid product had a lower ratio $C_{CR}/C_{ECR}$ of 2.2 and a lower ratio $C_{CR}/C_{BA}$ of 0.05, as compared with Comparative Example 1. As a result of measurement, the acetic acid product was found to have a permanganate time of 120 minutes. The results are given in Table 1.

Example 4

An experiment was performed by a procedure similar to that in Example 1, except for charging the organic phase of the light ends column overhead condensate to the acetaldehyde-removing column in an amount of 21 parts, and operating the crotonaldehyde-removing column at a reflux ratio of 10. These changes changed the chemical compositions of process liquids. As a result, a sidecut from the light ends column had a crotonaldehyde concentration of 0.2 ppm and; had a lower ratio $C_{CR}/C_{ECR}$ of 0.7 and a lower ratio $C_{CR}/C_{BA}$ of 0.15 as compared with Comparative Example 1. An acetic acid product obtained from the column bottom of the dehydration column had a crotonaldehyde concentration of 0.18 ppm, a 2-ethylcrotonaldehyde concentration of 0.42 ppm, and a butyl acetate concentration of 1.8 ppm. The acetic acid product had a lower ratio $C_{CR}/C_{ECR}$ of 0.4 and a lower ratio $C_{CR}/C_{BA}$ of 0.10, as compared with Comparative Example 1. As a result of measurement, the acetic acid product was found to have a permanganate time of 360 minutes. The results are given in Table 1.

Example 5

An experiment was performed by a procedure similar to that in Example 1, except for operating the light ends column at a reflux ratio of 20, operating the dehydration column at a reflux ratio of 20, feeding the organic phase of the light ends column overhead condensate to the acetaldehyde-removing column in an amount of 21 parts, and operating the crotonaldehyde-removing column at a reflux ratio of 10. As a result, a sidecut from the light ends column had a crotonaldehyde concentration of 0.2 ppm, and had a lower ratio $C_{CR}/C_{ECR}$ of 0.4 and a lower ratio $C_{CR}/C_{BA}$ of 0.11 as compared with Comparative Example 1. An acetic acid product obtained from the column bottom of the dehydration column had a crotonaldehyde concentration of 0.13 ppm, a 2-ethylcrotonaldehyde concentration of 0.47 ppm, and a butyl acetate concentration of 2.1 ppm. The acetic acid product had a lower ratio $C_{CR}/C_{ECR}$ of 0.3 and a lower ratio $C_{CR}/C_{BA}$ of 0.06, as compared with Comparative Example 1. As a result of measurement, the acetic acid product was found to have a permanganate time of 400 minutes. The results are given in Table 1.

In Table 1, "$C_{AD}$" represents the acetaldehyde concentration, "$C_{CR}$" represents the crotonaldehyde concentration, "$C_{ECR}$" represents the 2-ethylcrotonaldehyde concentration, and "$C_{BA}$" represents the butyl acetate concentration. The numerical values for respective components in Table 1 indicate concentrations. The "distillate [CR]/charge liquid [CR]" represents the ratio of the crotonaldehyde concentration (ppm by mass) in the distillate to the crotonaldehyde concentration (ppm by mass) in the charge liquid. The "bottoms[CR]/charge liquid [CR]" represents the ratio of the crotonaldehyde concentration (ppm by mass) in the bottoms to the crotonaldehyde concentration (ppm by mass) in the charge liquid.

TABLE 1

|  |  | Comparative Examples | | Examples | | | | |
| --- | --- | --- | --- | --- | --- | --- | --- | --- |
|  |  | 1 | 2 | 1 | 2 | 3 | 4 | 5 |
| Hydrogen partial pressure in reactor (MPa) | | 0.04 | 0.04 | 0.04 | 0.04 | 0.04 | 0.04 | 0.04 |
| Reflux ratio at light ends column | | 2 | 2 | 15 | 20 | 25 | 15 | 20 |
| Reflux ratio at dehydration column | | 0.3 | 0.3 | 10 | 15 | 20 | 10 | 20 |
| Reflux ratio at crotonaldehyde-removing column | | — | — | 0.1 | 0.1 | 0.1 | 10 | 10 |
| Liquid reaction mixture | $C_{AD}$ (ppm) | 402 | 205 | 400 | 395 | 403 | 210 | 210 |
|  | $C_{CR}$ (ppm) | 1.7 | 1.3 | 1.7 | 1.7 | 1.8 | 0.9 | 0.7 |
|  | $C_{ECR}$ (ppm) | 1.2 | 1.5 | 1.5 | 1.6 | 1.7 | 1.3 | 1.2 |
|  | $C_{BA}$ (ppm) | 8.3 | 4.5 | 9.2 | 10.1 | 11.3 | 8.0 | 9.1 |
| Charge to light ends column | $C_{CR}$ (ppm) | 2.0 | 1.4 | 2.0 | 2.1 | 2.1 | 1.1 | 1.2 |
|  | $C_{ECR}$ (ppm) | 0.02 | 0.22 | 0.04 | 0.05 | 0.05 | 0.32 | 0.39 |
|  | $C_{BA}$ (ppm) | 5.4 | 0.6 | 6.3 | 6.3 | 6.3 | 1.1 | 1.2 |
| Sidecut liquid from light ends column | $C_{CR}$ (ppm) | 2.1 | 1.1 | 1.9 | 1.8 | 1.7 | 0.2 | 0.2 |
|  | $C_{ECR}$ (ppm) | 0.03 | 0.20 | 0.05 | 0.08 | 0.20 | 0.30 | 0.35 |
|  | $C_{BA}$ (ppm) | 7.6 | 0.6 | 8.4 | 7.6 | 9.8 | 1.3 | 1.4 |
|  | $C_{CR}/C_{ECR}$ | 70.0 | 5.5 | 38 | 22.5 | 8.5 | 0.7 | 0.4 |
|  | $C_{CR}/C_{BA}$ | 0.28 | 1.83 | 0.23 | 0.24 | 0.17 | 0.15 | 0.11 |

TABLE 1-continued

|  |  | Comparative Examples | | Examples | | | | |
| --- | --- | --- | --- | --- | --- | --- | --- | --- |
|  |  | 1 | 2 | 1 | 2 | 3 | 4 | 5 |
| Crotonaldehyde-removing column | Charge liquid CR (ppm) | — | — | 3.5 | 3.4 | 3.3 | 2.5 | 2.4 |
|  | Distillate CR (ppm) | — | — | 2.8 | 2.7 | 2.6 | 0.3 | 0.3 |
|  | Bottoms CR (ppm) | — | — | 17.3 | 17.2 | 17.2 | 110 | 110 |
|  | Distillate [CR]/Charge liquid [CR] | — | — | 0.80 | 0.79 | 0.79 | 0.12 | 0.13 |
|  | Bottoms [CR]/Charge liquid [CR] | — | — | 4.9 | 5.1 | 5.2 | 44.0 | 45.8 |
| Bottoms from dehydration column (product) | $C_{CR}$ (ppm) | 1.90 | 0.99 | 0.75 | 0.67 | 0.62 | 0.18 | 0.13 |
|  | $C_{ECR}$ (ppm) | 0.04 | 0.29 | 0.07 | 0.12 | 0.28 | 0.42 | 0.47 |
|  | $C_{BA}$ (ppm) | 7.9 | 0.76 | 10.0 | 10.7 | 11.5 | 1.8 | 2.1 |
|  | $C_{CR}/C_{ECR}$ | 45.2 | 3.4 | 10.7 | 5.6 | 2.2 | 0.4 | 0.3 |
|  | $C_{CR}/C_{BA}$ | 0.24 | 1.30 | 0.08 | 0.06 | 0.05 | 0.10 | 0.06 |
| Product permanganate time (min) |  | 20 | 50 | 80 | 100 | 120 | 360 | 400 |

Consideration of Results

Comparisons between Comparative Example 1 and Examples 1 to 3 demonstrate as follows. Specifically, synergistic effects lower the ratio $C_{CR}/C_{BA}$ in the sidecut from the light ends column and lower the ratios $C_{CR}/C_{ECR}$ and $C_{CR}/C_{BA}$ in the acetic acid product obtained from the column bottom of the dehydration column; and this allows the acetic acid product not only to have a lower crotonaldehyde concentration, but also to have a better permanganate time, where the synergistic effects are obtained by operating the light ends column and the dehydration column at reflux ratios at specific levels or more; by maintaining the hydrogen partial pressure in the reactor at a high level; and by operating the crotonaldehyde-removing column under specific conditions. In particular, increase in reflux ratio at the light ends column allows crotonaldehyde to be concentrated at the column top of the light ends column, and recycling of the resulting overhead liquid from this column top to the reactor allows crotonaldehyde to be hydrogenated and converted through butanol to butyl acetate. This selectively lowers the crotonaldehyde concentration in the light ends column sidecut liquid (first acetic acid stream) as compared with the butyl acetate concentration, lowers the ratio $C_{CR}/C_{BA}$ in the sidecut from the light ends column, and lowers the ratios $C_{CR}/C_{ECR}$ and $C_{CR}/C_{BA}$ in the acetic acid product obtained from the column bottom of the dehydration column. Probably as a result of these, the second acetic acid stream (product) from the dehydration column has a lower crotonaldehyde concentration and has a better product permanganate time.

Comparisons between Comparative Example 1 and Comparative Example 2 demonstrate that, even without performing the crotonaldehyde-removing step, increase in feed amount to the acetaldehyde-removing column lowers the ratio $C_{CR}/C_{ECR}$ in the sidecut from the light ends column and the ratio $C_{CR}/C_{ECR}$ in the acetic acid product from the column bottom of the dehydration column, and allows the acetic acid product to have a lower crotonaldehyde concentration and to have a better permanganate time. However, comparisons among Comparative Examples 1 and 2, and Example 1 demonstrate that, as compared with the results obtained by Comparative Example 1, Example 1 improves the permanganate time to a higher degree than Comparative Example 2 does, because of synergistic effects of lowering specific ratios and performing the crotonaldehyde-removing step, although Example 1 lowers the ratio $C_{CR}/C_{ECR}$ in the sidecut from the light ends column and the ratio $C_{CR}/C_{ECR}$ in the acetic acid product from the column bottom of the dehydration column to smaller degrees than Comparative Example 2 does.

Comparisons of Comparative Example 1 with Examples 1, 4, and 5, and comparisons of Comparative Example 2 with Examples 4 and 5 demonstrate that specific synergistic effects can lower at least one of the ratio $C_{CR}/C_{ECR}$ in the sidecut from the light ends column, the ratio $C_{CR}/C_{ECR}$ and the ratio $C_{CR}/C_{BA}$ in the acetic acid product from the column bottom of the dehydration column and allow the acetic acid product not only to have a lower crotonaldehyde concentration, but also to have a better (longer) permanganate time, where the synergistic effects are obtained by operating the light ends column and the dehydration column at reflux ratios at specific levels or more, by maintaining the hydrogen partial pressure in the reactor at a high level, and by operating the crotonaldehyde-removing column under specific conditions. In particular, increase in amount of the organic phase to be subjected to acetaldehyde removal decreases the amount of acetaldehyde which will be recycled typically to the reactor, and this lowers the amount of crotonaldehyde formed in the reactor. In addition, increase in reflux ratio at the crotonaldehyde-removing column allows crotonaldehyde to be concentrated at the column bottom of the crotonaldehyde-removing column, and this can give an overhead liquid from which crotonaldehyde has been efficiently separated, and recycling of the overhead liquid typically to the reactor decreases the amount of crotonaldehyde which is present typically in the reactor. This selectively lowers the crotonaldehyde concentration as compared with the 2-ethylcrotonaldehyde concentration in the light ends column sidecut liquid (first acetic acid stream), and thereby lowers at least one of the ratio $C_{CR}/C_{ECR}$ in the sidecut from the light ends column, the ratio $C_{CR}/C_{ECR}$ and the ratio $C_{CR}/C_{BA}$ in the acetic acid product from the column bottom of the dehydration column. Probably as a result of these, the second acetic acid stream from the dehydration column has a lower crotonaldehyde concentration and has a better (longer) permanganate time.

Comparisons of Example 1 with Examples 4 and 5 demonstrate that, provided that the light ends column and dehydration column are operated at reflux ratios at specific levels or more, the hydrogen partial pressure in the reactor is maintained high, and the crotonaldehyde-removing column is operated under specific conditions, the acetic acid product has a still lower crotonaldehyde concentration and has a still better (longer) permanganate time by synergistic effects of increasing the amount of the organic phase to be subjected to acetaldehyde removal, increasing the reflux ratio at the crotonaldehyde-removing column, and, in addition, increasing the reflux ratio at the dehydration column, to still lower the ratios $C_{CR}/C_{ECR}$ and $C_{CR}/C_{BA}$ in the light ends column sidecut, as compared with the case where the ratios $C_{CR}/C_{ECR}$ and $C_{CR}/C_{BA}$ in the light ends column sidecut are lowered only by increasing the amount of the organic phase to be subjected to acetaldehyde removal and increasing the reflux ratio at the crotonaldehyde-removing column.

Comparisons between Example 1 and Example 2 demonstrate that increase in reflux amount in at least one of the light ends column and the dehydration column allows crotonaldehyde to be concentrated at the column top, and thereby increases the crotonaldehyde concentration in a liquid to be recycled to the reactor. The crotonaldehyde reacts with acetaldehyde to give 2-ethylcrotonaldehyde (crotonaldehyde+acetaldehyde→2-ethylcrotonaldehyde), and thus 2-ethylcrotonaldehyde is increased. This increases the 2-ethylcrotonaldehyde concentrations in the charge liquid to the light ends column, the first acetic acid stream, and the second acetic acid stream, decreases or lowers the ratios $C_{CR}/C_{ECR}$ in the first acetic acid stream and the second acetic acid stream, and increases (improves) the product permanganate time as a whole, because 2-ethylcrotonaldehyde has lower sensitivity to (less affects) the permanganate time, as compared with crotonaldehyde.

These results and considerations demonstrate that lowering of at least one of the ratios $C_{CR}/C_{ECR}$ and $C_{CR}/C_{BA}$ in at least one of the light ends column sidecut and the dehydration column bottoms contributes to a better product permanganate time. The results and considerations also demonstrate that specific synergistic effects can give remarkably better quality than expected, where the synergistic effects are obtained by increasing the reflux ratio in at least one of the light ends column and the dehydration column to allow crotonaldehyde to be concentrated at the column top, and recycling the crotonaldehyde to the reactor to be converted into 2-ethylcrotonaldehyde and/or butyl acetate in the reactor (crotonaldehyde+acetaldehyde→2-ethylcrotonaldehyde, crotonaldehyde+hydrogen→butyl alcohol, butyl alcohol+acetic acid→butyl acetate); and by, while increasing the reflux ratio at the light ends column to allow crotonaldehyde to be concentrated at the column top, subjecting the overhead liquid (such as the organic phase) to a distillation treatment to thereby efficiently remove crotonaldehyde.

As a summary of the above description, configurations of the present invention, as well as variations thereof, will be described below as appendices.

(1) A method for producing acetic acid, the method including the steps of:

carbonylating methanol with carbon monoxide in a reactor in the presence of a catalytic system, acetic acid, methyl acetate, and water, to give acetic acid in a reaction mixture, the catalytic system including a metal catalyst and methyl iodide;

separating the reaction mixture resulting from the carbonylation step into a stream including the metal catalyst, an acetic acid stream rich in acetic acid, and a stream rich in light ends as compared with the acetic acid stream, using at least one selected from evaporators and distillation columns;

recycling at least a part of the light ends-rich stream to the reactor; and removing crotonaldehyde from at least a part of the remainder of the light ends-rich stream by a treatment in a distillation column;

wherein the separation step includes a first separation step of separating the reaction mixture into a first acetic acid stream rich in acetic acid, and an overhead stream rich in light ends as compared with the first acetic acid stream, using a first distillation column, and condensing the overhead stream to give a condensate, wherein a reflux ratio at the first distillation column is controlled as follows: provided that the condensate is liquid-liquid separated into an aqueous phase and an organic phase, the reflux ratio for the aqueous phase is 2 or more when the aqueous phase alone is refluxed to the first distillation column, the reflux ratio for the organic phase is 1 or more when the organic phase alone is refluxed to the first distillation column, and the total reflux ratio for the aqueous phase and the organic phase is 1.5 or more when both the aqueous phase and the organic phase are refluxed to the first distillation column, or provided that the condensate is refluxed to the first distillation column without liquid-liquid separation, the reflux ratio for the condensate is 1.5 or more, and the distillation column is operated in the crotonaldehyde-removing step so as to meet at least one of conditions (i) to (iii) as follows:

(i) a reflux ratio at the distillation column is 0.01 or more;

(ii) at the distillation column, the ratio of a crotonaldehyde concentration (ppm by mass) in a distillate to a crotonaldehyde concentration (ppm by mass) in a charge liquid is less than 1; and (iii) at the distillation column, the ratio of a crotonaldehyde concentration (ppm by mass) in bottoms to a crotonaldehyde concentration (ppm by mass) in the charge liquid is greater than 1, and wherein a crotonaldehyde concentration in the first acetic acid stream is controlled to 2.2 ppm by mass or less, and at least one ratio is lowered, to give an acetic acid product that yields a better potassium permanganate test result, where the at least one ratio is selected from the group consisting of the ratio ($C_{CR}/C_{ECR}$) of a crotonaldehyde concentration $C_{CR}$ (ppm by mass) to a 2-ethylcrotonaldehyde concentration $C_{ECR}$ (ppm by mass) in the first acetic acid stream, the ratio ($C_{CR}/C_{BA}$) of a crotonaldehyde concentration $C_{CR}$ (ppm by mass) to a butyl acetate concentration $C_{BA}$ (ppm by mass) in the first acetic acid stream, the ratio ($C_{CR}/C_{ECR}$) of a crotonaldehyde concentration $C_{CR}$ (ppm by mass) to a 2-ethylcrotonaldehyde concentration $C_{ECR}$ (ppm by mass) in an acetic acid-rich stream resulting from further purification of the first acetic acid stream, and the ratio ($C_{CR}/C_{BA}$) of a crotonaldehyde concentration $C_{CR}$ (ppm by mass) to a butyl acetate concentration $C_{BA}$ (ppm by mass) in the acetic acid-rich stream resulting from further purification of the first acetic acid stream.

(2) A method for producing acetic acid, the method including the steps of:

carbonylating methanol with carbon monoxide in a reactor in the presence of a catalytic system, acetic acid, methyl acetate, and water, to give acetic acid in a reaction mixture, the catalytic system including a metal catalyst and methyl iodide;

separating the reaction mixture resulting from the carbonylation step, using at least one selected from evaporators and distillation columns, into a stream including the metal catalyst, an acetic acid stream rich in acetic acid, and a stream rich in light ends as compared with the acetic acid stream;

recycling at least a part of the light ends-rich stream to the reactor; and removing crotonaldehyde from at least a part of the light ends-rich stream by a treatment in a distillation column, wherein the separation step includes:

a first separation step of separating the reaction mixture into a first acetic acid stream rich in acetic acid, and an overhead stream rich in light ends as compared with the first acetic acid stream, using a first distillation column, and condensing the overhead stream to give a condensate; and a second separation step of subjecting the first acetic acid stream to distillation in a second distillation column to further purify acetic acid, wherein a reflux ratio at the first distillation column is controlled as follows: provided that the condensate is liquid-liquid separated into an aqueous phase and an organic phase, the reflux ratio for the aqueous phase is 2 or more when the aqueous phase alone is refluxed to the first distillation column, the reflux ratio for the organic phase is 1 or more when the organic phase alone is refluxed to the first distillation column, and the total reflux ratio for the aqueous phase and the organic phase is 1.5 or more when both the aqueous phase and the organic phase are refluxed to the first distillation column, or provided that the condensate is refluxed to the first distillation column without liquid-liquid separation, the reflux ratio for the condensate is 1.5 or more, and the distillation column is operated in the crotonaldehyde-removing step so as to meet at least one of conditions (i) to (iii) as follows:

(i) a reflux ratio at the distillation column is 0.01 or more;

(ii) at the distillation column, the ratio of a crotonaldehyde concentration (ppm by mass) in a distillate to a crotonaldehyde concentration (ppm by mass) in a charge liquid is less than 1; and (iii) at the distillation column, the ratio of a crotonaldehyde concentration (ppm by mass) in bottoms to a crotonaldehyde concentration (ppm by mass) in the charge liquid is greater than 1, and wherein a crotonaldehyde concentration in the first acetic acid stream is controlled to 2.2 ppm by mass or less and/or a reflux ratio at the second distillation column is controlled to 0.1 or more, and at least one ratio is lowered, to give an acetic acid product that yields a better potassium permanganate test result, where the at least one ratio is selected from the group consisting of the ratio ($C_{CR}/C_{ECR}$) of a crotonaldehyde concentration $C_{CR}$ (ppm by mass) to a 2-ethylcrotonaldehyde concentration $C_{ECR}$ (ppm by mass) in the first acetic acid stream, the ratio ($C_{CR}/C_{BA}$) of a crotonaldehyde concentration $C_{CR}$ (ppm by mass) to a butyl acetate concentration $C_{BA}$ (ppm by mass) in the first acetic acid stream, the ratio ($C_{CR}/C_{ECR}$) of a crotonaldehyde concentration $C_{CR}$ (ppm by mass) to a 2-ethylcrotonaldehyde concentration $C_{ECR}$ (ppm by mass) in an acetic acid-rich stream from the second separation step, and the ratio ($C_{CR}/C_{BA}$) of a crotonaldehyde concentration $C_{CR}$ (ppm by mass) to a butyl acetate concentration $C_{BA}$ (ppm by mass) in the acetic acid-rich stream from the second separation step.

(3) The acetic acid production method according to one of (1) and (2), wherein the separation step includes:

an evaporation step of separating the reaction mixture resulting from the carbonylation step into a vapor stream and a residue stream using an evaporator; and as the first separation step, a light ends-removing step of separating the vapor stream, using a first distillation column, into a first overhead stream rich in at least one light end selected from methyl iodide and acetaldehyde, and the first acetic acid stream rich in acetic acid.

(4) The acetic acid production method according to (3), wherein the light ends-removing step includes liquid-liquid separation of a condensate derived from the first overhead stream into an aqueous phase and an organic phase.

(5) The acetic acid production method according to (4), wherein the crotonaldehyde-removing step includes removing crotonaldehyde from at least a part of at least one liquid by a treatment in the distillation column, where the at least one liquid is selected from the group consisting of the condensate resulting from condensation of the first overhead stream, the aqueous phase resulting from liquid-liquid separation of the condensate, and the organic phase resulting from liquid-liquid separation of the condensate.

(6) The acetic acid production method according to one of (4) and (5), further including an acetaldehyde-removing step of removing acetaldehyde from at least a part of at least one liquid by distillation, where the at least one liquid is selected from the group consisting of the condensate resulting from condensation of the first overhead stream, the aqueous phase resulting from liquid-liquid separation of the condensate, and the organic phase resulting from liquid-liquid separation of the condensate.

(7) The acetic acid production method according to (6), wherein at least a part of a residue after separation and removal of acetaldehyde from at least a part of at least one liquid is recycled to the reactor, where the at least one liquid is selected from the group consisting of the condensate, the aqueous phase resulting from liquid-liquid separation of the condensate, and the organic phase resulting from liquid-liquid separation of the condensate.

(8) The acetic acid production method according to any one of (3) to (7), wherein the separation step includes, as a second separation step, a dehydration step of separating the first acetic acid stream, using a second distillation column, into a second overhead stream rich in water, and a second acetic acid stream rich in acetic acid as compared with the first acetic acid stream.

(9) The acetic acid production method according to (8), wherein the recycling step includes recycling at least a part of at least one liquid into the reactor, where the at least one liquid is selected from the group consisting of the condensate resulting from condensation of the first overhead stream, the aqueous phase or the organic phase resulting from liquid-liquid separation of the condensate, and the second overhead stream.

(10) The acetic acid production method according to one of (8) and (9), wherein the second distillation column is operated at a reflux ratio of 0.1 or more (for example, 0.3 or more, preferably 0.32 or more, more preferably 1.0 or more, furthermore preferably 5.0 or more, particularly preferably 10 or more, and especially preferably 12 or more).

(11) The acetic acid production method according to any one of (8) to (10), wherein the upper limit of the reflux ratio at the second distillation column is 3000 (preferably 1000, more preferably 200, and furthermore preferably 100).

(12) The acetic acid production method according to any one of (8) to (11), wherein the second acetic acid stream has a crotonaldehyde concentration of 2.0 ppm by mass or less (preferably 1.8 ppm by mass or less, more preferably 1.5 ppm by mass or less, furthermore preferably 1.2 ppm by mass or less, particularly preferably 0.7 ppm by mass or less, and especially preferably 0.5 ppm by mass or less).

(13) The acetic acid production method according to any one of (8) to (12), wherein the second acetic acid stream has a 2-ethylcrotonaldehyde concentration of 3.0 ppm by mass or less (preferably 1.8 ppm by mass or less, more preferably 1.5 ppm by mass or less, furthermore preferably 1.2 ppm by mass or less, particularly preferably 0.7 ppm by mass or less, and especially preferably 0.5 ppm by mass or less).

(14) The acetic acid production method according to any one of (8) to (13), wherein the second acetic acid stream has a ratio ($C_{CR}/C_{ECR}$) of the crotonaldehyde concentration $C_{CR}$ (ppm by mass) to the 2-ethylcrotonaldehyde concentration $C_{ECR}$ (ppm by mass) of 50 or less (preferably 35 or less, more preferably 25 or less, furthermore preferably 20 or less, and particularly preferably 15 or less).

(15) The acetic acid production method according to any one of (8) to (14), wherein the second acetic acid stream has a butyl acetate concentration of 15 ppm by mass or less (preferably 12 ppm by mass or less, more preferably 10 ppm by mass or less, and furthermore preferably 8 ppm by mass or less).

(16) The acetic acid production method according to any one of (8) to (15), wherein the second acetic acid stream has a ratio ($C_{CR}/C_{BA}$) of the crotonaldehyde concentration $C_{CR}$ (ppm by mass) to the butyl acetate concentration $C_{BA}$ (ppm by mass) of 2.0 or less (preferably 1.5 or less, more preferably 1.0 or less, and furthermore preferably 0.6 or less).

(17) The acetic acid production method according to any one of (8) to (16), wherein the second acetic acid stream has a crotonaldehyde concentration of 0.98 ppm by mass or less (preferably 0.80 ppm by mass or less, more preferably 0.50 ppm by mass or less, and furthermore preferably 0.30 ppm by mass or less) and/or a 2-ethylcrotonaldehyde concentration of 1.0 ppm by mass or less (preferably 0.50 ppm by mass or less, more preferably 0.30 ppm by mass or less, and furthermore preferably 0.20 ppm by mass or less) and/or a butyl acetate concentration of 15 ppm by mass or less (preferably 10 ppm by mass or less, more preferably 8 ppm by mass or less, furthermore preferably 5 ppm by mass or less, and particularly preferably 3 ppm by mass or less).

(18) The acetic acid production method according to any one of (8) to (17), wherein the second acetic acid stream yields a potassium permanganate test result of longer than 50 minutes (preferably 60 minutes or longer, more preferably 100 minutes or longer, furthermore preferably 120 minutes or longer, particularly preferably 180 minutes or longer, especially preferably 240 minutes or longer, and still especially preferably 360 minutes or longer).

(19) The acetic acid production method according to any one of (1) to (18), wherein the catalytic system further includes an ionic iodide.

(20) The acetic acid production method according to any one of (1) to (19), wherein a hydrogen partial pressure in the reactor is 0.001 MPa (absolute pressure) or more (preferably, 0.005 MPa or more, more preferably 0.01 MPa (absolute pressure) or more (for example, 0.015 MPa or more), furthermore preferably 0.02 MPa (absolute pressure) or more, particularly preferably 0.04 MPa (absolute pressure) or more, and especially preferably 0.06 MPa (absolute pressure) or more (for example, 0.07 MPa (absolute pressure) or more)).

(21) The acetic acid production method according to any one of (1) to (20), wherein the upper limit of the hydrogen partial pressure in the reactor is 0.5 MPa (absolute pressure) (and preferably 0.2 MPa (absolute pressure)).

(22) The acetic acid production method according to any one of (1) to (21), wherein a liquid reaction mixture in the reactor has an acetaldehyde concentration of 500 ppm by mass or less (preferably 450 ppm by mass or less, more preferably 400 ppm by mass or less, furthermore preferably 350 ppm by mass or less, particularly preferably 300 ppm by mass or less, and especially preferably 250 ppm by mass or less).

(23) The acetic acid production method according to any one of (1) to (22), wherein the liquid reaction mixture in the reactor has a crotonaldehyde concentration of 5 ppm by mass or less (preferably 3 ppm by mass or less, and more preferably 2 ppm by mass or less).

(24) The acetic acid production method according to any one of (1) to (23), wherein the liquid reaction mixture in the reactor has a 2-ethylcrotonaldehyde concentration of 5 ppm by mass or less (preferably 3 ppm by mass or less, and more preferably 2 ppm by mass or less).

(25) The acetic acid production method according to any one of (1) to (24), wherein the liquid reaction mixture in the reactor has a butyl acetate concentration of 0.1 to 15 ppm by mass (preferably 1 to 12 ppm by mass, and more preferably 2 to 9 ppm by mass).

(26) The acetic acid production method according to any one of (1) to (25), wherein the first acetic acid stream has a 2-ethylcrotonaldehyde concentration of 3.0 ppm by mass or less (preferably 2.0 ppm by mass or less, more preferably 1.0 ppm by mass or less, furthermore preferably 0.8 ppm by mass or less, and particularly preferably 0.5 ppm by mass or less).

(27) The acetic acid production method according to any one of (1) to (26), wherein the first acetic acid stream has a ratio ($C_{CR}/C_{ECR}$) of the crotonaldehyde concentration $C_{CR}$ (ppm by mass) to the 2-ethylcrotonaldehyde concentration $C_{ECR}$ (ppm by mass) of 50 or less (preferably 35 or less, more preferably 25 or less, furthermore preferably 20 or less, and particularly preferably 15 or less).

(28) The acetic acid production method according to any one of (1) to (27), wherein the first acetic acid stream has a butyl acetate concentration of 15 ppm by mass or less (preferably 12 ppm by mass or less, more preferably 10 ppm by mass or less, and furthermore preferably 8 ppm by mass or less).

(29) The acetic acid production method according to any one of (1) to (28), wherein the first acetic acid stream has a ratio ($C_{CR}/C_{BA}$) of the crotonaldehyde concentration $C_{CR}$ (ppm by mass) to the butyl acetate concentration $C_{BA}$ (ppm by mass) of 2.0 or less (preferably 1.5 or less, more preferably 1.0 or less, and furthermore preferably 0.6 or less).

(30) The acetic acid production method according to any one of (1) to (29), wherein the crotonaldehyde concentration in the first acetic acid stream is controlled to 2.0 ppm by mass or less (preferably 1.8 ppm by mass or less, more preferably 1.5 ppm by mass or less, furthermore preferably 1.2 ppm by mass or less, particularly preferably 1.0 ppm by mass or less, especially preferably 0.8 ppm by mass or less, and still especially preferably 0.5 ppm by mass or less).

(31) The acetic acid production method according to any one of (1) to (30), wherein the first acetic acid stream has a crotonaldehyde concentration of 1.3 ppm by mass or less (preferably 1.0 ppm by mass or less, more preferably 0.85 ppm by mass or less, furthermore preferably 0.5 ppm by mass or less, and particularly preferably 0.25 ppm by mass or less) and/or a 2-ethylcrotonaldehyde concentration of 1.0 ppm by mass or less (preferably 0.50 ppm by mass or less) and/or a butyl acetate concentration of 15 ppm by mass or less (preferably 10 ppm by mass or less, more preferably 8 ppm by mass or less, furthermore preferably 5 ppm by mass or less, and particularly preferably 3 ppm by mass or less).

(32) The acetic acid production method according to any one of (3) to (31), wherein the vapor stream to be fed to the first distillation column has a crotonaldehyde concentration of 0 to 5.0 ppm by mass (preferably 0.01 to 4.0 ppm by mass, more preferably 0.1 to 3.0 ppm by mass, and furthermore preferably 0.2 to 2.0 ppm by mass) and/or a 2-ethylcrotonaldehyde concentration of 0 to 3.0 ppm by mass (preferably 0.01 to 2.5 ppm by mass, more preferably 0.02 to 2.0 ppm by mass, and furthermore preferably 0.03 to 0.8 ppm by mass) and/or a butyl acetate concentration of 0.1 to 13.0 ppm by mass (preferably 0.2 to 12.0 ppm by mass, and more preferably 0.3 to 9.0 ppm by mass).

(33) The acetic acid production method according to any one of (1) to (32), wherein the charge liquid fed to the distillation column in the crotonaldehyde-removing step has a crotonaldehyde concentration of 0.01 to 50 ppm by mass (preferably 0.1 to 50 ppm by mass, more preferably 0.3 to 30 ppm by mass, furthermore preferably 0.5 to 10 ppm by mass, particularly preferably 0.8 to 7.0 ppm by mass, and especially preferably 1.0 to 5.0 ppm by mass).

(34) The acetic acid production method according to any one of (1) to (33), wherein the distillation column is operated in the crotonaldehyde-removing step so as to meet all the conditions (i) to (iii).

(35) The acetic acid production method according to any one of (1) to (34), wherein distillation in the crotonaldehyde-removing step is performed batchwise.

(36) The acetic acid production method according to any one of (1) to (35), wherein the distillation column is operated in the crotonaldehyde-removing step at a throughput of 0.0001 to 50 parts by mass (preferably 0.001 to 30 parts by mass, more preferably 0.01 to 10 parts by mass, and furthermore preferably 0.1 to 5 parts by mass), per 100 parts by mass of the amount of the vapor stream fed to the first distillation column.

(37) The acetic acid production method according to any one of (1) to (36), wherein an overhead condensate from the distillation column in the crotonaldehyde-removing step is recycled to at least one of the aqueous phase, the organic phase, and the reactor.

(38) The acetic acid production method according to any one of (1) to (37), wherein the reflux ratio at the first distillation column is controlled so that the reflux ratio for the aqueous phase is 3 or more (preferably 5 or more, more preferably 8 or more, and furthermore preferably 12 or more) when the aqueous phase alone is refluxed to the first distillation column.

(39) The acetic acid production method according to any one of (1) to (38), wherein the reflux ratio at the first distillation column is controlled so that the reflux ratio for the organic phase is 1.5 or more (preferably 2 or more, more preferably 4 or more, and furthermore preferably 5 or more) when the organic phase alone is refluxed to the first distillation column.

(40) The acetic acid production method according to any one of (1) to (39), wherein the reflux ratio at the first distillation column is controlled so that the total reflux ratio for the aqueous phase and the organic phase is 2.3 or more (preferably 3.5 or more, more preferably 6 or more, and furthermore preferably 8.5 or more) when both the aqueous phase and the organic phase are refluxed to the first distillation column.

(41) The acetic acid production method according to any one of (1) to (40), wherein the upper limit of the reflux ratio at the first distillation column is 3000 (preferably 1000, more preferably 100, and furthermore preferably 30).

(42) The acetic acid production method according to any one of (1) to (41), wherein the reflux ratio at the distillation column in the condition (i) is controlled to 0.05 or more (preferably 0.5 or more, more preferably 5 or more, furthermore preferably 20 or more, and particularly preferably 30 or more).

(43) The acetic acid production method according to any one of (1) to (42), wherein the upper limit of the reflux ratio at the distillation column in the condition (i) is 1000.

(44) The acetic acid production method according to any one of (1) to (43), wherein, at the distillation column in the condition (ii), the ratio of the crotonaldehyde concentration (ppm by mass) in the distillate to the crotonaldehyde concentration (ppm by mass) in the charge liquid is controlled to 0.95 or less (preferably 0.80 or less, more preferably 0.70 or less, furthermore preferably 0.60 or less, particularly preferably 0.50 or less, especially preferably 0.30 or less, and still especially preferably 0.20 or less).

(45) The acetic acid production method according to any one of (1) to (44), wherein, at the distillation column in the condition (iii), the ratio of the crotonaldehyde concentration (ppm by mass) in the bottoms to the crotonaldehyde concentration (ppm by mass) in the charge liquid is controlled to 1.2 or more (preferably 1.5 or more, more preferably 2.0 or more, furthermore preferably 3.0 or more, particularly preferably 4.0 or more, especially preferably 5.0 or more, still especially preferably 10 or more, and particularly preferably 20 or more).

(46) The acetic acid production method according to any one of (1) to (45), wherein, in the crotonaldehyde-removing step, crotonaldehyde is concentrated at the column bottom of the distillation column and discharged, together with acetic acid as bottoms, out of the system.

(47) The acetic acid production method according to any one of (1) to (46), wherein, when distillation in the crotonaldehyde-removing step is continuously performed, a feed liquid is fed to a portion of the distillation column at a level lower by 20% to 80% (two-tenths to eight-tenths) from the top in a height direction of the distillation column.

(48) The acetic acid production method according to any one of (1) to (47), wherein, in the crotonaldehyde-removing step, at least a part of the condensate derived from the overhead vapor from the distillation column is refluxed to the distillation column, and at least another part of the condensate is drawn as a distillate and recycled to at least one of the aqueous phase, the organic phase, and the reactor.

(49) The acetic acid production method according to any one of (1) to (48), wherein bottoms including crotonaldehyde are drawn from the column bottom of the distillation column in the crotonaldehyde-removing step.

(50) The acetic acid production method according to any one of (1) to (49), wherein the reflux ratio at the first distillation column is controlled so that the reflux ratio for the aqueous phase is 2 or more.

(51) The acetic acid production method according to any one of (1) to (50), wherein the vapor stream has a crotonaldehyde concentration of 0 to 5 ppm by mass (preferably 0.1 to 3 ppm by mass, and more preferably 0.2 to 2 ppm by mass).

(52) The acetic acid production method according to any one of (1) to (51), wherein the vapor stream has a 2-ethylcrotonaldehyde concentration of 0 to 3 ppm by mass (preferably 0.02 to 2 ppm by mass, and more preferably 0.03 to 0.8 ppm by mass).

(53) The acetic acid production method according to any one of (1) to (52), wherein the vapor stream has a butyl acetate concentration of 0.1 to 13 ppm by mass (preferably 0.2 to 12 ppm by mass, and more preferably 0.3 to 9 ppm by mass).

(54) The acetic acid production method according to any one of (1) to (53), wherein the ratio ($C_{CR}/C_{ECR}$) of the crotonaldehyde concentration $C_{CR}$ (ppm by mass) to the 2-ethylcrotonaldehyde concentration $C_{ECR}$ (ppm by mass) in the first acetic acid stream is lowered.

(55) The acetic acid production method according to any one of (1) to (54), wherein the ratio ($C_{CR}/C_{BA}$) of the crotonaldehyde concentration $C_{CR}$ (ppm by mass) to the butyl acetate concentration $C_{BA}$ (ppm by mass) in the first acetic acid stream is lowered.

(56) The acetic acid production method according to any one of (1) to (55), wherein the ratio ($C_{CR}/C_{ECR}$) of the crotonaldehyde concentration $C_{CR}$ (ppm by mass) to the 2-ethylcrotonaldehyde concentration $C_{ECR}$ (ppm by mass) in an acetic acid-rich stream resulting from further purification of the first acetic acid stream is lowered.

(57) The acetic acid production method according to any one of (1) to (56), wherein the ratio ($C_{CR}/C_{BA}$) of the crotonaldehyde concentration $C_{CR}$ (ppm by mass) to the butyl acetate concentration $C_{BA}$ (ppm by mass) in an acetic acid-rich stream resulting from further purification of the first acetic acid stream is lowered.

(58) The acetic acid production method according to any one of (1) to (57), wherein the acetic acid-rich stream resulting from further purification of the first acetic acid stream is a second acetic acid stream.

INDUSTRIAL APPLICABILITY

The acetic acid production methods according to the present invention are usable as methods for industrially producing acetic acid by a methanol carbonylation process (methanol-acetic acid process).

REFERENCE SIGNS LIST 1 reactor
2 evaporator
3, 5, 6, 10 distillation column
4 decanter
7 ion exchange resin column
8 scrubber system
9 acetaldehyde removing system
16 reaction mixture feed line
17 vapor stream discharge line
18, 19 residue recycling line
54 carbon monoxide-containing gas introducing line
55, 56 potassium hydroxide introducing line
57 catalyst-circulating pump
91 distillation column (first acetaldehyde-removing column)
92 extraction column
93 distillation column (second acetaldehyde-removing column)
94 distillation column (extractive distillation column)
95 decanter
96 decanter
97 distillation column (acetaldehyde-removing column)
98 distillation column (extractive distillation column)
99 decanter
200 chimney tray

The invention claimed is:
1. A method for producing acetic acid, the method comprising the steps of:
carbonylating methanol with carbon monoxide in a reactor in the presence of a catalytic system, acetic acid, methyl acetate, and water, to give acetic acid in a reaction mixture, the catalytic system including a metal catalyst and methyl iodide;
separating the reaction mixture resulting from the carbonylation step, using at least one selected from evaporators and distillation columns, into at least:
a stream including the metal catalyst;
an acetic acid stream rich in acetic acid; and
a stream rich in light ends as compared with the acetic acid stream;
recycling at least a part of the light ends-rich stream to the reactor; and
removing crotonaldehyde from at least a part of a remainder of the light ends-rich stream by a treatment in a distillation column,
wherein the separation step comprises
a first separation step of separating the reaction mixture, using a first distillation column, into at least a first acetic acid stream rich in acetic acid, and an overhead stream rich in light ends as compared with the first acetic acid stream, and condensing the overhead stream to give a condensate,
wherein a reflux ratio at the first distillation column is controlled as follows:
provided that the condensate is liquid-liquid separated into an aqueous phase and an organic phase,
the reflux ratio for the aqueous phase is 2 or more when the aqueous phase alone is refluxed to the first distillation column;
the reflux ratio for the organic phase is 1 or more when the organic phase alone is refluxed to the first distillation column; and
the total reflux ratio for the aqueous phase and the organic phase is 1.5 or more when both the aqueous phase and the organic phase are refluxed to the first distillation column, or
provided that the condensate is refluxed to the first distillation column without liquid-liquid separation,
the reflux ratio for the condensate is 1.5 or more,
wherein the distillation column is operated in the crotonaldehyde-removing step so as to meet at least one of conditions (i) to (iii) as follows:
(i) a reflux ratio at the distillation column is 0.01 or more;
(ii) at the distillation column, a ratio of a crotonaldehyde concentration (ppm by mass) in a distillate to a crotonaldehyde concentration (ppm by mass) in a charge liquid is less than 1; and
(iii) at the distillation column, a ratio of a crotonaldehyde concentration (ppm by mass) in bottoms to a crotonaldehyde concentration (ppm by mass) in the charge liquid is greater than 1, and
wherein a crotonaldehyde concentration in the first acetic acid stream is controlled to 2.2 ppm by mass or less, and at least one ratio is lowered, to give an acetic acid product that yields a better potassium permanganate test result, where the at least one ratio is selected from the group consisting of:
a ratio ($C_{CR}/C_{ECR}$) of a crotonaldehyde concentration $C_{CR}$ (ppm by mass) to a 2-ethylcrotonaldehyde concentration $C_{ECR}$ (ppm by mass) in the first acetic acid stream;
a ratio ($C_{CR}/C_{BA}$) of a crotonaldehyde concentration $C_{CR}$ (ppm by mass) to a butyl acetate concentration $C_{BA}$ (ppm by mass) in the first acetic acid stream;
a ratio ($C_{CR}/C_{ECR}$) of a crotonaldehyde concentration $C_{CR}$ (ppm by mass) to a 2-ethylcrotonaldehyde concentration $C_{ECR}$ (ppm by mass) in an acetic acid-rich stream resulting from further purification of the first acetic acid stream; and
a ratio ($C_{CR}/C_{BA}$) of a crotonaldehyde concentration $C_{CR}$ (ppm by mass) to a butyl acetate concentration $C_{BA}$ (ppm by mass) in the acetic acid-rich stream resulting from further purification of the first acetic acid stream.

2. A method for producing acetic acid, the method comprising the steps of:
carbonylating methanol with carbon monoxide in a reactor in the presence of a catalytic system, acetic acid, methyl acetate, and water, to give acetic acid in a reaction mixture, the catalytic system including a metal catalyst and methyl iodide;
separating the reaction mixture resulting from the carbonylation step, using at least one selected from evaporators and distillation columns, into at least:
a stream including the metal catalyst;
an acetic acid stream rich in acetic acid; and
a stream rich in light ends as compared with the acetic acid stream;
recycling at least a part of the light ends-rich stream to the reactor; and
removing crotonaldehyde from at least a part of a remainder of the light ends-rich stream by a treatment in a distillation column,
wherein the separation step comprises:
a first separation step of separating the reaction mixture, using a first distillation column, into at least a first acetic acid stream rich in acetic acid, and an overhead stream rich in light ends as compared with the first acetic acid stream, and condensing the overhead stream to give a condensate; and
a second separation step of subjecting the first acetic acid stream to distillation in a second distillation column to further purify acetic acid,
wherein a reflux at the first distillation column is controlled as follows:
provided that the condensate is liquid-liquid separated into an aqueous phase and an organic phase,
the reflux ratio for the aqueous phase is 2 or more when the aqueous phase alone is refluxed to the first distillation column;
the reflux ratio for the organic phase is 1 or more when the organic phase alone is refluxed to the first distillation column; and
the total reflux ratio for the aqueous phase and the organic phase is 1.5 or more when both the aqueous phase and the organic phase are refluxed to the first distillation column, or
provided that the condensate is refluxed to the first distillation column without liquid-liquid separation,
the reflux ratio for the condensate is 1.5 or more,
wherein the distillation column is operated in the crotonaldehyde-removing step so as to meet at least one of conditions (i) to (iii) as follows:
(i) a reflux ratio at the distillation column is 0.01 or more;
(ii) at the distillation column, a ratio of a crotonaldehyde concentration (ppm by mass) in a distillate to a crotonaldehyde concentration (ppm by mass) in a charge liquid is less than 1; and
(iii) at the distillation column, a ratio of a crotonaldehyde concentration (ppm by mass) in bottoms to a crotonaldehyde concentration (ppm by mass) in the charge liquid is greater than 1, and
wherein a crotonaldehyde concentration in the first acetic acid stream is controlled to 2.2 ppm by mass or less and/or a reflux ratio at the second distillation column is controlled to 0.1 or more, and at least one ratio is lowered, to give an acetic acid product that yields a better potassium permanganate test result, where the at least one ratio is selected from the group consisting of:
a ratio ($C_{CR}/C_{ECR}$) of a crotonaldehyde concentration $C_{CR}$ (ppm by mass) to a 2-ethylcrotonaldehyde concentration $C_{ECR}$ (ppm by mass) in the first acetic acid stream;
a ratio ($C_{CR}/C_{BA}$) of a crotonaldehyde concentration $C_{CR}$ (ppm by mass) to a butyl acetate concentration $C_{BA}$ (ppm by mass) in the first acetic acid stream;
a ratio ($C_{CR}/C_{ECR}$) of a crotonaldehyde concentration $C_{CR}$ (ppm by mass) to a 2-ethylcrotonaldehyde concentration $C_{ECR}$ (ppm by mass) in an acetic acid-rich stream from the second separation step; and
a ratio ($C_{CR}/C_{BA}$) of a crotonaldehyde concentration $C_{CR}$ (ppm by mass) to a butyl acetate concentration $C_{BA}$ (ppm by mass) in the acetic acid-rich stream from the second separation step.

3. The acetic acid production method according to claim 1,
wherein the separation step comprises:
an evaporation step of separating the reaction mixture resulting from the carbonylation step into a vapor stream and a residue stream, using an evaporator; and
a light ends-removing step, as the first separation step, of separating the vapor stream, using the first distillation column, into at least a first overhead stream rich in at least one light end selected from methyl iodide and acetaldehyde, and the first acetic acid stream rich in acetic acid, and condensing the first overhead stream to give a condensate.

4. The acetic acid production method according to claim 3,
wherein the light ends-removing step comprises
liquid-liquid separating the condensate derived from the first overhead stream into an aqueous phase and an organic phase.

5. The acetic acid production method according to claim 4,
wherein the crotonaldehyde-removing step comprises
removing crotonaldehyde from at least a part of at least one liquid by a treatment in the distillation column, where the at least one liquid is selected from the group consisting of:
the condensate resulting from condensation of the first overhead stream;
the aqueous phase resulting from liquid-liquid separation of the condensate; and
the organic phase resulting from liquid-liquid separation of the condensate.

6. The acetic acid production method according to claim 4, further comprising the step of:
removing acetaldehyde from at least a part of at least one liquid by distillation, where the at least one liquid is selected from the group consisting of:
the condensate resulting from condensation of the first overhead stream;
the aqueous phase resulting from liquid-liquid separation of the condensate; and
the organic phase resulting from liquid-liquid separation of the condensate.

7. The acetic acid production method according to claim 6,
wherein at least a part of a residue is recycled to the reactor, where the residue is a residue after the separation and removal of acetaldehyde from the at least a part of at least one liquid, where the at least one liquid is selected from the group consisting of the condensate, the aqueous phase resulting from liquid-liquid separation of the condensate, and the organic phase resulting from liquid-liquid separation of the condensate.

8. The acetic acid production method according to claim 3, wherein the separation step comprises
a dehydration step, as a second separation step, of separating the first acetic acid stream, using a second distillation column, into at least:
a second overhead stream rich in water; and
a second acetic acid stream rich in acetic acid as compared with the first acetic acid stream.

9. The acetic acid production method according to claim 8, wherein the recycling step comprises
recycling at least a part of at least one liquid to the reactor, where the at least one liquid is selected from the group consisting of:
the condensate resulting from condensation of the first overhead stream;
the aqueous phase or the organic phase resulting from liquid-liquid separation of the condensate; and
the second overhead stream.

10. The acetic acid production method according to claim 8, wherein the second distillation column is operated at a reflux ratio of 0.1 or more.

11. The acetic acid production method according to claim 8, wherein the second acetic acid stream has a crotonaldehyde concentration of 2.0 ppm by mass or less.

12. The acetic acid production method according to claim 8, wherein the second acetic acid stream has a 2-ethylcrotonaldehyde concentration of 3.0 ppm by mass or less.

13. The acetic acid production method according to claim 8, wherein the second acetic acid stream has a ratio ($C_{CR}/C_{ECR}$) of the crotonaldehyde concentration $C_{CR}$ (ppm by mass) to the 2-ethylcrotonaldehyde concentration $C_{ECR}$ (ppm by mass) of 50 or less.

14. The acetic acid production method according to claim 8, wherein the second acetic acid stream has a butyl acetate concentration of 15 ppm by mass or less.

15. The acetic acid production method according to claim 8, wherein the second acetic acid stream has a ratio ($C_{CR}/C_{BA}$) of the crotonaldehyde concentration $C_{CR}$ (ppm by mass) to the butyl acetate concentration $C_{BA}$ (ppm by mass) of 2.0 or less.

16. The acetic acid production method according to claim 8, wherein the second acetic acid stream has a crotonaldehyde concentration of 0.98 ppm by mass or less, and/or a 2-ethylcrotonaldehyde concentration of 1.0 ppm by mass or less, and/or a butyl acetate concentration of 15 ppm by mass or less.

17. The acetic acid production method according to claim 8, wherein the second acetic acid stream yields a potassium permanganate test result of longer than 50 minutes.

18. The acetic acid production method according to claim 1, wherein the catalytic system further includes an ionic iodide.

19. The acetic acid production method according to claim 1, wherein a hydrogen partial pressure in the reactor is 0.001 MPa (absolute pressure) or more.

20. The acetic acid production method according to claim 1, wherein a liquid reaction mixture in the reactor has an acetaldehyde concentration of 500 ppm by mass or less.

* * * * *